US012227503B2

(12) United States Patent
Lowry et al.

(10) Patent No.: US 12,227,503 B2
(45) Date of Patent: *Feb. 18, 2025

(54) COMPOSITIONS AND METHODS FOR MODULATING HAIR GROWTH

(71) Applicant: The Regents of the University of California, Oakland, CA (US)

(72) Inventors: William E. Lowry, Los Angeles, CA (US); Michael E. Jung, Los Angeles, CA (US); Heather R. Christofk, Los Angeles, CA (US); Xiaoguang Liu, Santa Monica, CA (US); Aimee Flores, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/241,583

(22) Filed: Sep. 1, 2023

(65) Prior Publication Data

US 2024/0025895 A1 Jan. 25, 2024

Related U.S. Application Data

(63) Continuation of application No. 17/847,980, filed on Jun. 23, 2022, now Pat. No. 11,787,804, which is a continuation of application No. 17/584,091, filed on Jan. 25, 2022, now Pat. No. 11,472,804, which is a continuation of application No. 16/627,630, filed as application No. PCT/US2018/040385 on Jun. 29, 2018, now Pat. No. 11,312,714.

(60) Provisional application No. 62/654,095, filed on Apr. 6, 2018, provisional application No. 62/527,775, filed on Jun. 30, 2017.

(51) Int. Cl.
C07D 471/04 (2006.01)
A61K 9/00 (2006.01)
A61P 17/14 (2006.01)
C07D 209/22 (2006.01)
C07D 413/06 (2006.01)
C07D 417/06 (2006.01)
C07F 9/535 (2006.01)

(52) U.S. Cl.
CPC .......... *C07D 471/04* (2013.01); *A61K 9/0014* (2013.01); *A61P 17/14* (2018.01); *C07D 209/22* (2013.01); *C07D 413/06* (2013.01); *C07D 417/06* (2013.01); *C07F 9/535* (2013.01)

(58) Field of Classification Search
CPC .. C07D 471/04; C07D 209/22; C07D 413/06; C07D 417/06; A61P 17/14; A61K 9/0014; C07F 9/535
USPC ........................................................ 544/143
See application file for complete search history.

(56) References Cited

U.S. PATENT DOCUMENTS

| | | | |
|---|---|---|---|
| 3,524,860 A | 8/1970 | Albertson | |
| 5,124,354 A | 6/1992 | Green | |
| 5,397,787 A | 3/1995 | Buzzetti et al. | |
| 5,663,346 A | 9/1997 | Buzzetti et al. | |
| 6,541,507 B1 | 4/2003 | Dalko et al. | |
| 9,499,551 B2 | 11/2016 | Jacobsen et al. | |
| 11,213,513 B2 | 1/2022 | Lowry et al. | |
| 11,312,714 B2 | 4/2022 | Lowry et al. | |
| 11,472,804 B2 | 10/2022 | Lowry et al. | |
| 11,787,804 B2 | 10/2023 | Lowry et al. | |
| 2008/0064765 A1 | 3/2008 | Birnbaum | |
| 2009/0269418 A1 | 10/2009 | Albeck et al. | |
| 2010/0305187 A1 | 12/2010 | Guelow et al. | |
| 2011/0028460 A1 | 2/2011 | Kisak et al. | |
| 2013/0023587 A1 | 1/2013 | Schroeder et al. | |
| 2013/0337031 A1 | 12/2013 | Kisak et al. | |
| 2015/0140071 A1 | 5/2015 | Rajasekaran | |
| 2020/0030289 A1 | 1/2020 | Lowry et al. | |
| 2020/0157093 A1 | 5/2020 | Lowry et al. | |
| 2020/0253917 A1 | 8/2020 | Lowry et al. | |
| 2022/0048908 A1 | 2/2022 | Lowry et al. | |
| 2022/0153738 A1 | 5/2022 | Lowry et al. | |
| 2023/0103693 A1 | 4/2023 | Jung et al. | |
| 2023/0114220 A1 | 4/2023 | Lowry et al. | |
| 2023/0322765 A1 | 10/2023 | Sun et al. | |

FOREIGN PATENT DOCUMENTS

| | | |
|---|---|---|
| CN | 1093707 A | 10/1994 |
| CN | 106880693 A | 6/2017 |
| DE | 3601285 A1 | 7/1987 |
| EP | 0403238 A2 | 12/1990 |
| EP | 0780389 A1 | 6/1997 |
| EP | 1068858 A1 | 1/2001 |
| JP | S 59-161357 A | 9/1984 |
| KR | 2004/0029371 A | 4/2004 |
| WO | WO-9200057 A1 | 1/1992 |

(Continued)

OTHER PUBLICATIONS

Date et al., "A Highly Regio- and Stereoselective Vinylogous Horner-Wadsworth-Emmons Route to Densely Substituted 1,3-Butadienes", Angewandte Chemie International Edition 46.3: 386-388 (2007).

(Continued)

*Primary Examiner* — Kristin A Vajda
(74) *Attorney, Agent, or Firm* — Foley Hoag LLP; David P. J. Halstead D.; Alexander J. J. Chatterley D.

(57) ABSTRACT

The present disclosure relates to compounds that are capable of inhibiting the mitochondrial pyruvate carrier and promoting hair growth. The disclosure further relates to methods of promoting hair growth or treating conditions or disorders affecting hair growth, such as baldness or alopecia.

13 Claims, 25 Drawing Sheets

(56) References Cited

FOREIGN PATENT DOCUMENTS

| WO | WO-1992/007839 A1 | 5/1992 |
|---|---|---|
| WO | WO-96/00226 A1 | 1/1996 |
| WO | WO-0162237 A2 | 8/2001 |
| WO | WO-03/007951 A1 | 1/2003 |
| WO | WO-2004/080481 A1 | 9/2004 |
| WO | WO-2005/051908 A1 | 6/2005 |
| WO | WO-2005/054247 A1 | 6/2005 |
| WO | WO-2005/123664 A2 | 12/2005 |
| WO | WO-2005/123731 A2 | 12/2005 |
| WO | WO-2007/002433 A1 | 1/2007 |
| WO | WO-2007/068418 A1 | 6/2007 |
| WO | WO-2007/099396 A2 | 9/2007 |
| WO | WO-2008/028118 A1 | 3/2008 |
| WO | WO-2009/059666 A1 | 5/2009 |
| WO | WO-2012/078649 A1 | 6/2012 |
| WO | WO-2013/128465 A1 | 9/2013 |
| WO | WO-2013/169956 A2 | 11/2013 |
| WO | WO-2013/188554 A1 | 12/2013 |
| WO | WO-2014/113467 A1 | 7/2014 |
| WO | WO-2014/207213 A1 | 12/2014 |
| WO | WO-2015/042053 A1 | 3/2015 |
| WO | WO-2015/049365 A2 | 4/2015 |
| WO | WO-2015/112854 A1 | 7/2015 |
| WO | WO-2017/196936 A1 | 11/2017 |
| WO | WO-2018/039612 A1 | 3/2018 |
| WO | WO-2018/039615 A1 | 3/2018 |
| WO | WO-2019/006359 A1 | 1/2019 |
| WO | WO-2020/142413 A1 | 7/2020 |
| WO | WO-2021/127482 A1 | 6/2021 |
| WO | WO-2022/006039 A1 | 1/2022 |
| WO | WO-2022/006040 A1 | 1/2022 |
| WO | WO-2021/127482 A8 | 6/2022 |

OTHER PUBLICATIONS

Gordon et al., "Development of Second-Generation Indole-Based Dynamin GTPase Inhibitors" Journal of Medicinal Chemistry, vol. 56, p. 46-59 (2013).
Krawyczyk et al., "Knoevenagel Reaction of Diethylphosphonoacetic Acid: A Facile Route to Diethyl (E)-2-Arylvinylphosphonates" Synthesis, No. 17, p. 2887-2896 (2005).
Moriya et al., "Preparation and reactions of 3-(aminomethylene)-3H-indoles", Chemical and Pharmaceutical Bulletin 28.6: 1711-1721 (1980).
Amin et al., "Exploring structural requirements of unconventional Knoevenagel-type indole derivatives as anticancer agents through comparative QSAR modeling approaches," Can J Chemistry, 94(7):637-644 (2016).
Brennan et al., "The Allosteric Site on SHP2's Protein Tyrosine Phosphatase Domain is Targetable with Druglike Small Molecules," ACS Omega, 3(11): 15763-15770 (2018).
CAS Registry No. 891610-48-3: CA Index Name "2-Propenamide, 2-cyano-3-[1-[[3-(trifluoromethyl)phenyl]methyl]-1H-indol-3-yl]-" STN International: 3 pages (2006).
CAS Registry No. 1332531-33-5, Entered STN: Sep. 15, 2011.
CAS Registry No. 891614-21-4, Entered STN: Jul. 10, 2006.
CAS Registry No. 907553-40-6, Entered STN: Sep. 19, 2006.
CAS Registry No. 925549-16-2, Entered STN: Mar. 8, 2007.
CAS Registry No. 139336-32-6: Entered STN: Feb. 28, 1992.
CAS Registry No. 861644-67-9: Entered STN: Aug. 24, 2005.
CAS Registry No. 96618-51-8: Entered STN: Jan. 3, 1985.
CAS Registry No. 374601-67-9, Entered STN: Dec. 10, 2001.
CAS Registry No. 677327-34-3; CA Index Name: 2-Propenamide, 2-cyano-N-ethyl-3-(1H-pyrrolo[2,3-b]pyridin-3-yl)-; Entered STN: Apr. 28, 2004.
CAS Registry No. 94331-28-9. Jan. 21, 1985.
CAS Registry No. 1025594-30-2, Entered STN:Jun. 5, 2008.
CAS Registry No. 1232821-01-0, Entered STN:Jul. 19, 2010.
CAS Registry No. 1246086-21-4, Entered STN:Oct. 12, 2010.
CAS Registry No. 1360583-75-0, Entered STN:Mar. 9, 2012.
CAS Registry No. 1360583-78-3, Entered STN:Mar. 9, 2012.
CAS Registry No. 1417368-01-4, Entered STN:Jan. 23, 2013.
CAS Registry No. 1993738-37-6, Entered STN:Sep. 16, 2016.
CAS Registry No. 1993795-68-8, Entered STN:Sep. 16, 2016.
CAS Registry No. 2022941-63-3, Entered STN:Nov. 2, 2016.
CAS Registry No. 2094959-90-5, Entered STN:May 5, 2017.
CAS Registry No. 677327-34-3, Entered STN:Apr. 28, 2004.
CAS Registry No. 895303-82-9, Entered STN:Jul. 23, 2006.
CAS Registry No. 895304-22-0, Entered STN:Jul. 23, 2006.
CAS Registry No. 904141-89-5, Entered STN: Aug. 24, 2006.
Castilho et al., "mTOR Mediates Wnt-Induced Epidermal Stem Cell Exhaustion and Aging," Cell Stem Cell, 5(3): 279-289 (25 pages) (2009).
Choi et al., "The effect of cilostazol, a phosphodiesterase 3 (PDE3) inhibitor, on human hair growth with the dual promoting mechanisms," Journal of Dermatological Science, 91: 60-68 (2018).
El Maatougui et al., "Supported TBD-Assisted Solution Phase Diversification of Formyl-Aza-Heterocycles Through Alkylation-Knoevenagel One Pot Sequences," Combinatorial Chemistry & High Throughput Screening, 14: 570-582 (2011).
Extended European Search Report for EP Application No. 17844520.1 mailed Jul. 21, 2020.
Extended European Search Report for EP Application No. 18823621 mailed Jun. 15, 2021.
Extended European Search Report for EP Application No. 18862674.1 dated Jun. 18, 2021.
Fairhurst et al., "A synthesis of CIS-$\alpha$, $\beta$-unsaturated nitriles by kinetically controlled decarboxylation" Tetrahedron Letters, No. 22, pp. 3843-3844 (1975).
Fischer et al., "Effect of caffeine and testosterone on the proliferation of human hair follicles in vitro," International Journal of Dermatology, 46: 27-35 (2007).
Flores et al., "Inhibition of pyruvate oxidation as a versatile stimulator of the hair cycle in models of alopecia," Experimental Dermatology, 30: 448-456 (2021).
Flores et al., "Lactate dehydrogenase activity drives hair follicle stem cell activation," Nature Cell Biology, 19(9): 1017-1026 (2017).
Harisha et al., "Reaction of 3-arylidenepropenoic acid derivatives with triethylamine and other amines; unexpected reductions and vinylogations" Tetrahedron Letters, No. 72, pp. 2880-2889 (2016).
Hickey et al., "Demodectic Mange in a Tamarin (*Saguinus geoffroyi*) 1,2," Laboratory Animal Science, American Associate for Laboratory Animal Science, 33(1): 192-193 (1983).
Hong et al., "Synthesis of double D-A branched organic dyes employing indole and phenoxazine as donors for efficient DSSCs," Tetrahedron, 70(36): 6296-6302 (2014).
International Preliminary Report on Patentability for International Application No. PCT/US2018/040385 mailed Dec. 31, 2019.
International Search Report and Written Opinion for International Application No. PCT/US2017/048701 dated Nov. 6, 2017.
International Search Report and Written Opinion for International Application No. PCT/US2018/040385 dated Oct. 21, 2018.
International Search Report and Written Opinion for International Application No. PCT/US2018/053351 mailed Dec. 31, 2018.
International Search Report and Written Opinion for International Application No. PCT/US2019/068905 dated Apr. 6, 2020.
International Search Report and Written Opinion for International Application No. PCT/US2020/066078 dated Mar. 25, 2021.
International Search Report and Written Opinion for International Application No. PCT/US2021/039501 mailed Sep. 30, 2021.
International Search Report and Written Opinion for International Application No. PCT/US2021/039502 mailed Sep. 30, 2021.
Issue Notification for U.S. Appl. No. 16/627,630 dated Apr. 6, 2022.
Jelinek et al., "Mapping Metabolism: Monitoring Lactate Dehydrogenase Activity Directly in Tissue," Journal of Visualized Experiments, 136: 57760 (2018).
Keren et al., "The PDE4 inhibitor, apremilast, suppresses experimentally induced alopecia areata in human skin in vivo," Journal of Dermatological Science, 77: 71-81 (2015).
Khan et al., "Arylindoles. II. N-Arylindole-3-carboxaldehydes and Their Derivatives," Chemical and Pharmaceutical Bulletin, 27(2): 528-531 (1979).

(56) References Cited

OTHER PUBLICATIONS

Liu et al., "Development of Novel Mitochondrial Pyruvate Carrier Inhibitors to Treat Hair Loss," Journal of Medicinal Chemistry, 64: 2046-2063 (2021).
Liu et al., "Identification of novel thiadiazoloacrylamide analogues as inhibitors of dengue-2 virus NS2B/NS3 protease," Bioorg Med Chem, 22(22):6344-6352 (2014).
Magar et al., "Synthesis of Some Novel 3-Substituted Indole Derivatives Using Polyamine Functionalized Heterogeneous Catalyst," Journal of Heterocyclic Chemistry, 52(6): 1684-1692 (2015).
McCommis et al., "Mitochondrial pyruvate transport: a historical perspective and future research directions," Biochem J, 466(3):443-454 (2015).
Miranda et al., "Topical Inhibition of the Electron Transport Chain Can Stimulate the Hair Cycle," Journal of Investigative Dermatology, 138(4):9680972 (2017).
Miranda et al., "Topical Inhibition of the Electron Transport Chain Can Stimulate the Hair Cycle," Journal of Investigative Dermatology, 138: 968-972 (2018).
Notice of Allowance for U.S. Appl. No. 17/584,091 dated Apr. 14, 2022.
Partial Supplementary European Search Report for EP Application No. EP 18823621 dated Mar. 15, 2021.
PubChem CID 6438504; "2-Cyano-3-(1-phenylindol-3-yl)acrylate," National Library of Medicine: 18 pages (Create date Apr. 28, 2006).
Salin et al., "Phosphine-catalyzed addition of P(O)—H compounds to ethyl phenylpropiolate" Tetrahedron Letters, No. 56, pp. 6282-6286 (2015).
Sarifakioglu., "Determination of the sildenafil effect on alopecia areata in childhood: An open-pilot comparison study," Journal of Dermatological Treatment, 17(4): 235-237 (2006).
Shan et al., "Phenanthroline-tBuOK Promoted Intramolecular C—H Arylation of Indoles with Arl under Transition-Metal-Free Conditions," Organic Letters, 20(24): 7898-7901 (2018).
Shearman et al., "The concentration of the mitochondrial pyruvate carrier in rat liver and heart mitochondria determined with a-cyano-ß-(1-phenylindol-3-yl)acrylate," Biochemical Journal 223(3): 673-676 (1984).
Shelke et al., "An Efficient Synthesis of 5-Arylidene-2,4-ThiazolidinedioneCatalyzed by Boric acid in Aqueous media under Ultrasound-Irradiation" Chemistry and Biology Interface, vol. 6, No. 6, pp. 410-415 (2016).
Starosyla et al., "Discovery of novel protein kinase FGFR1 inhibitors using pharmacophore modeling," Ukrainica Bioorganica Acta, 13(1): 13-20 w/ English Abstract (2015).
Taylor et al., "Src tyrosine kinsase activity in rat thecal—interstitial cells and mouse TM3 Leydig cells is positively associated with cAMP-specific phosphodiesterase activity," Molecular and Cellular Endocrinology, 126: 91-100 (1997).
Valdenaire et al., "Evolution of novel tricyclic CRTh2 receptor antagonists from a (E)-2-cyano-3-(1H-indol-3-yl)acrylamide scaffold," Bioorganic & Medicinal Chemistry Letters, 23(4): 944-948 (2013).
Vishnyakova et al., "Possible role of autophagy activation in stimulation of regeneration," Mol Biol, 47(5):692-700 (2013).
Wang et al., "Oxidative stress and substance P mediate psychological stress-induced autophagy and delay of hair growth in mice," Arch. Dermatol. Res. 307: 171-181 (2015).
Yakhontov et al., "Pyrrolo[2,3-b]pyridine derivatives (7-azaindoles) viii. Synthesis and some reactions of 4-methyl-1-phenyl-1h-4-methyl-1-phynyl-1 h-pyrrol0[2,3-b]pyridine-3-carboxaldehydel," All-Union Chem Pharma Res Int, translated from Zhurnal Obshchei Khimii 34(8):2603-2610 (1964).
Extended European Search Report for EP Application No. 20903755.5 dated Jan. 9, 2024.

Silverman et al., "The Organic Chemistry of Drug Design and Drug Action" translated by Guo Zongru, Chemical Industry Press, 1st edition, pp. 17-23, Jan. 31, 2008.
Extended European Search Report for Application No. 28132522.3 dated Dec. 11, 2023.
Extended European Search Report for EP Application No. 21832044.8 dated Dec. 7, 2023.
Zhou et al., "Structure-based discovery of new maternal embryonic leucine zipper kinase inhibitors", Organic & Biomolecular Chemistry, vol. 16, No. 9, pp. 1489-1495 (2018).
U.S. Appl. No. 16/488,451, Issued.
U.S. Appl. No. 16/627,630, Issued.
U.S. Appl. No. 17/584,091, Issued.
U.S. Appl. No. 17/847,980, Allowed.
U.S. Appl. No. 17/420,293, Pending.
U.S. Appl. No. 18/013,808, Pending.
U.S. Appl. No. 18/013,803, Pending.
U.S. Appl. No. 17/786,986, Pending.
U.S. Appl. No. 17/847,980, Issued.
Babu et al., "From Molecular Design to Co-sensitization; High performance indole based photosensitizers for dye-sensitized solar cells," Electrochimica Acta 198 (2016): 10-21.
STN Registry Database, RN 302562-57-8, entered Nov. 13, 2000.
STN Registry Database, RN 302562-58-9, entered Nov. 13, 2000.
STN Registry Database, RN 302825-78-1, entered Nov. 14, 2000.
STN Registry Database, RN 303202-38-2, entered Nov. 20, 2000.
STN Registry Database, RN 327076-80-2, entered Mar. 14, 2001.
STN Registry Database, RN 327076-81-3, entered Mar. 14, 2001.
STN Registry Database, RN 327076-82-4, entered Mar. 14, 2001.
STN Registry Database, RN 327076-84-6, entered Mar. 14, 2001.
STN Registry Database, RN 340212-10-4, entered Jun. 10, 2001.
STN Registry Database, RN 367469-20-3, entered Nov. 7, 2001.
STN Registry Database, RN 372973-07-4, entered Dec. 3, 2001.
STN Registry Database, RN 374092-98-5, entered Dec. 6, 2001.
STN Registry Database, RN 374601-46-4, entered Dec. 10, 2001.
STN Registry Database, RN 374601-67-9, entered Dec. 10, 2001.
STN Registry Database, RN 374697-43-5, entered Dec. 11, 2001.
STN Registry Database, RN 444567-77-5, entered Nov. 1, 2004.
STN Registry Database, RN 524732-67-0, entered Jun. 3, 2003.
STN Registry Database, RN 663203-03-0, entered Mar. 15, 2004.
STN Registry Database, RN 675864-84-3, entered Apr. 16, 2004.
STN Registry Database, RN 773082-62-5, entered Nov. 1, 2004.
STN Registry Database, RN 780812-59-1, entered Nov. 15, 2004.
STN Registry Database, RN 885523-21-7, entered May 25, 2006.
STN Registry Database, RN 890353-24-9, entered Jul. 3, 2006.
STN Registry Database, RN 890353-32-9, entered Jul. 3, 2006.
STN Registry Database, RN 891362-96-2, entered Jul. 10, 2006.
STN Registry Database, RN 891363-10-3, entered Jul. 10, 2006.
STN Registry Database, RN 891379-65-0, entered Jul. 10, 2006.
STN Registry Database, RN 891379-71-8, entered Jul. 10, 2006.
STN Registry Database, RN 891379-78-5, entered Jul. 10, 2006.
STN Registry Database, RN 891563-66-9, entered Jul. 10, 2006.
STN Registry Database, RN 891569-68-9, entered Jul. 10, 2006.
STN Registry Database, RN 891569-89-4, entered Jul. 10, 2006.
STN Registry Database, RN 891569-97-4, entered Jul. 10, 2006.
STN Registry Database, RN 891590-88-8, entered Jul. 10, 2006.
STN Registry Database, RN 891590-96-8, entered Jul. 10, 2006.
STN Registry Database, RN 891591-04-1, entered Jul. 10, 2006.
STN Registry Database, RN 891614-21-4, entered Jul. 10, 2006.
STN Registry Database, RN 891631-78-0, entered Jul. 10, 2006.
STN Registry Database, RN 891631-85-9, entered Jul. 10, 2006.
STN Registry Database, RN 894162-80-2, entered Jul. 18, 2006.
STN Registry Database, RN 894305-60-3, entered Jul. 19, 2006.
STN Registry Database, RN 895052-18-3, entered Jul. 23, 2006.
STN Registry Database, RN 903047-29-0, entered Aug. 21, 2006.
STN Registry Database, RN 904139-33-9, entered Aug. 24, 2006.
STN Registry Database, RN 904203-99-2, entered Aug. 24, 2006.

COMPOSITIONS AND METHODS FOR MODULATING HAIR GROWTH

RELATED APPLICATIONS

This application is a continuation of U.S. application Ser. No. 17/847,980, filed Jun. 23, 2022, which is a continuation of U.S. application Ser. No. 17/584,091, filed Jan. 25, 2022, now U.S. Pat. No. 11,472,804, which is a continuation of U.S. application Ser. No. 16/627,630, filed Dec. 30, 2019, now U.S. Pat. No. 11,312,714, which is the 371 U.S. National-Stage application of PCT/US2018/040385, filed Jun. 29, 2018, which claims the benefit of U.S. Provisional Patent Application No. 62/527,775, filed on Jun. 30, 2017, and U.S. Provisional Patent Application No. 62/654,095, filed on Apr. 6, 2018. The contents of each of these applications is hereby incorporated by reference in its entirety.

BACKGROUND

Hair follicle stem cells (HFSCs) undergo successive rounds of quiescence (telogen) punctuated by brief periods of proliferation correlating with the start of the hair cycle (telogen-anagen transition). Proliferation or activation of HFSCs is well known to be a prerequisite for advancement of the hair cycle. Despite advances in treatment options, baldness and alopecia continue to be conditions that cannot be successfully treated in all individuals. Some of the existing treatments are inconvenient for users, others require surgical intervention or other invasive procedures. Additional therapies are needed.

SUMMARY OF THE INVENTION

In certain aspects, the present disclosure provides compounds of formula I or II:

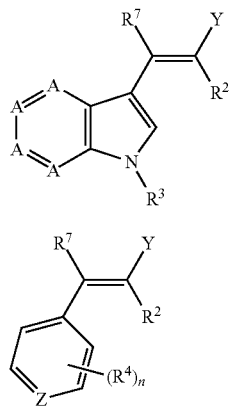

wherein:
each A is independently CH, $CR^4$, or N;
Y is carboxyl, ester, amide, or

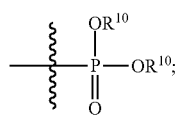

Z is CH, $CR^4$, or N.
$R^2$ is CN or carboxyl;
$R^3$ is H, aryl, aralkyl, or aralkylacyl, and is optionally substituted by one or more $R^5$, wherein
  each $R^5$ is independently selected from alkyl, alkoxy, or halo;
each instance of $R^4$ is independently alkyl, carboxyl, halo, hydroxy, ester, or CN;
$R^6$ is from H, alkyl, or cycloalkyl;
$R^7$ is hydrogen, alkyl, halo, hydroxyl, alkoxy, or acyloxy;
$R^{10}$ is hydrogen or alkyl; and
n is 0-4;
or a pharmaceutically acceptable salt thereof.

In certain embodiments, the present disclosure provides compounds of formula III:

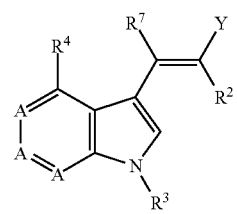

wherein:
Y is carboxyl, ester, amide, or

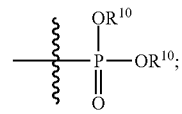

$R^2$ is CN or carboxyl;
$R^3$ is H, aryl, aralkyl, or aralkylacyl, and is optionally substituted by one or more $R^5$, wherein
  each $R^5$ is independently selected from alkyl, alkoxy, or halo;
each instance of $R^4$ is independently alkyl, carboxyl, halo, hydroxy, ester, or CN;
$R^6$ is from H, alkyl, or cycloalkyl; and
$R^7$ is hydrogen, alkyl, halo, hydroxyl, alkoxy, or acyloxy;
$R^{10}$ is hydrogen or alkyl;
$R^{11}$ is hydrogen or alkyl; and
n is 0-4;
or a pharmaceutically acceptable salt thereof.

In certain embodiments, the present disclosure provides compounds of formula V, VI, or VII:

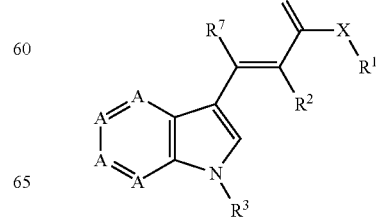

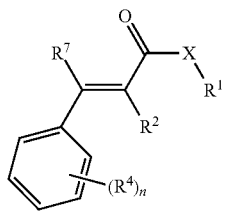
(VI)

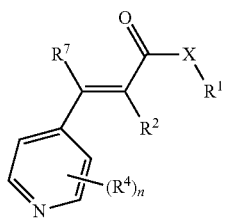
(VII)

wherein:

each A is independently CH, CR⁴, or N;

X is NR⁶ or O;

R¹ is H or lower alkyl; or either R¹ and R⁶ or R¹ and R², together with the atoms that separate them, complete a heterocycle;

R² is CN or carboxyl;

R³ is H, aryl, aralkyl, or aralkylacyl, and is optionally substituted by one or more R⁵, wherein
  each R⁵ is independently selected from alkyl, alkoxy, and halo;

each instance of R⁴ is independently alkyl, carboxyl, halo, hydroxy, or CN;

R⁶ is from H, alkyl, or cycloalkyl; and

R⁷ is hydrogen, alkyl, halo, hydroxyl, alkoxy, or acyloxy;

or a pharmaceutically acceptable salt thereof.

In certain embodiments, the present disclosure provides compounds of formula Va, VIa, or VIIa:

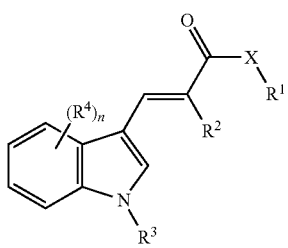
(Va)

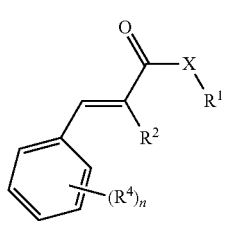
(VIa)

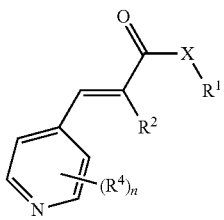
(VIIa)

wherein:

X is NR⁶ or O;

R¹ is H or lower alkyl;

R² is CN or carboxyl; or R¹ and R², together with the atoms that separate them, complete a heterocycle;

R³ is H, phenyl, or benzyl, and is optionally substituted by one or more R, wherein each R³ is independently selected from alkyl, alkoxy, or halo;

each instance of R⁴ is independently selected from alkyl, carboxyl, halo, hydroxy, or CN; and R⁶ is selected from H, alkyl, or cycloalkyl;

and pharmaceutically acceptable salts thereof.

In certain aspects, the present disclosure provides a pharmaceutical composition comprising a compound of the present disclosure and a pharmaceutically acceptable excipient.

In certain aspects, the present disclosure provides methods of enhancing lactate production in a cell, comprising contacting the cell with a compound or composition of the disclosure.

In certain aspects, the present disclosure provides methods of inhibiting mitochondrial pyruvate oxidation in a cell, comprising contacting the cell with a mitochondrial pyruvate oxidation (MPO) inhibitor, such as a compound of the present disclosure. In certain embodiments, the MPO inhibitor is a mitochondrial pyruvate carrier (MPC) inhibitor. In certain embodiments, inhibiting mitochondrial pyruvate oxidation in a cell has the effect of enhancing lactate production in a cell and/or enhancing the activity of LDH in a cell, and promoting hair growth, as described herein.

In certain aspects, the present disclosure provides methods of enhancing lactate production in a cell, comprising contacting the cell with an MPO inhibitor, such as a compound of the present disclosure. In certain embodiments, the MPO inhibitor is a mitochondrial pyruvate carrier (MPC) inhibitor.

In certain aspects, the present disclosure provides methods of enhancing the activity of LDH in a cell, comprising contacting the cell with an MPO inhibitor, such as a compound of the present disclosure. In certain embodiments, the MPO inhibitor is a mitochondrial pyruvate carrier (MPC) inhibitor.

In certain aspects, the present disclosure provides methods of enhancing the activity of lactic acid dehydrogenase (LDH) in a cell, comprising contacting the cell with an MPO inhibitor, such as a compound of the present disclosure. In certain embodiments, the MPO inhibitor is a mitochondrial pyruvate carrier (MPC) inhibitor. In certain aspects, the present disclosure provides methods of promoting hair growth or treating a hair growth condition or disorder such as baldness or alopecia, comprising administering to a patient a compound or composition as disclosed herein.

In certain aspects, the present disclosure provides methods of promoting hair growth or treating a hair growth condition or disorder such as baldness or alopecia, comprising administering to a patient an MPO inhibitor (e.g., topically, such as with a pharmaceutical composition formulated for topical application), such as a compound of the present disclosure. In certain embodiments, the present disclosure provides methods of promoting hair growth or treating a hair growth condition or disorder such as baldness or alopecia, comprising administering to a patient an MPC inhibitor (e.g., topically, such as with a pharmaceutical composition formulated for topical application), such a compound of the present disclosure. In certain embodiments, inhibiting mitochondrial pyruvate oxidation or the mitochondrial pyruvate carrier in a cell has the effect of enhancing lactate production and/or enhancing the activity of LDH in a cell, and promoting hair growth, as described herein.

BRIEF DESCRIPTION OF THE DRAWINGS

FIG. 1A: IHC staining for Ldha expression across the hair cycle shows Ldha protein confined to the HFSC niche, the bulge, indicated by the bracket. IHC staining for Sox9 on serial sections demarcates the HFSC population. Scale bar indicates 20 micrometers.

FIG. 2A: IHC with antibody recognizing specifically Ldha (same as used in FIG. 1A). bottom, IHC with antibody recognizing multiple isoforms of Ldh protein. Scale bars indicate 20 micrometers. FIG. 2B: the sorting strategy employed to isolate two populations of cells from the bulge. This particular sort was used to isolate the protein samples shown by western blot in FIG. 1B. FIG. 2C: Validation of colorimetric Ldh enzyme activity assay. The highest Ldh enzyme activity was observed in HFSC bulge and in the muscle. Activity indicated by purple stain; pink color is nuclear fast red counterstain. In absence of substrate lactate there was no detectable activity (purple stain). right, Additional validation of colorimetric Ldh enzyme activity assay. Enzyme activity inhibited by treating skin with HCl before addition of staining solution with substrate lactate. No Ldh activity (purple stain) detected. Skin in which enzyme activity is not inhibited by Hydrochloric Acid (HCl) shows highest Ldh enzyme activity in HFSC bulge and in the muscle. Scale bars indicate 50 micrometers.

FIG. 3A: GSEA on RNA-seq transcriptome data from HFSCs versus total epidermis shows enrichment for Glycolysis related genes in HFSCs (NES=1.72). FIG. 3B: GSEA on microarray transcriptome data from HFSCs versus total epidermis shows enrichment for Glycolysis related genes in HFSCs (NES=1.45). Results were generated from three mice of each condition. FIG. 3C: RNA-seq data from HFSCs sorted during telogen or telogen-anagen transition show induction of Ldha[21]. Data represent the average of three separate animals at each timepoint. FIG. 3D: Ldh activity in sorted stem cell populations, measured using a plate reader-based assay, shows elevated Ldh activity as stem cells become activated in telogen to anagen transition (Tel-Ana). Each bar represents the average signal for each condition where n=9 mice pooled from 3 independent experiments. Shown as mean±SEM. Paired t-test was performed, p<0.05. FIG. 3E: Heatmap showing relative levels of glycolytic and TCA cycle metabolites extracted from quiescent (Telogen, day 50), activated (Telogen-Anagen, day 70) and HFSCs that have returned to the quiescent state (Anagen, day 90). Data shown were generated from n=3 animals per timepoint in 3 independent experiments.

FIG. 4A: Analysis of RNA-seq data to validate that HFSCs in telogen-anagen transition were in fact in such a transition. The telogen-anagen transition is known to be driven by Shh (Gli factors are targets) and Wnt (Lef1, Axin, Ccnd1 are targets) signaling, and correlate with increased proliferation (Ki67 and Pcna). In addition, Sox4 was previously identified as a regulator of the telogen-anagen transition. n=3 mice per timepoint. Shown as mean±SEM. Paired t-test was performed, p<0.05. FIG. 4B: staining for Ki-67 marks dividing cells during various stages of the hair cycle. Brackets indicate the HFSC niche. Scale bars indicate 100 micrometers.

FIG. 5A: Mpc1fl/fl animals show pigmentation and hair growth, consistent with entry into the anagen cycle at 8.5 weeks, whereas Mpc1+/+ animals do not show dorsal pigmentation and hair growth this early. Animals shown are representative of at least 12 animals of each genotype. FIG. 5B: FACS isolation of HFSC bulge populations in Mpc1+/+ versus Mpc1fl/fl mice followed by western blotting shows successful deletion of Mpc1 protein in the stem cell niche. R-actin is a loading control. FIG. 5C: Plate reader assay for Ldh activity on sorted HFSC populations shows elevated activity in Mpc1fl/fl HFSCs compared to Mpc1+/+ HFSCs. Each bar represents the average signal for each genotype where n=9 mice pooled from 3 independent experiments. Shown as mean±SEM. Paired t-test was performed, p<0.05. FIG. 5D: Histology on WT versus Mpc1 deletion skin shows induction of anagen in absence of Mpc1. Scale bars indicate 100 micrometers. Quantification of phenotype at right shows percentage of dorsal follicles in telogen, telogen to anagen transition and anagen in Mpc1+/+ mice versus Mppc1fl/fl mice (n=250 follicles from 3 mice per genotype). Shown as mean±SEM. Paired t-test was performed, p<0.05. FIG. 5E: Immunohistochemistry staining for Ki-67, a marker of proliferation that is only active in HFSCs at the beginning of a new hair cycle, is only present in Mpc1fl/fl HFSCs at 8.5 weeks, consistent with their accelerated entry into a new hair cycle. Phospo-S6, another marker that is only active in HFSCs at the beginning of a new hair cycle, is only present in Mpc1fl/fl HFSCs. Staining for Sox9 shows that HFSCs are present in Mpc1 deleted niche. Images taken at 60× magnification. FIG. 5F: Deletion of Mpc1 in mice bearing the Lgr5CreER allele shows strong induction of the hair cycle. Note that red boxes indicate areas of new hair growth. Results are representative of at least 9 animals per genotype. FIG. 5G: Quantification of pigmentation in the indicated genotypes across three independent litters (n=5 mice per genotype).

FIG. 6A: Six months after initiation of deletion of Mpc1 in HFSCs (KJ5CrePR;Mpc1fl/fl), mice lacking Mpc1 show no deleterious effects as measured by the hair cycle (left), pathology (middle, H and E), or staining for HFSCs (right, Sox9). Scale bars indicate 100 micrometers in middle panel, and 50 micrometers in right panel. Images are representative of at least 12 animals per genotype. FIG. 6B: To demonstrate that the deletion of Mpc1 promotes proliferation specifically in HFSCs, we used K15CrePR;Ldha$^{fl/fl}$ mice bearing a lox-stop-lox-Tomato allele to look at K15+ HFSCs and proliferation with and without Mpc1 deletion (left). In addition, we took advantage of the ires-GFP within the LgrKCreER allele to stain for Ki-67 and GFP and look for co-localization with and without Mpc1 deletion (right). White brackets denote bulge area. Scale bars represent 20 micrometers. FIG. 6C: Deletion of Mpc1 in mice bearing the Lgr6CreER allele shows no premature induction of the hair cycle. FIG. 6D: Ldh activity assay on sorted HFSCs from either control or Lgr6CreER mediated Mpc1 deletion mice showed increased activity in cells lacking Mpc1. n=6 mice per genotype pooled from 2 independent experiments. Shown as mean±SEM. Paired t-test was performed, p<0.05.

FIG. 7A: Animals treated topically with UK-5099 (20 µM) show pigmentation and hair growth, indicative of entry into anagen, after 8 days of treatment. Full anagen, indicated by full coat of hair, is achieved after 14 days of treatment. Mice treated topically with vehicle control do not show pigmentation nor hair growth even after 12 days of treatment. right, Skin pathology showing that UK-5099 animals enter an accelerated anagen at 8 weeks typified by down growth of the follicle and hypodermal thickening, while vehicle control treated animals showed neither and remained in telogen. Images shown are representative of at least 14 mice from 7 independent experiments. Scale bars indicate 100 micrometers. FIG. 7B: Graph showing time to observed phenotype in vehicle versus UK-5099 treated mice. n=6 mice per condition. Shown as mean±SEM. FIG. 7C: Ldh enzyme activity assay in the epidermis shows strong activity in HFSCs in vehicle control and UK-5099 treated animals. Ldh enzyme activity also seen in interfollicular epidermis of UK-5099 treated animals. Ldh activity is indicated by purple stain; pink is nuclear fast red counterstain. Scale bars indicate 50 micrometers. FIG. 7D: Metabolomic analysis of Lactate on HFSCs isolated from UK-5099 treated skin for 48 hours; Each bar represents the average signal for each condition where n=9 mice pooled from 3 independent experiments. Shown as mean±SEM. Paired t-test was performed, p<0.05.

DETAILED DESCRIPTION OF THE INVENTION

Figure 1A:
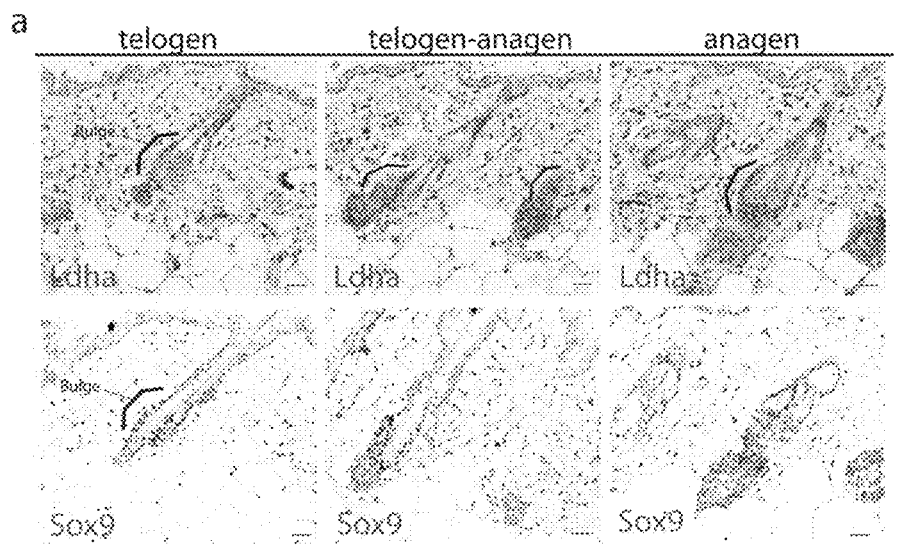
FIGS. 1A-IE show Lactate dehydrogenase activity is enriched in HFSCs.

In certain aspects, the present disclosure provides compounds of formula I or II:

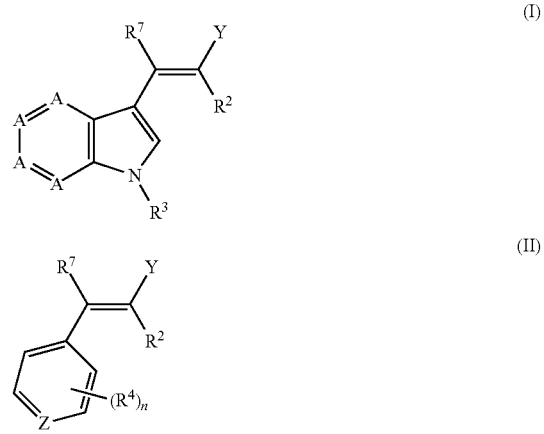

wherein:
each A is independently CH, CR$^4$, or N;
Y is carboxyl, ester, amide, or

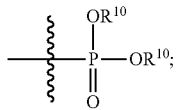

Z is CH, CR$^4$, or N.
R$^2$ is CN or carboxyl;
R$^3$ is H, aryl, aralkyl, or aralkylacyl, and is optionally substituted by one or more R$^5$, wherein
  each R$^5$ is independently selected from alkyl, alkoxy, or halo;
each instance of R$^4$ is independently alkyl, carboxyl, halo, hydroxy, ester, or CN;
R$^6$ is from H, alkyl, or cycloalkyl;
R$^7$ is hydrogen, alkyl, halo, hydroxyl, alkoxy, or acyloxy;
R$^{10}$ is hydrogen or alkyl; and
n is 0-4;
or a pharmaceutically acceptable salt thereof.

In certain embodiments, the compound is a compound of formula I. In certain embodiments, the compound is a compound of formula II.

In certain embodiments of Formula I or II, Z is CH or N.

In certain embodiments, the present disclosure provides compounds of formula III or IV:

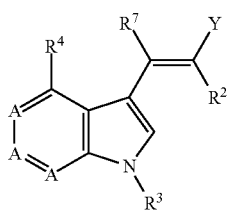
(III)

wherein,
Y is carboxyl, ester, amide, or

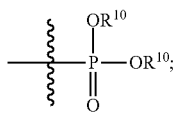

R$^2$ is CN or carboxyl;
R$^3$ is H, aryl, aralkyl, or aralkylacyl, and is optionally substituted by one or more R$^5$, wherein
  each R$^5$ is independently selected from alkyl, alkoxy, or halo;
each instance of R$^4$ is independently alkyl, carboxyl, halo, hydroxy, ester, or CN;
R$^6$ is from H, alkyl, or cycloalkyl; and
R$^7$ is hydrogen, alkyl, halo, hydroxyl, alkoxy, or acyloxy;
R$^{10}$ is hydrogen or alkyl;
R$^{11}$ is hydrogen or alkyl; and
n is 0-4;
or a pharmaceutically acceptable salt thereof.

In certain embodiments, the compound is a compound of formula III.

In certain embodiments of Formula I, II, and III, Y is wherein Y is

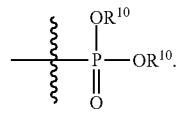

In certain embodiments, R$^{10}$ is H. In certain embodiments, R$^{10}$ is alkyl (e.g., ethyl). In certain embodiments Y is ester or amido.

In certain embodiments of Formula I, II, or III, R$^{11}$ is alkyl (e.g., methyl).

In certain embodiments, the present disclosure provides compounds of formula V, VI, or VII:

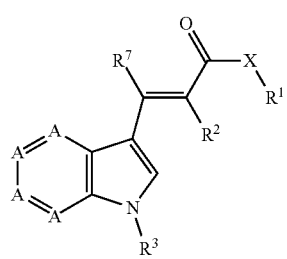
(V)

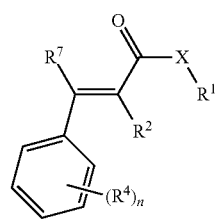
(VI)

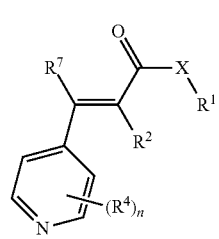
(VII)

wherein:
each A is independently CH, CR$^4$, or N;
X is NR$^6$ or O;
R$^1$ is H or lower alkyl; or either R$^1$ and R$^6$ or R$^1$ and R$^2$, together with the atoms that separate them, complete a heterocycle;
R$^2$ is CN or carboxyl;
R$^3$ is H, aryl, aralkyl, or aralkylacyl, and is optionally substituted by one or more R$^5$, wherein
  each R$^5$ is independently selected from alkyl, alkoxy, and halo;
each instance of R$^4$ is independently alkyl, carboxyl, halo, hydroxy, or CN;
R$^6$ is from H, alkyl, or cycloalkyl; and
R$^7$ is hydrogen, alkyl, halo, hydroxyl, alkoxy, or acyloxy;
or a pharmaceutically acceptable salt thereof.

In certain embodiments, the compound is a compound of formula V. In certain embodiments, the compound is a compound of formula VI. In certain embodiments, the compound is a compound of formula VII.

In certain embodiments of formula I, II, III, V, VI, or VII, at least one A is N, preferably no more than two occurrences of A are N. In certain preferred embodiments, exactly one A is N, preferably the A bound to the same carbon as $NR^3$.

In certain embodiments, the present disclosure provides compounds of formula Va, VIa, or VIIa:

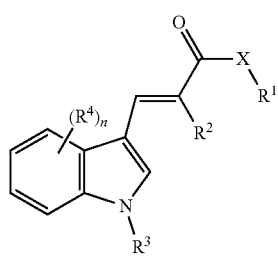

(Va)

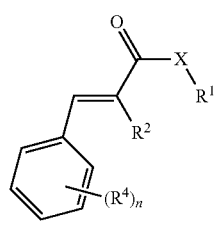

(VIa)

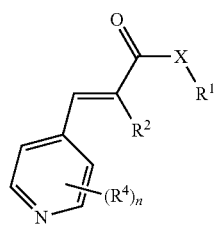

(VIIa)

wherein:
X is $NR^6$ or O;
$R^1$ is H or lower alkyl;
$R^2$ is CN or carboxyl; or $R^1$ and $R^2$, together with the atoms that separate them, complete a heterocycle;
$R^3$ is H, phenyl, or benzyl, and is optionally substituted by one or more $R^5$, wherein each $R^5$ is independently selected from alkyl, alkoxy, or halo;
each instance of $R^4$ is independently selected from alkyl, carboxyl, halo, hydroxy, or CN; and
$R^6$ is selected from H, alkyl, or cycloalkyl;
and pharmaceutically acceptable salts thereof.

In certain embodiments, the compound is a compound of formula Va. In certain embodiments, the compound is a compound of formula VIa. In certain embodiments, the compound is a compound of formula VIIa.

In certain embodiments of formula V, VI, VII, Va, VIa, or VIIa, X is NH. In certain embodiments, X is O.

In certain embodiments of formula V, VI, VII, Va, VIa, or VIIa, $R^1$ is H. In certain embodiments, $R^1$ is lower alkyl. In certain embodiments, R and $R^6$, together with the atoms that separate them, complete a heterocycle (e.g., morpholinyl).

In certain embodiments of formula V, VI, VII, Va, VIa, or VIIa, $R^6$ is hydrogen.

In certain embodiments of formula V, VI, VII, Va, VIa, or VIIa, $R^2$ is CN. In certain embodiments, $R^2$ is carboxyl. In certain embodiments, $R^1$ and $R^2$, together with the atoms that separate them, complete a heterocyclyl selected from thiazolidine-2,4-dion-5-ylidene or 2-iminothiazolidin-4-one-5-ylidene.

In certain embodiments of formula I, II, III, V, VI, VII, Va, VIa, or VIIa, $R^3$ is H. In certain embodiments, $R^3$ is phenyl. In certain embodiments, $R^3$ is phenyl and is substituted by one or more $R^5$. In certain embodiments, $R^3$ is substituted by one $R^5$, and wherein $R^5$ is an alkoxy. In certain embodiments, $R^3$ is aralkyl (e.g., benzyl or phenethyl). In certain embodiments, $R^3$ is aralkylacyl (e.g., phenylacetyl). In certain embodiments, $R^3$ is benzyl. In certain embodiments, $R^3$ is benzyl and is substituted by one or more $R^5$. In certain embodiments, $R^3$ is aralkyl (e.g., benzyl or phenethyl) and is substituted by one or more $R^5$ (preferably on the phenyl ring). In certain embodiments, $R^3$ is aralkylacyl (e.g., phenylacetyl), and is substituted by one or more $R^5$ (preferably on the phenyl ring). In certain embodiments, $R^3$ is substituted by one or two $R^5$, and wherein each $R^5$ is independently selected from fluoroalkyl or fluoro. In certain embodiments, $R^3$ is substituted by two $R^5$, and wherein each $R^5$ is trifluoromethyl.

In certain embodiments of formula Va, VIa, or VIIa, n is 0.

In certain preferred embodiments, the present disclosure provides compounds of formula Vb

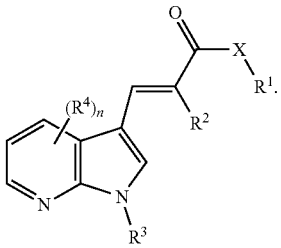

(Vb)

In certain embodiments, the present disclosure provides compounds of formula Vc

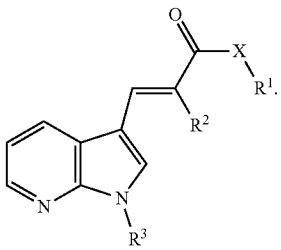

(Vc)

In certain embodiments of formula Va, VIa, VIIa, or Vb, n is 1.

In certain preferred embodiments, the present disclosure provides compounds of formula Vd (Vd)

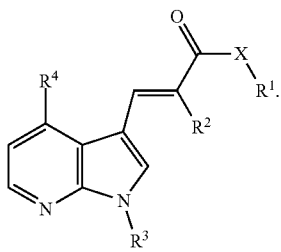

In certain embodiments, the present disclosure provides compounds of formula Ve (Ve)

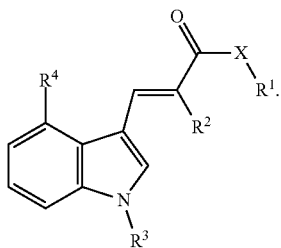

In certain embodiments of formula Vb, Vd or Ve, $R^4$ is selected from halo or haloalkyl. In certain preferred embodiments, $R^4$ is halo (e.g., chloro or bromo). In other preferred embodiments, $R^4$ is carboxyl or ester.

In certain embodiments of formula VI or VIa, n is 0. In certain embodiments, n is 2, and $R^4$ is selected from halo or haloalkyl.

In certain embodiments of formula I, II, III, V, VI, VII, Va, Vb, Vc, Vd, Ve, VIa, or VIIa, $R^7$ is hydrogen, hydroxyl, halo (e.g., chloro), or acyloxy (e.g., acetyloxy). In certain embodiments, $R^7$ is hydroxyl, halo (e.g., chloro), or acyloxy (e.g., acetyloxy).

In certain embodiments of formula I, II, III, V, VI, VII, Va, Vb, Vc, Vd, Ve, VIa, or VIIa, the compound is not JXL001.

In certain aspects, the compound of the disclosure is a compound of Table 1.

TABLE 1

Exemplary Compounds of the Present Invention

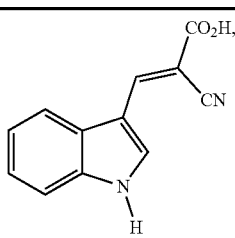 JXL002

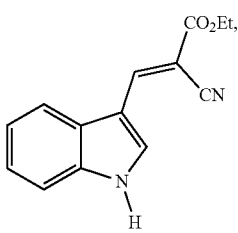 [SMILES: CCOC(=O)/C(C#N)=C/c1c[nH]c2ccccc12] JXL003

TABLE 1-continued

Exemplary Compounds of the Present Invention

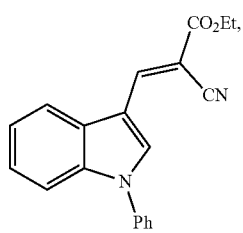 [SMILES: CCOC(=O)/C(C#N)=C/c1cn(-c2ccccc2)c2ccccc12] JXL004

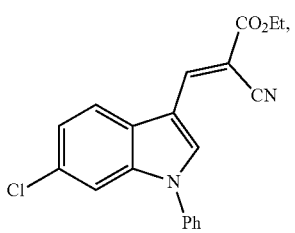 [SMILES: CCOC(=O)/C(C#N)=C/c1cn(-c2ccccc2)c2cc(Cl)ccc12] JXL005

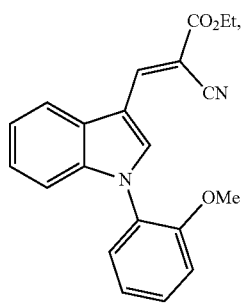 [SMILES: CCOC(=O)/C(C#N)=C/c1cn(-c2ccccc2OC)c2ccccc12] JXL006

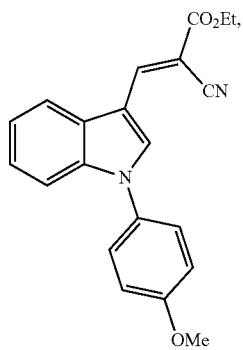 [SMILES: CCOC(=O)/C(C#N)=C/c1cn(-c2ccc(OC)cc2)c2ccccc12] JXL007

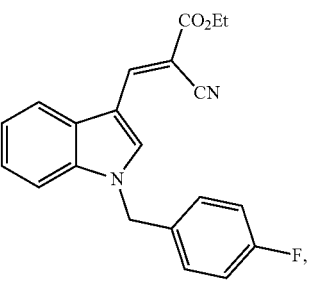 [SMILES: CCOC(=O)/C(C#N)=C/c1cn(Cc2ccc(F)cc2)c2ccccc12] JXL008

TABLE 1-continued
Exemplary Compounds of the Present Invention
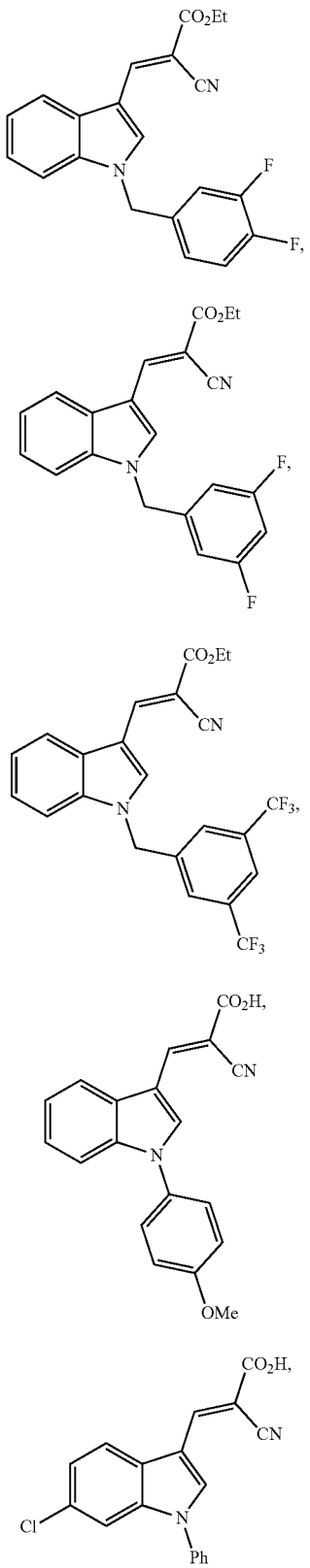
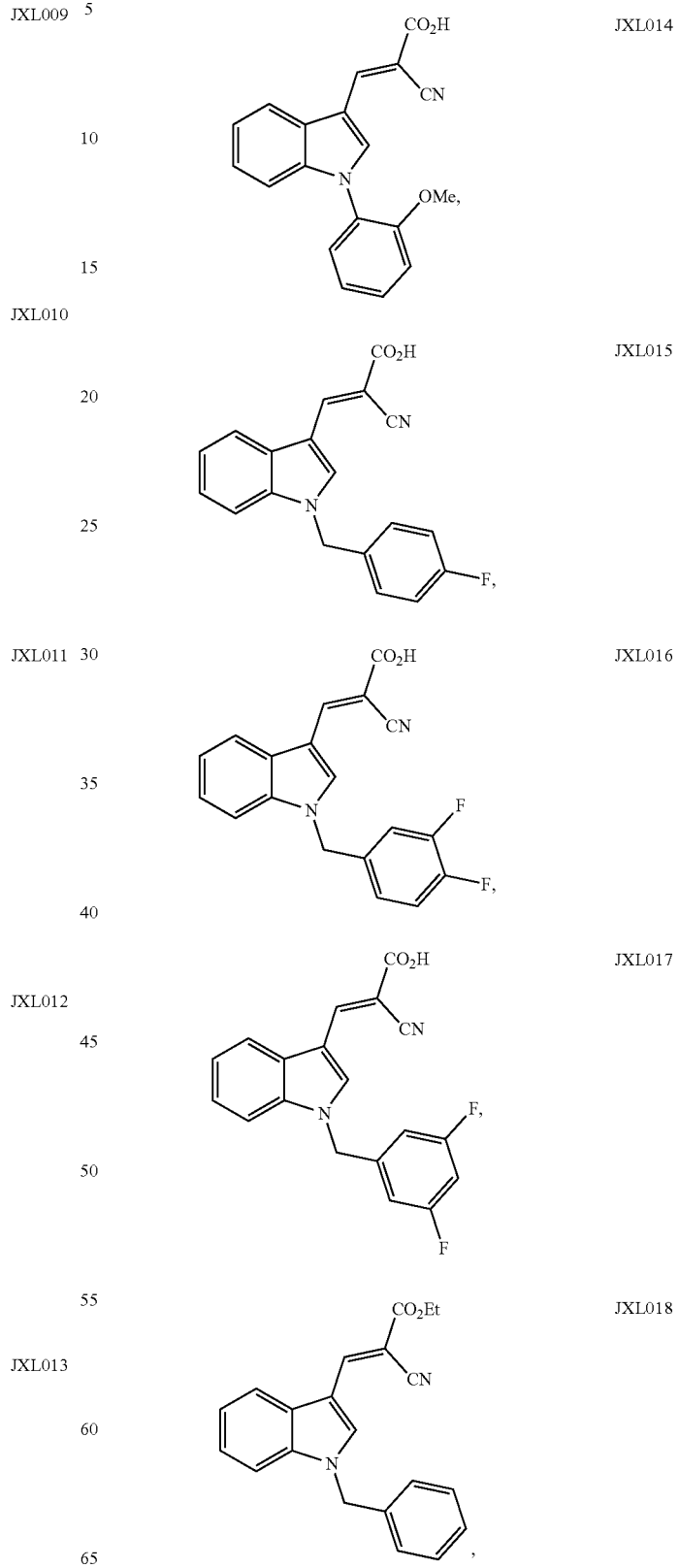

TABLE 1-continued
Exemplary Compounds of the Present Invention
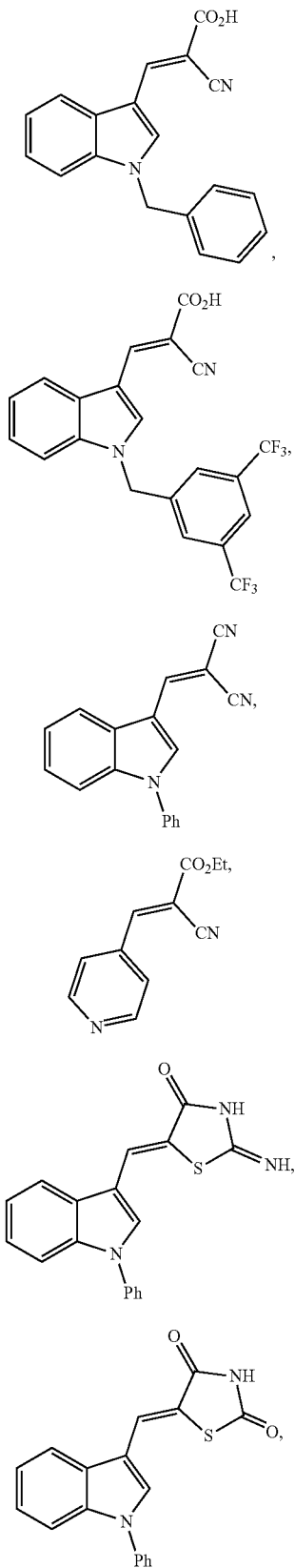
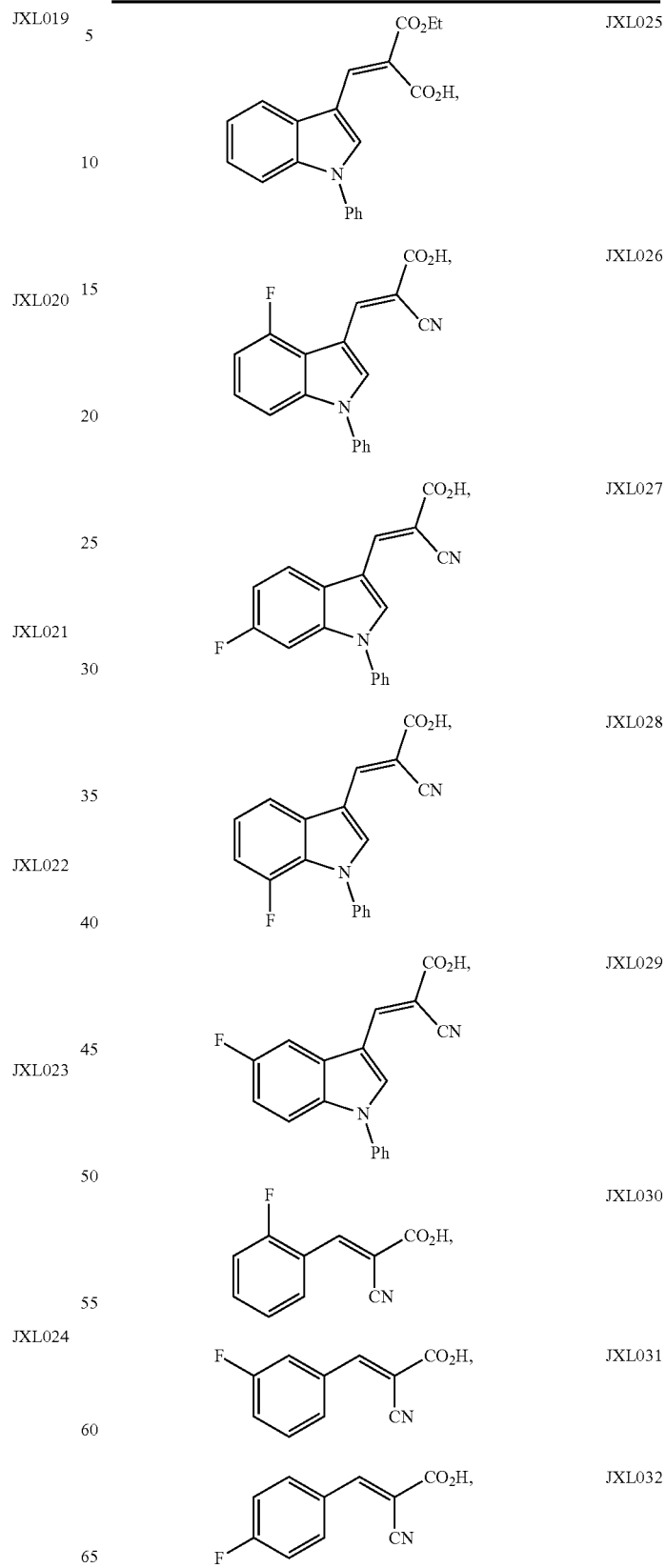

TABLE 1-continued

Exemplary Compounds of the Present Invention

| Structure | ID |
|---|---|
| 3-(CF₃)C₆H₄-CH=C(CN)-CO₂H | JXL033 |
| 4-(CF₃)C₆H₄-CH=C(CN)-CO₂H | JXL034 |
| 4-Cl, 1-Ph-indol-3-yl-CH=C(CN)-CO₂H | JXL035 |
| 5-F-1-(3,4-difluorobenzyl)-indol-3-yl-CH=C(CN)-CO₂H | JXL036 |
| 5-F-1-(3,5-difluorobenzyl)-indol-3-yl-CH=C(CN)-CO₂H | JXL037 |
| 5-F-1-(3,5-bis(trifluoromethyl)benzyl)-indol-3-yl-CH=C(CN)-CO₂H | JXL038 |
| 6-F-1-(3,4-difluorobenzyl)-indol-3-yl-CH=C(CN)-CO₂H | JXL039 |
| 6-F-1-(3,5-difluorobenzyl)-indol-3-yl-CH=C(CN)-CO₂H | JXL040 |
| 6-F-1-(3,5-bis(trifluoromethyl)benzyl)-indol-3-yl-CH=C(CN)-CO₂H | JXL041 |
| 3-F-4-Me-C₆H₃-CH=C(CN)-CO₂H | JXL042 |
| 3,4-diF-C₆H₃-CH=C(CN)-CO₂H | JXL043 |
| 2,4-diF-C₆H₃-CH=C(CN)-CO₂H | JXL044 |
| 3,5-bis(CF₃)-C₆H₃-CH=C(CN)-CO₂H | JXL045 |

TABLE 1-continued

Exemplary Compounds of the Present Invention

| Structure | ID |
|---|---|
| 2-cyano-3-(2-chloro-3-trifluoromethylphenyl)acrylic acid | JXL046 |
| 2-cyano-3-(4-fluoro-3-trifluoromethylphenyl)acrylic acid | JXL047 |
| 2-cyano-3-phenylacrylic acid | JXL048 |
| 2-cyano-3-(4-hydroxyphenyl)acrylic acid | JXL049 |
| 2-cyano-3-[4-chloro-1-(3,5-bis(trifluoromethyl)benzyl)-1H-indol-3-yl]acrylic acid | JXL050 |
| 2-cyano-3-[4-bromo-1-(3,5-bis(trifluoromethyl)benzyl)-1H-indol-3-yl]acrylic acid | JXL051 |
| 2-cyano-3-[4-fluoro-1-(3,5-bis(trifluoromethyl)benzyl)-1H-indol-3-yl]acrylic acid | JXL052 |
| 2-cyano-3-[7-fluoro-1-(3,5-bis(trifluoromethyl)benzyl)-1H-indol-3-yl]acrylic acid | JXL053 |
| 2-cyano-3-[5-chloro-1-(3,5-bis(trifluoromethyl)benzyl)-1H-indol-3-yl]acrylic acid | JXL054 |
| 2-cyano-3-[4-cyano-1-(3,5-bis(trifluoromethyl)benzyl)-1H-indol-3-yl]acrylic acid | JXL055 |
| 2-cyano-3-[4-carboxy-1-(3,5-bis(trifluoromethyl)benzyl)-1H-indol-3-yl]acrylic acid | JXL056 |

TABLE 1-continued
Exemplary Compounds of the Present Invention
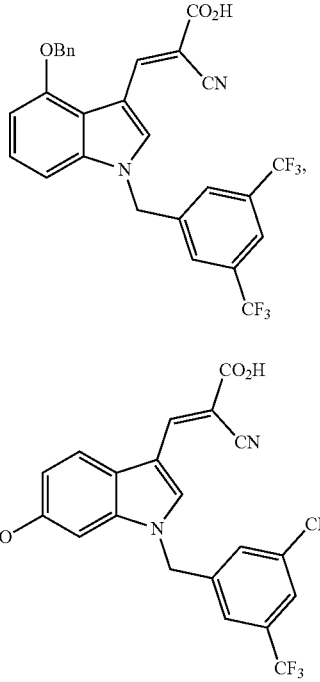 JXL057
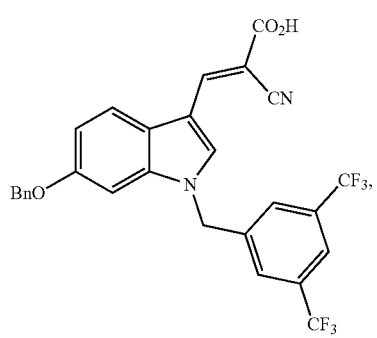 [SMILES: N#C/C(=C\c1cn(Cc2cc(C(F)(F)F)cc(C(F)(F)F)c2)c2cc(OCc3ccccc3)ccc12)C(=O)O] JXL058
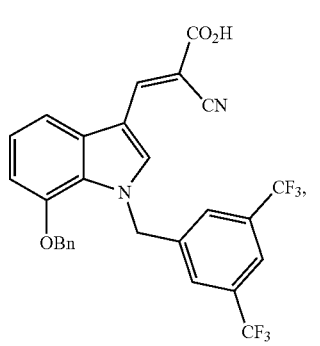 [SMILES: N#C/C(=C\c1cn(Cc2cc(C(F)(F)F)cc(C(F)(F)F)c2)c2c(OCc3ccccc3)cccc12)C(=O)O] JXL059
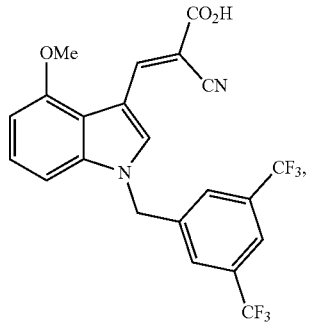 [SMILES: COc1cccc2c1c(/C=C(\C#N)C(=O)O)cn2Cc1cc(C(F)(F)F)cc(C(F)(F)F)c1] JXL060
TABLE 1-continued
Exemplary Compounds of the Present Invention
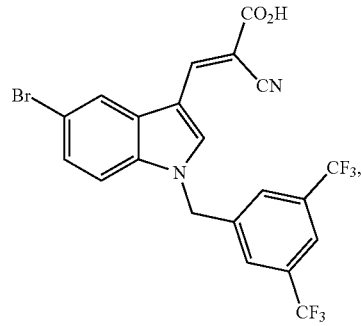 JXL061
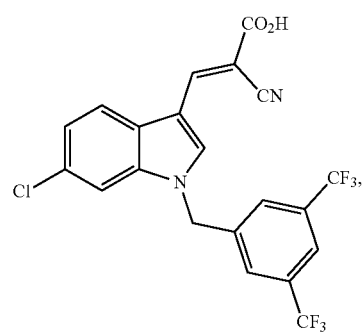 [SMILES: N#C/C(=C\c1cn(Cc2cc(C(F)(F)F)cc(C(F)(F)F)c2)c2cc(Cl)ccc12)C(=O)O] JXL062
JXL063
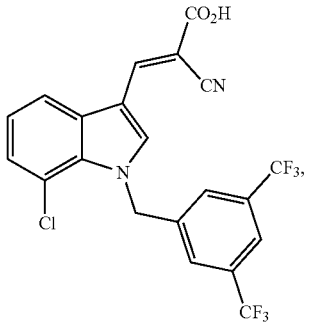 [SMILES: N#C/C(=C\c1cn(Cc2cc(C(F)(F)F)cc(C(F)(F)F)c2)c2c(Cl)cccc12)C(=O)O] JXL064

TABLE 1-continued
Exemplary Compounds of the Present Invention
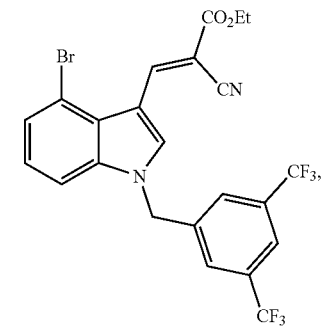
JXL065
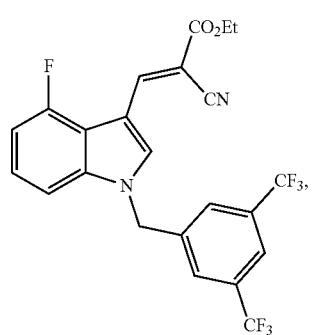
JXL066
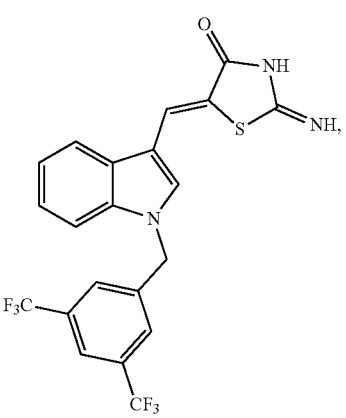 [SMILES: N=C1NC(=O)/C(=C/c2cn(Cc3cc(C(F)(F)F)cc(C(F)(F)F)c3)c3ccccc23)S1]
JXL067
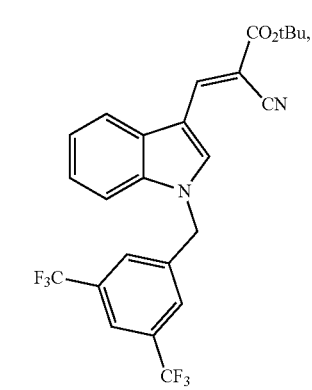 [SMILES: CC(C)(C)OC(=O)/C(C#N)=C/c1cn(Cc2cc(C(F)(F)F)cc(C(F)(F)F)c2)c2ccccc12]
JXL068
TABLE 1-continued
Exemplary Compounds of the Present Invention
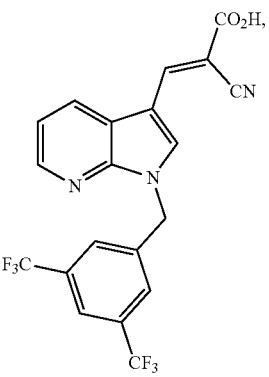
JXL069
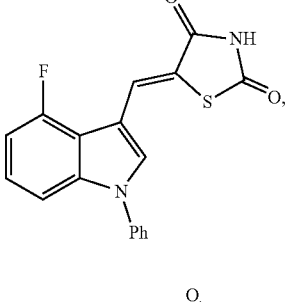
JXL070
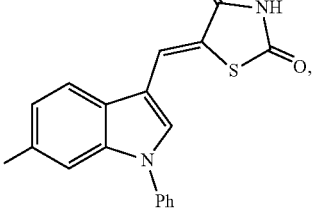
JXL071
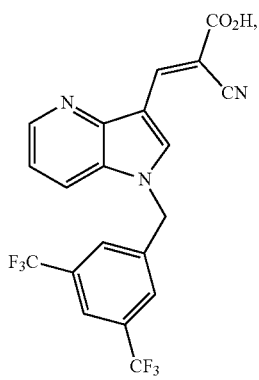 [SMILES: N#C/C(=C\c1cn(Cc2cc(C(F)(F)F)cc(C(F)(F)F)c2)c2cccnc12)C(=O)O]
JXL072

TABLE 1-continued

Exemplary Compounds of the Present Invention

| Structure | ID |
|---|---|
| (3-((1-(3,5-bis(trifluoromethyl)benzyl)-1H-pyrrolo[2,3-c]pyridin-3-yl)methylene)-2-cyanoacrylic acid) | JXL073 |
| 5-benzylidenethiazolidine-2,4-dione | JXL074 |
| 5-((1H-indol-3-yl)methylene)thiazolidine-2,4-dione | JXL075 |
| 3-(1-(3,5-bis(trifluoromethyl)benzyl)-4-chloro-1H-pyrrolo[2,3-b]pyridin-3-yl)-2-cyanoacrylic acid | JXL076 |
| 3-(1-(3,5-bis(trifluoromethyl)benzyl)-4-bromo-1H-pyrrolo[2,3-b]pyridin-3-yl)-2-cyanoacrylic acid | JXL077 |
| methyl 3-(1-(3,5-bis(trifluoromethyl)benzyl)-1H-indol-3-yl)-2-cyanoacrylate | JXL078 |
| 3-(1-(3,5-bis(trifluoromethyl)phenethyl)-1H-indol-3-yl)-2-cyanoacrylic acid | JXL079 |
| ethyl 3-(1-(2-(3,5-bis(trifluoromethyl)phenyl)acetyl)-1H-indol-3-yl)-2-cyanoacrylate | JXL080 |
| (E)-3-(1-(3,5-bis(trifluoromethyl)benzyl)-1H-indol-3-yl)-2-cyano-1-morpholinoprop-2-en-1-one | JXL081 |

TABLE 1-continued

Exemplary Compounds of the Present Invention

| Compound | ID |
|---|---|
| (structure with 7-azaindole, CH=C(CO2Et)(CN), N-CH2-3,5-bis(CF3)phenyl) | JXL082 |
| (structure with indole, C(OH)=C(CO2Et)(CN), N-CH2-3,5-bis(CF3)phenyl) | JXL083 |
| (structure with indole, C(OAc)=C(CO2Et)(CN), N-CH2-3,5-bis(CF3)phenyl) | JXL084 |
| (structure with indole, C(Cl)=C(CO2Et)(CN), N-CH2-3,5-bis(CF3)phenyl) | JXL085 |
| (structure with indole, CH=C(P(O)(OEt)2)(CN), N-CH2-3,5-bis(CF3)phenyl) | JXL086 |
| (structure with 4-chloro-7-azaindole, CH=C(CO2Et)(CN), N-CH2-3,5-bis(CF3)phenyl) | JXL087 |
| (structure with 4-bromo-7-azaindole, CH=C(CO2Et)(CN), N-CH2-3,5-bis(CF3)phenyl) | JXL088 |
| (structure with 5-chloroindole, CH=C(CO2Et)(CN), N-CH2-3,5-bis(CF3)phenyl) | JXL089 |

TABLE 1-continued

Exemplary Compounds of the Present Invention

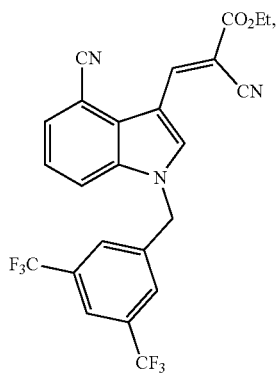 [SMILES: CCOC(=O)/C(C#N)=C/c1cn(Cc2cc(C(F)(F)F)cc(C(F)(F)F)c2)c2cccc(C#N)c12]
JXL090

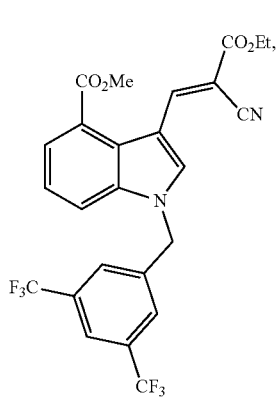
JXL091

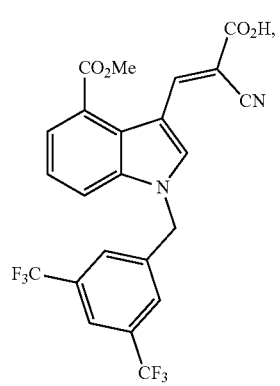 [SMILES: CCOC(=O)/C(C#N)=C/c1cn(Cc2cc(C(F)(F)F)cc(C(F)(F)F)c2)c2cccc(C(=O)OC)c12]
JXL092

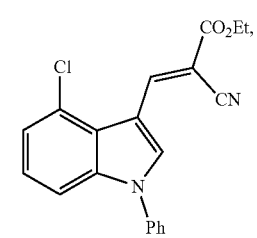 [SMILES: CCOC(=O)/C(C#N)=C/c1cn(-c2ccccc2)c2cccc(Cl)c12]
JXL093

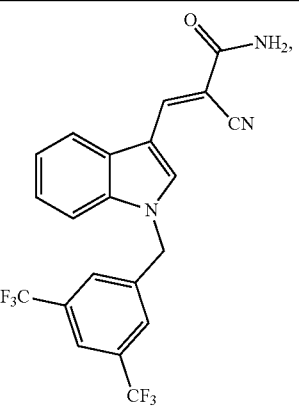
JXL094

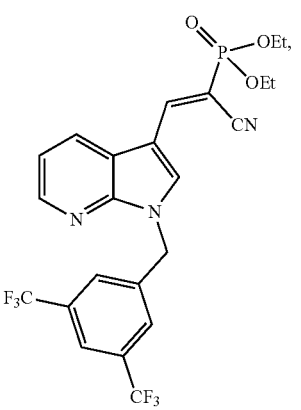 [SMILES: CCOP(=O)(OCC)/C(C#N)=C/c1cn(Cc2cc(C(F)(F)F)cc(C(F)(F)F)c2)c2ncccc12]
JXL095 and

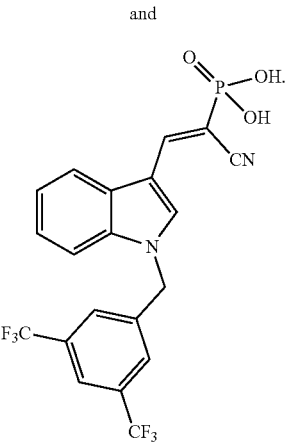
JXL096

In certain aspects, the present disclosure provides a pharmaceutical composition comprising a compound of the present disclosure and a pharmaceutically acceptable excipient. In certain embodiments, the pharmaceutical composition is formulated for topical administration.

In certain aspects, the present disclosure provides methods of enhancing lactate production in a cell, comprising contacting the cell with a compound or composition of the disclosure. In certain embodiments, the cell is a hair follicle stem cell.

In certain aspects, the present disclosure provides methods of promoting hair growth or treating hair growth conditions or disorders such as baldness or alopecia, comprising administering to a patient a compound or composition as disclosed herein.

In certain aspects, the present disclosure provides methods of enhancing lactate production in a cell, comprising contacting the cell with a mitochondrial pyruvate carrier (MPC) inhibitor. In certain embodiments, the MPC is MPC1.

In certain aspects, the present disclosure provides methods of promoting hair growth or treating a hair growth condition or disorder such as baldness or alopecia, comprising administering to a patient a mitochondrial pyruvate carrier (MPC) inhibitor (e.g., topically, such as with a pharmaceutical composition formulated for topical application). In certain embodiments, the MPC is MPC1.

In certain aspects, the present disclosure provides methods of inhibiting mitochondrial pyruvate oxidation in a cell, comprising contacting the cell with a mitochondrial oxidation (MPO) inhibitor.

In certain aspects, the present disclosure provides methods of promoting hair growth or treating a hair growth condition or disorder such as baldness or alopecia, comprising administering to a patient a mitochondrial oxidation (MPO) inhibitor (e.g., topically, such as with a pharmaceutical composition formulated for topical application).

In certain embodiments, the MPC or MPO inhibitor is a compound of the disclosure.

Discussion

Numerous studies have uncovered unique gene expression signatures in hair follicle stem cells (HFSCs) versus other follicle cells or cells of the interfollicular epidermis. Many of these signatures are regulated by transcription factors that were later shown to play important roles in HFSC homeostasis.

Lactate dehydrogenase is most commonly encoded by the Ldha and Ldhb genes in mammals, the protein products of which form homo- or hetero-tetramers to catalyze the NADH-dependent reduction of pyruvate to lactate and $NAD^+$-dependent oxidation of lactate to pyruvate. By immunostaining, it has been discovered that Ldha is enriched in quiescent HFSCs in situ (telogen) (FIG. 1A), and performing immunohistochemistry staining (IHC) with an antibody that recognizes both Ldha and Ldhb showed that only Ldha appears to be localized to the HFSC niche (FIG. 2A).

Figure 1B:
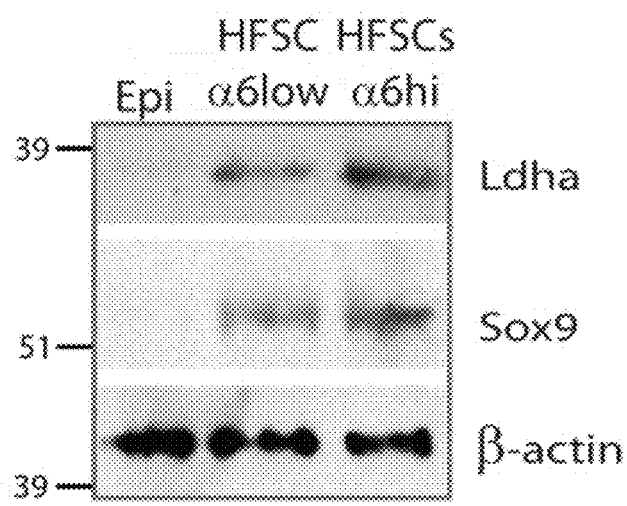
FIG. 1B: Immunoblotting on FACS-isolated HFSC populations (α6low/Cd34+ and α6hiCd34+) versus total epidermis (Epi) shows differential expression of Ldha in the stem cell niche. Sox9 is a marker of HFSCs, and β-actin is a loading control.
Figure 2A:
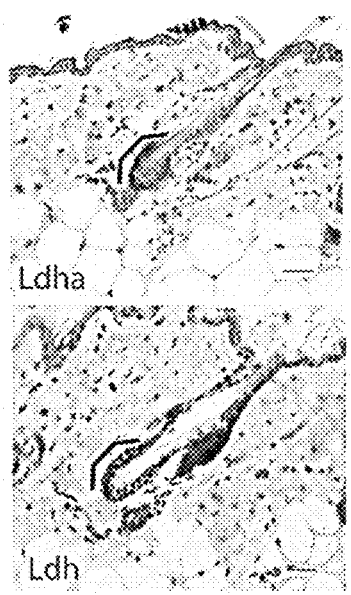
FIGS. 2A-2C show the validation of key reagents and assays.
Figure 2B:
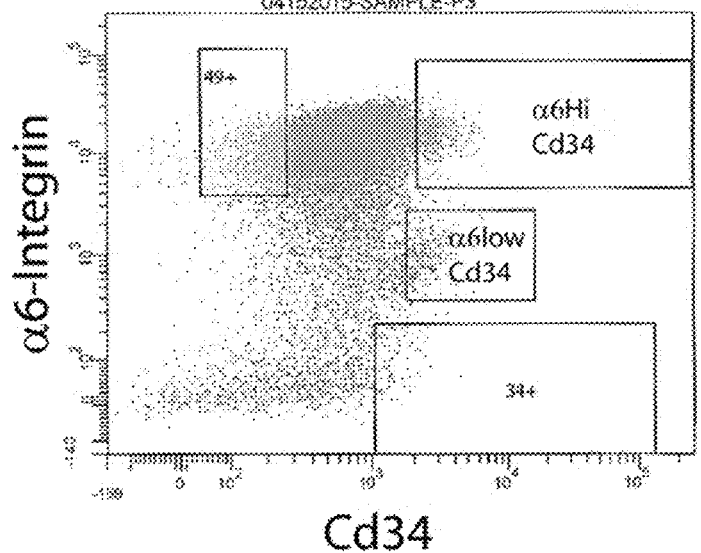

IHC analysis also showed Ldha expression was enriched in HFSCs (Sox9+) at three stages of the hair cycle (FIG. 1A). Consistently, immunoblotting of lysates from sorted cells showed strong expression of Ldha in the basal HFSCs (α6HiCD34+), and suprabasal (α6LoCD34+) HFSC populations relative to total epidermis (FIG. 1B) (Sorting strategy is outlined in FIG. 2B).

To determine whether Ldha expression patterns correlate with activity of the Ldh enzyme, a colorimetric-based enzymatic assay was used to assess Ldh activity capacity in situ. Typically performed on protein lysates or aliquots with a plate reader, the Ldh activity assay was adapted to work in situ on frozen tissue sections. Note that since both the in situ and in vitro Ldh activity assays employ use of excess substrate (lactate), the results from these assays reflect the capacity for Ldh activity, and not the steady-state activity.

Figure 1C:
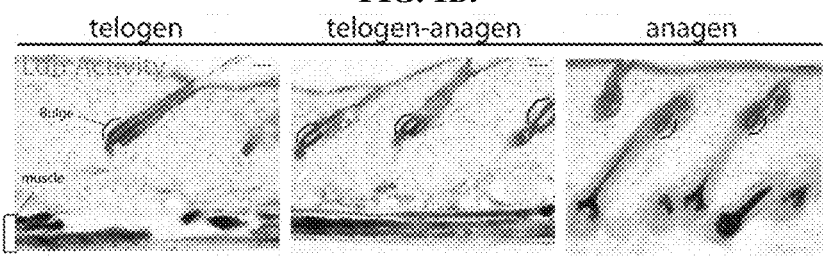
FIG. 1C: Colorimetric assay for Ldh enzyme activity in the epidermis shows highest activity in the bulge (brackets) and subcuticular muscle layer (bracket). This activity is enriched in the bulge across different stages of the hair cycle. Activity is indicated by purple color; pink is a nuclear counterstain. Note also that developing hair shafts in pigmented mice show strong deposits of melanin as observed here; hair shafts never displayed any purple stain indicative of Ldh activity. Scale bars indicate 50 micrometers.
Figure 1D:
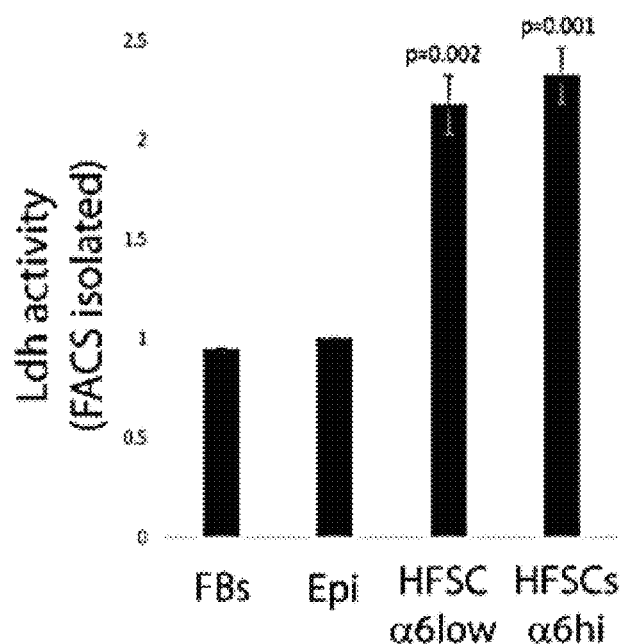
FIG. 1D: Ldh activity in sorted cell populations, measured using a plate reader-based assay, also shows the highest Ldh activity in two separate HFSC populations (α6hi/Cd34 and α6low/Cd34) compared to epidermal cells (Epi) and fibroblasts (FBs). Each bar represents the average signal for each cell type where n=9 mice pooled from 3 independent experiments. Shown as mean±SEM. Paired t-test was performed, p<0.05 shown for each cell type versus epidermal cells.
Figure 1E:
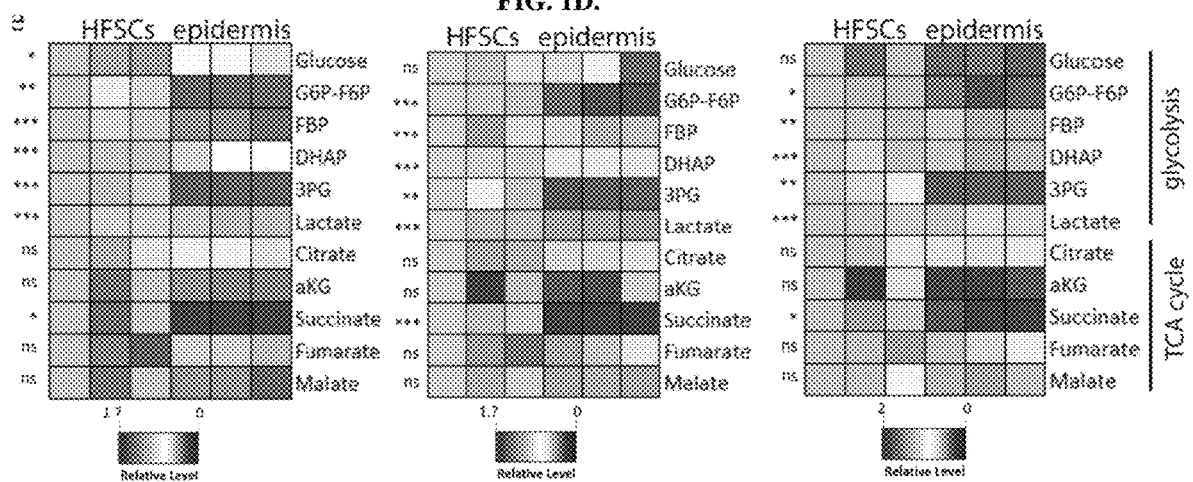
FIG. 1E: HFSCs and epidermal cells were isolated during telogen (day 50) by FACS, and metabolites were extracted and analyzed by LC-MS. Heatmaps show relative levels of glycolytic and TCA cycle metabolites from cells isolated from different mice in independent experiments with cells from three animals in each. Asterisks indicate significant difference in metabolite levels between epidermal cells and HFSCs. For e, paired t-test was performed; * denotes p<0.05,  denotes p<0.01, * denotes p<0.001, ns denotes p>0.05, and n=9 mice pooled from 3 independent experiments.
Figure 2C:
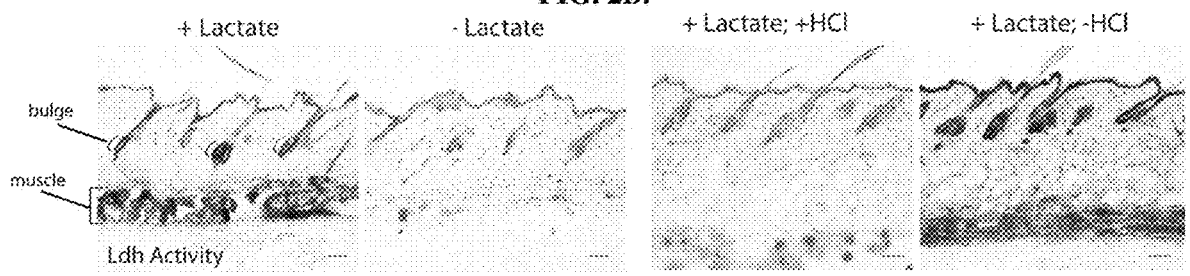

Applying this assay to skin samples demonstrated that Ldh activity capacity was significantly higher in HFSCs, consistent with the expression pattern of Ldha (FIG. 1C). Furthermore, Ldh activity was enriched in HFSCs across the hair cycle (FIG. 1C). As a control, assays conducted without the enzymatic substrate (lactate) or on acid-treated tissue yielded zero activity (FIG. 2C). To further validate these results, we sorted epidermal populations, generated cell lysates on the sorted cells, and performed a similar colorimetric-based enzymatic assay on the sorted cell lysates, which also showed increased Ldh activity in HFSCs (FIG. 1D). To better characterize the metabolism of HFSCs, we performed metabolomics analysis on sorted populations from mouse skin by liquid chromatography-mass spectrometry (LC-MS) (FIG. 1e). Several glycolytic metabolites, including glucose/fructose-6-phosphate, fructose-bisphosphate, dihydroxyacetone phosphate, 3-phosphoglycerate, and lactate, were routinely higher in HFSCs relative to total epidermis across three independent experiments (isolated from different mice on different days). Conversely, most TCA cycle metabolites were not consistently different between the epidermis and HFSCs (FIG. 1E). Collectively these results suggest that while all cells in the epidermis use the TCA cycle extensively to generate energy, HFSCs also have increased Ldha expression, Ldh activity, and glycolytic metabolism.

Figure 3A:
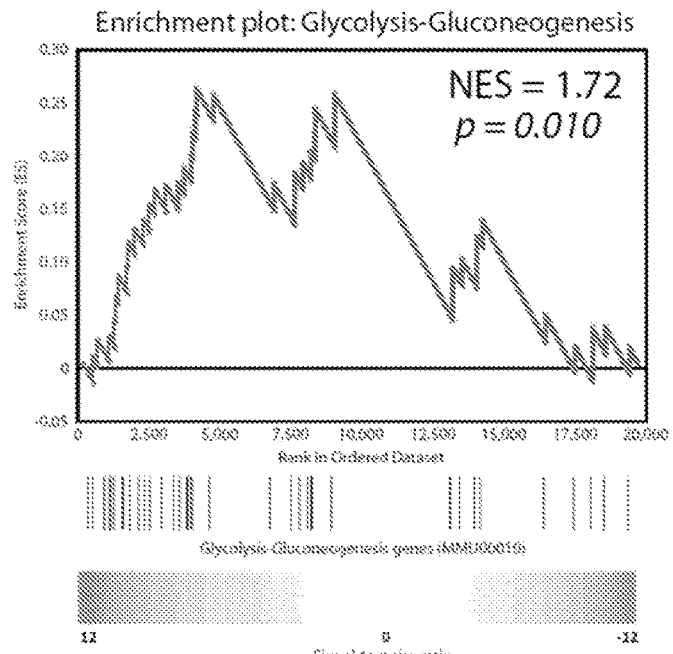
FIGS. 3A-3E show that Ldh activity increases during HFSC activation.
Figure 3B:
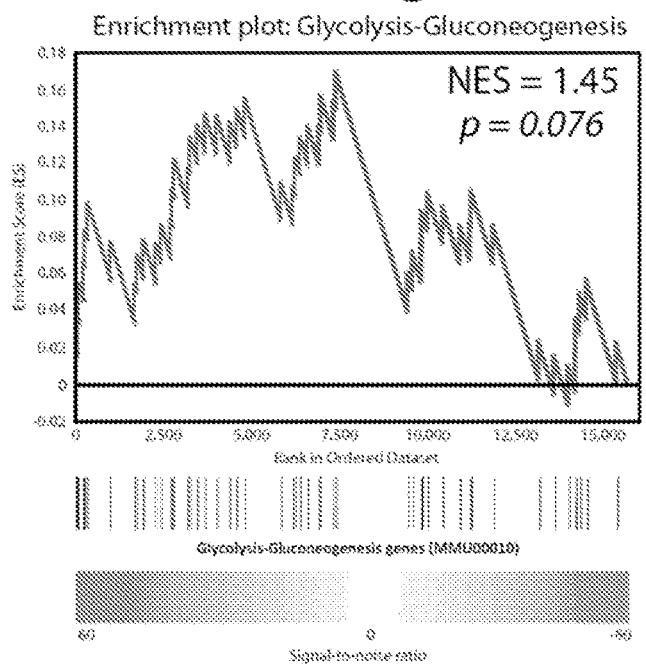
Figure 3C:
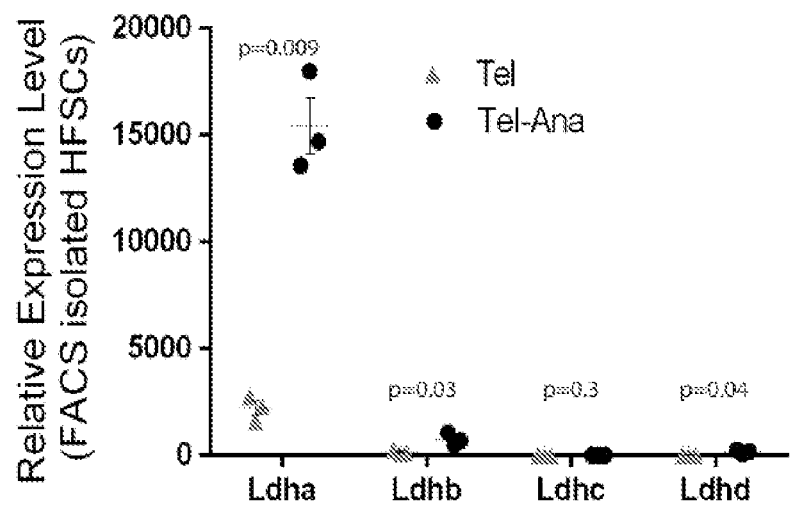

Measuring metabolism across the hair cycle therefore would capture any dynamic changes that occur in HFSCs that correlate with activation or quiescence. Analysis of RNA-seq data from HFSCs isolated during either telogen or the telogen-anagen transition demonstrated not only that Ldha is the predominant Ldh isoform expressed in HFSCs (FIG. 3), but is also induced during the telogen-anagen transition (FIGS. 3A and 3B (NIHGEOGSE67404 and GSE51635). To confirm that the cells analyzed by RNA-seq were indeed either in telogen or the telogen to anagen transition, important markers of this transition were assessed including the Shh and Wnt pathways (Gli1, 2, 3; Lef1, Axin1, Axin2, Ccnd1) as well as proliferation markers (Ki-67, Pcna and Sox4) (FIG. 4A).

Figure 3D:
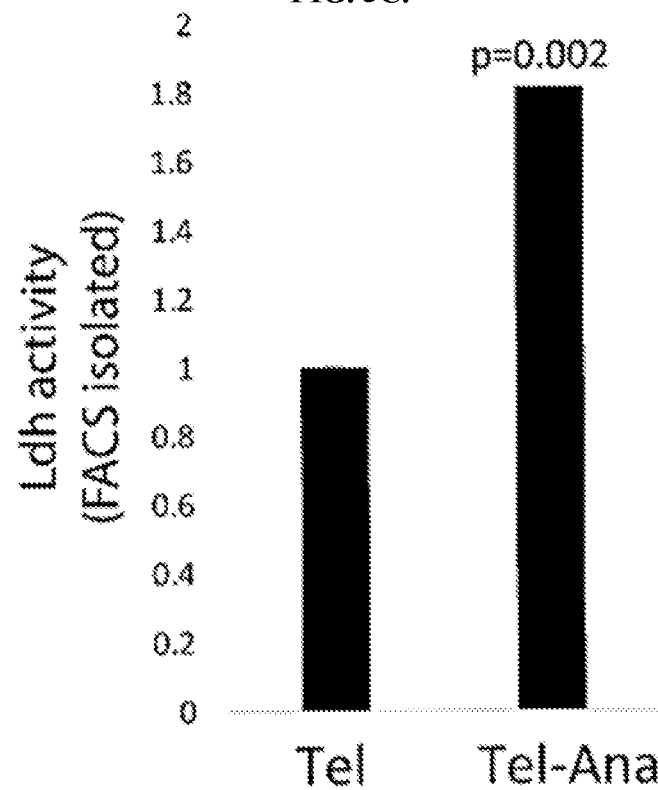
Figure 3E:
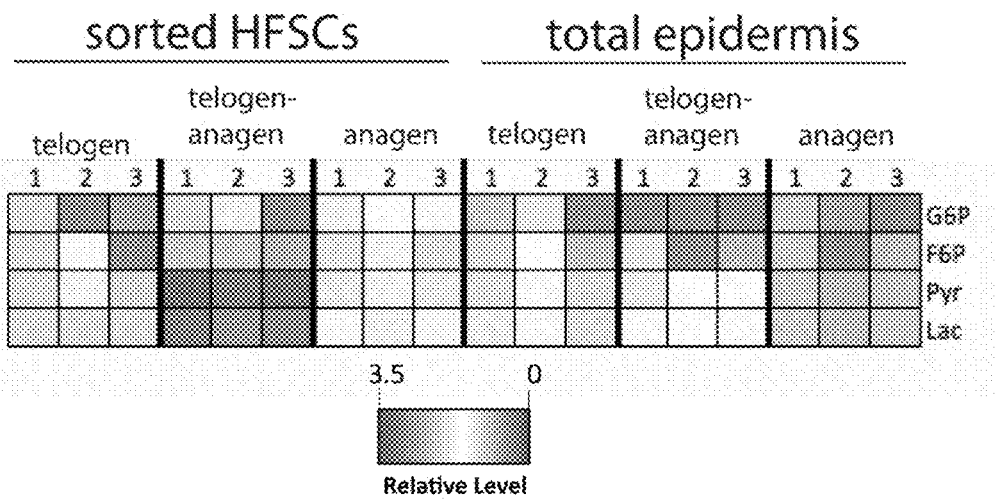
Figure 4A:
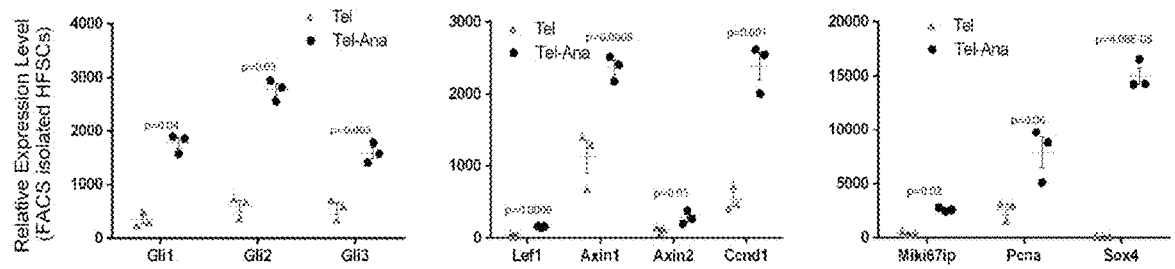
FIGS. 4A-4B show validation of hair cycle stage measurements.
Figure 4B:
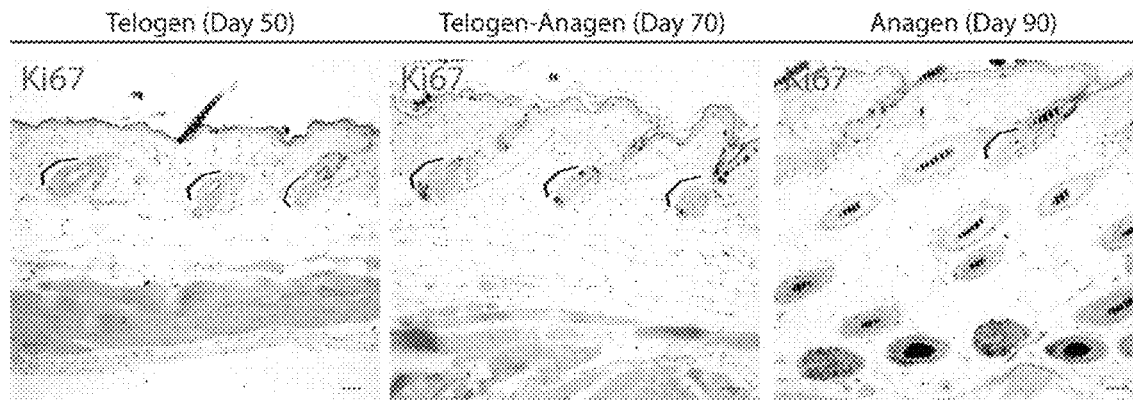

The in vitro Ldh activity assay on lysates from sorted HFSCs uncovered a modest induction of Ldh activity correlating with the telogen to anagen transition (FIG. 3D). Hair cycle staging was validated by Ki-67 immunostaining to determine HFSC activation (FIG. 4B). Additionally, measurements of steady-state metabolites extracted from sorted HFSCs showed an increase in lactate in HFSCs as they transition from telogen to telogen-anagen transition, and then decrease again in anagen as HFSCs return to quiescence (FIG. 3E).

Figure 20:
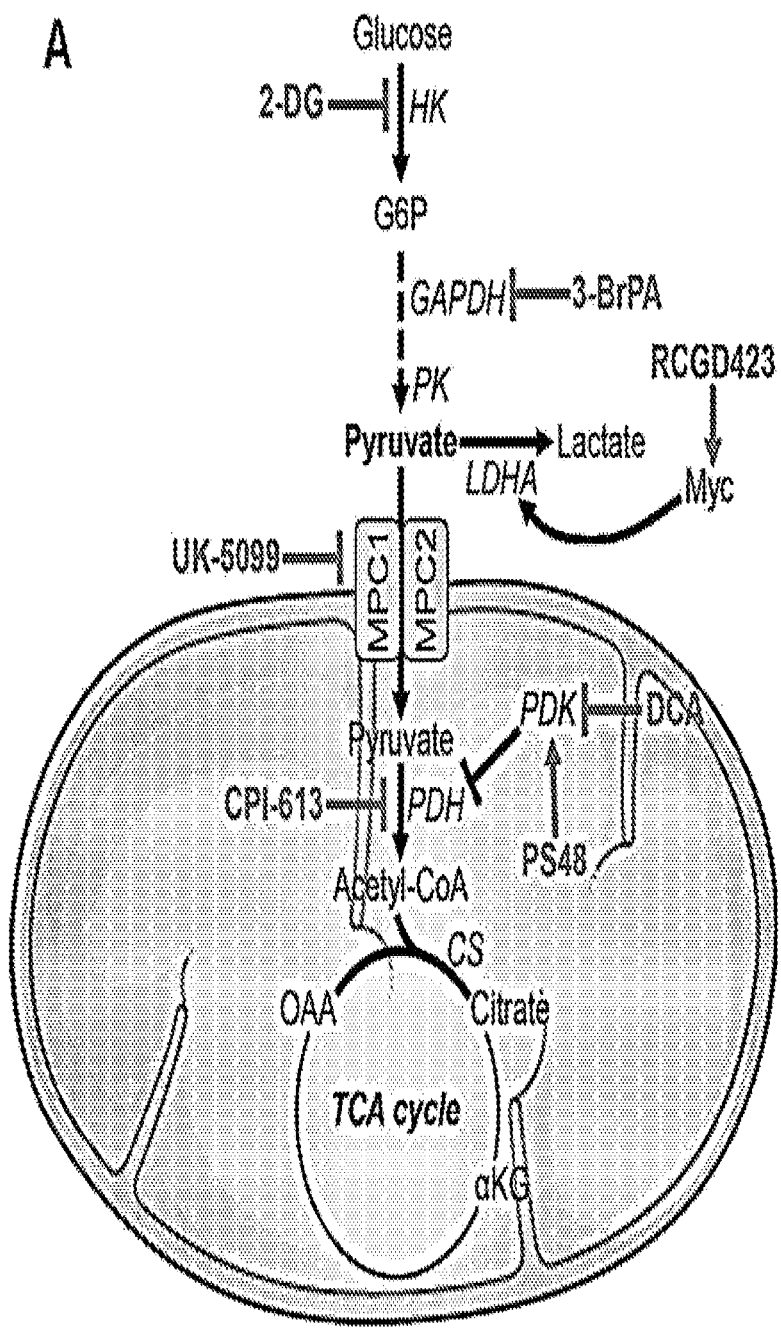
FIG. 20 shows the role of MPC in the oxidation of pyruvate to acetyl coenzyme A.

To determine whether induction of lactate production could affect HFSC activation or the hair cycle, we crossed KJ5CrePR animals to those floxed for mitochondrial pyruvate carrier 1 (Mpc1) (K15CrePR;Mpc1$^{fl/fl}$). Mpc1, as a heterodimer with Mpc2, forms the mitochondrial pyruvate carrier MPC, a transporter on the inner mitochondrial membrane required for pyruvate entry into the mitochondria. Loss of function of Mpc1 has been shown to drive lactate production through enhanced conversion of pyruvate to lactate by Ldh. Furthermore, inhibition of MPC results in a decrease in mitochondrial pyruvate oxidation (MPO) to acetyl coenzyme A (FIG. 20).

Figure 5A:
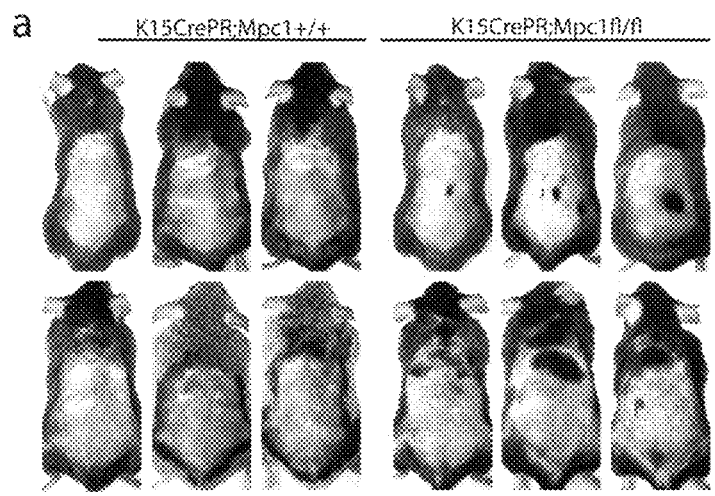
FIGS. 5A-5G show that deletion of Mpc1 increases lactate production and activation of HFSCs.
Figure 5B:
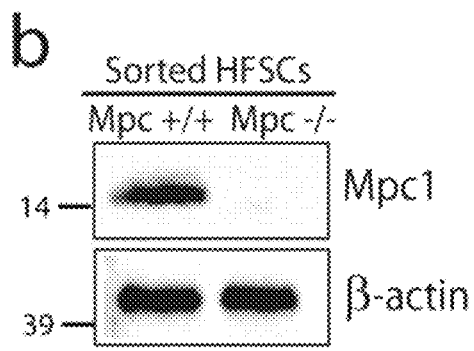
Figure 5C:
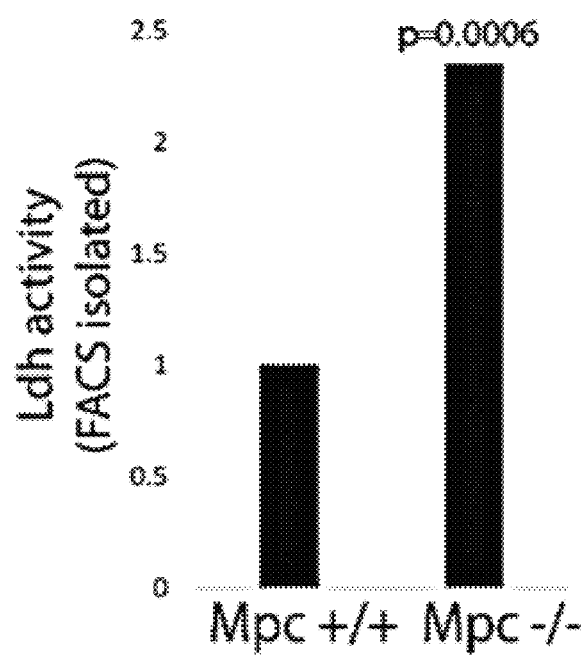

In animals with Mpc1 deletion in HFSCs, we observed a strong acceleration of the ventral and dorsal hair cycles with all the typical features of a telogen-anagen transition (FIG. 5A) (n=12 littermate pairs). Mifepristone treated K15CrePR;Mpc1$^{fl/fl}$ animals were the only to show any signs of dorsal anagen by day 70. Western blotting on sorted HFSCs validated the loss of Mpc1 protein (FIG. 5B). Importantly, purified HFSCs lacking Mpc1 showed a strong induction of Ldh activity (FIG. 5C). Quantification of the dorsal hair cycle across three pairs of littermates showed a strong induction of anagen in backskin lacking Mpc1 (FIG.

Figure 5D:
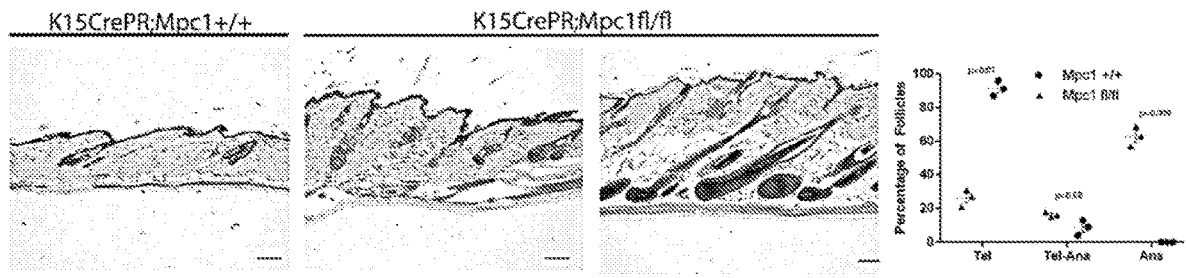
Figure 5E:
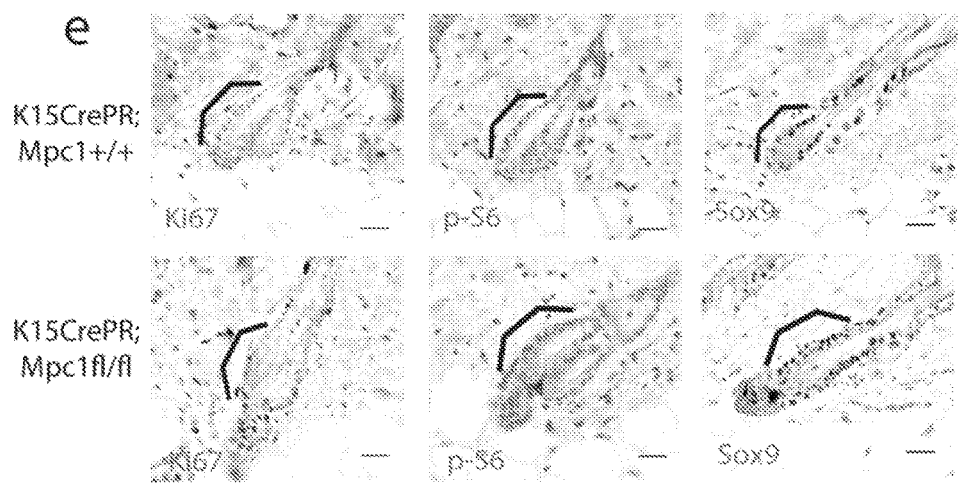
Figure 5F:
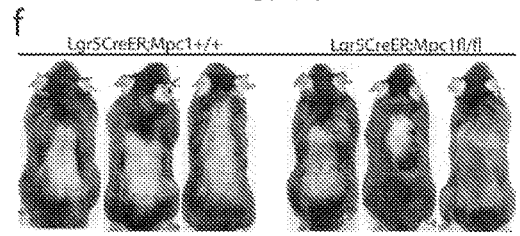
Figure 5G:
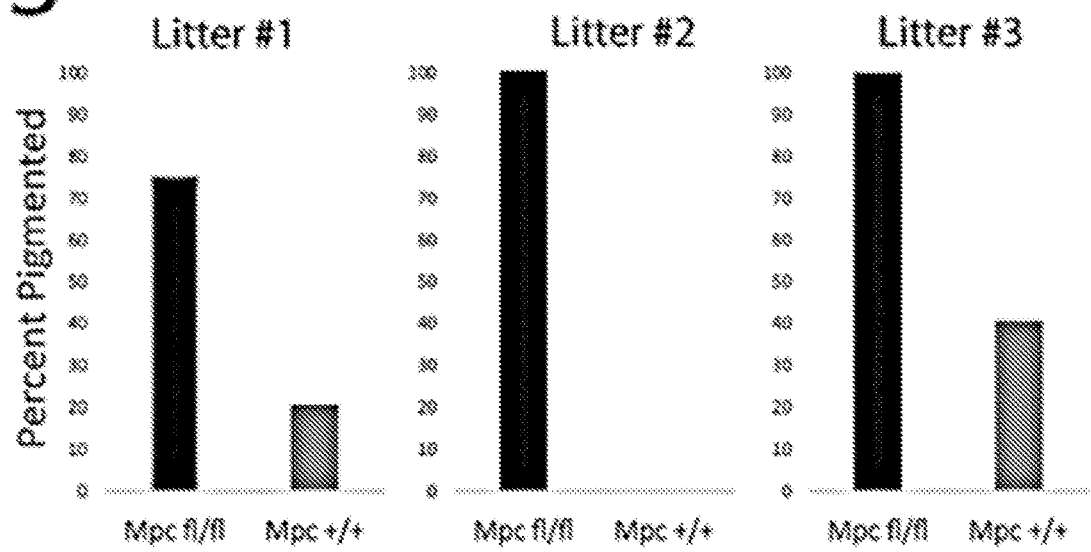
Figure 6A:
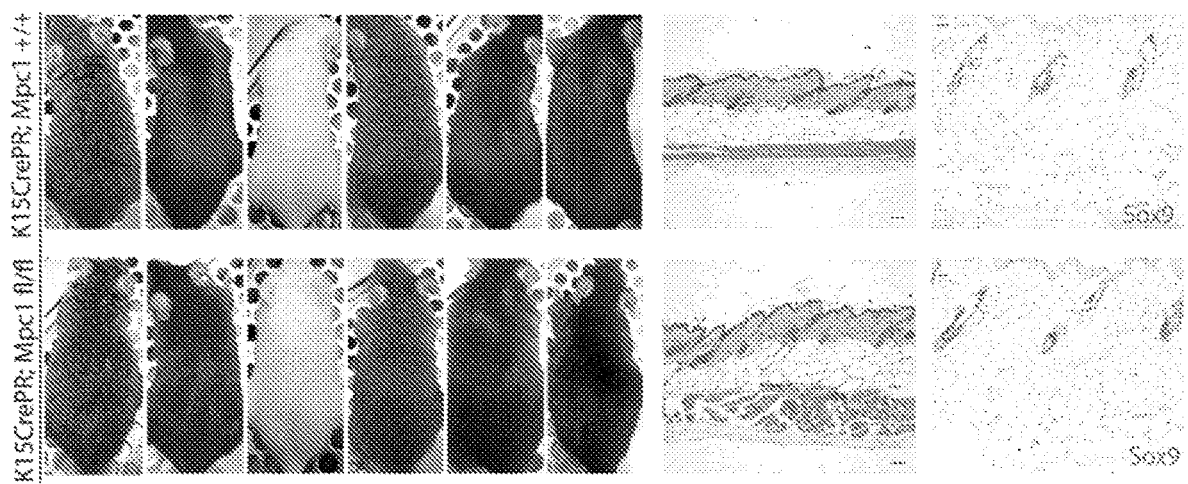
FIGS. 6A-6D show the effects of long term deletion of Mpc1 in HFSCs.
Figure 6B:
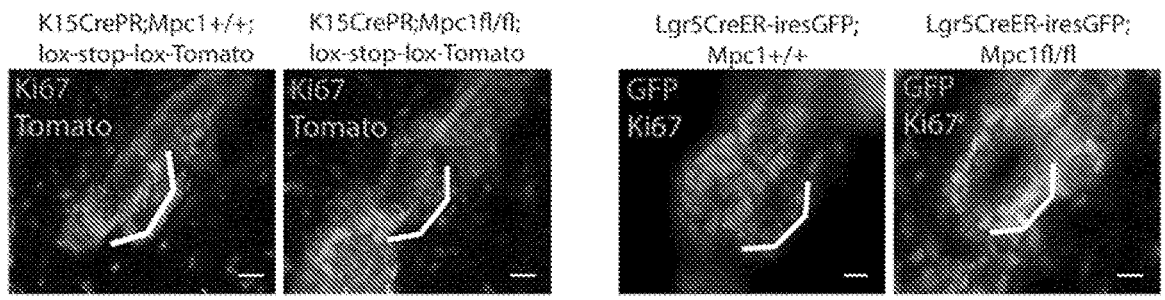
Figure 6C:
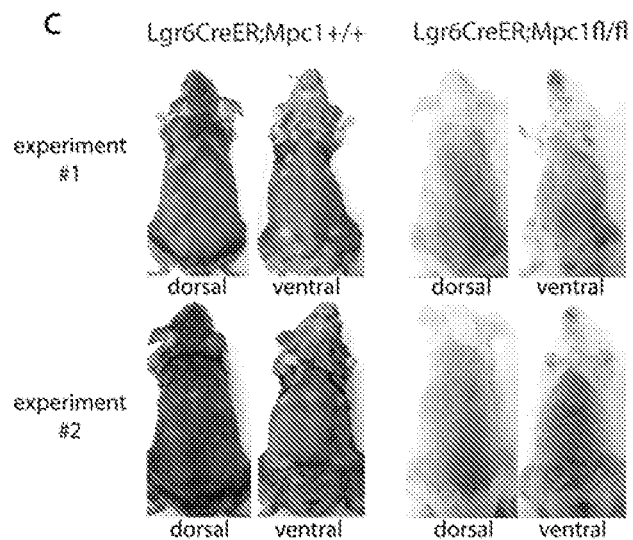
Figure 6D:
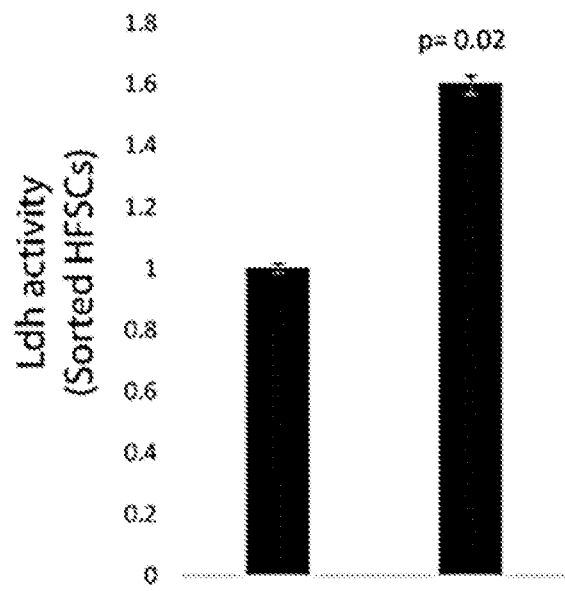

5D, right), and histology showed that the anagen induction was normal in appearance with a typical hypodermal expansion (FIG. 5D). Immunostaining demonstrated the induction in Mpc1-null HFSCs of various markers of hair cycle activation such as Ki-67 and pS6, while Sox9 expression was unaffected (FIG. 5E). Long term deletion of Mpc1 did not lead to aberrant follicles or exhaustion of HFSCs as judged by pathology and staining for Sox9 (FIG. 6A). Furthermore, deletion of Mpc1 with LgrCreER showed a very similar phenotype as deletion with K15CrePR (FIGS. 5F and 5G), validating the fact that deletion of this protein in HFSCs leads to their activation (n=12 pairs of littermates). Finally, immunofluorescence for the Ires-GFP of the Lgr5CreER transgene along with Ki-67 and lineage tracing with K15CrePR;Mpc1$^{fl/fl}$;lsl-Tomato mice also demonstrated that the HFSCs were indeed proliferative following induction of Mpc1 deletion by tamoxifen or mifepristone (FIG. 6B).

UK-5099 (also designated herein as JXL001) is a well-established pharmacological inhibitor of the mitochondrial pyruvate carrier and is known to promote lactate production as a result in various settings. UK-5099 has the following structure:

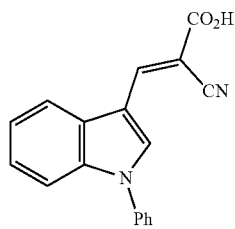 [SMILES: N#C/C(=C\c1cn(-c2ccccc2)c2ccccc12)C(=O)O]

Figure 7A:
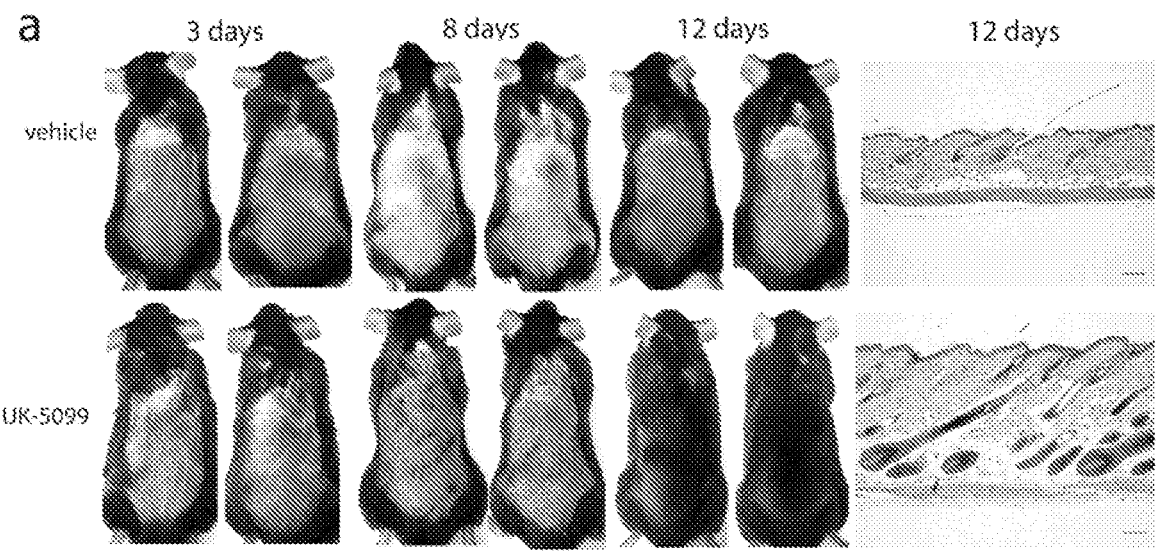
FIGS. 7A-7D show that pharmacological inhibition of Mpc1 promotes HFSC activation.
Figure 7B:
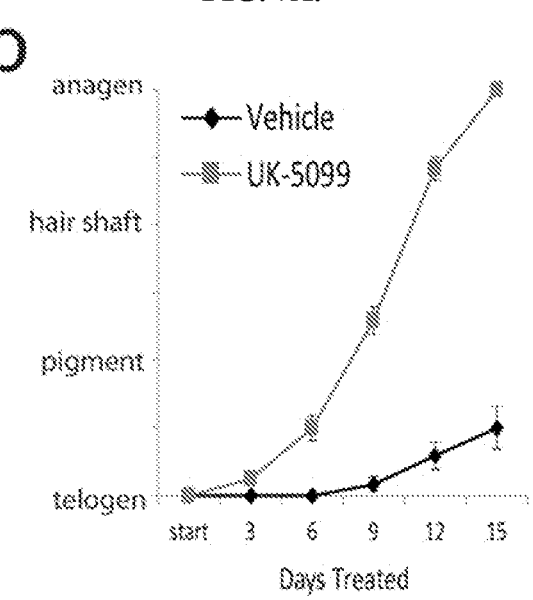
Figure 7C:
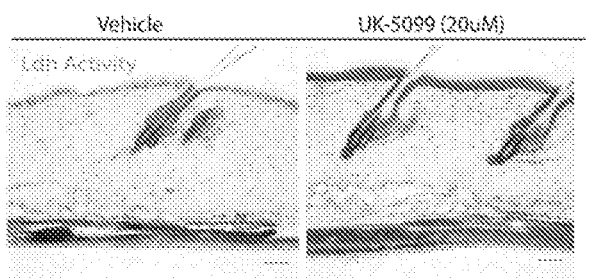
Figure 7D:
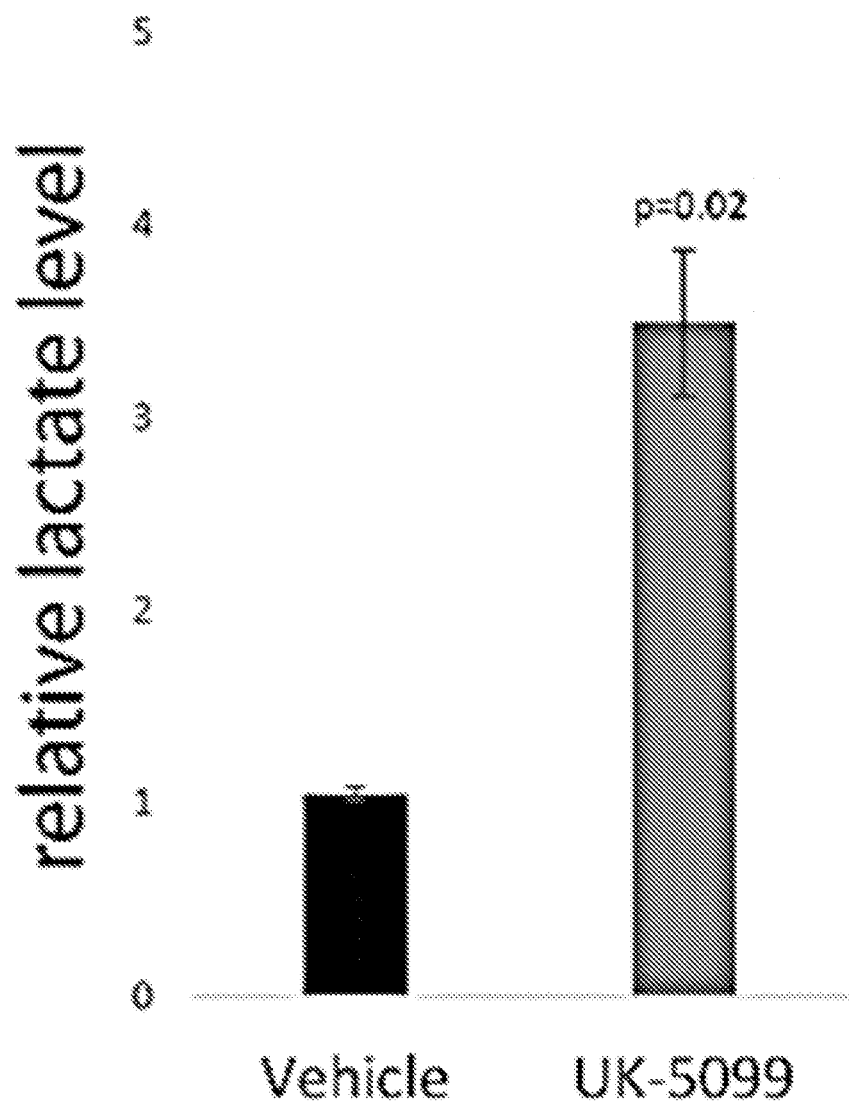

Topical treatment of animals in telogen (day 50) with UK-5099 led to a robust acceleration of the hair cycle, as well as minor hyperproliferation of the interfollicular epidermis (FIG. 7A). Quantification of the hair cycle across at least 6 pairs of animals (vehicle vs UK-5099) indicated a strong acceleration of the hair cycle, in as few as 6-9 days (FIG. 7B). Similar to genetic deletion of Mpc1, pharmacological blockade of the mitochondrial pyruvate carrier by UK-5099 for 48 hours during telogen promoted increased Ldh activity in HFSCs and the interfollicular epidermis, consistent with increased capacity for lactate production (FIG. 7C). Finally, metabolomic analysis demonstrated that topical application of UK-5099 increases total levels of lactate in sorted HFSCs (FIG. 7D).

Compounds were synthesized that could topically promote increased lactate levels and therefore drive the hair cycle.

The compounds were generally prepared by reaction of the corresponding aldehydes, e.g., for JXL001, 1-phenylindole-3-carboxaldehyde, with ethyl cyanoacetate in the presence of 40% aq. L-proline to give exclusively the E-isomer of the ethyl 2-cyano-3-(1-phenylindol-3yl)propenoate, e.g., JXL004. Hydrolysis of the ester with mild lithium hydroxide afforded the E-isomer of the acid, e.g., JXL001. All of the other compounds were prepared by analogous methods using the specific aldehyde. The two heterocyclic compounds, JXL023 and JXL024, were prepared from the condensation of 1-phenyl-indole-3-carboxaldehyde with thiazolidine-2,4-dione and 2-iminothiazolidin-4-one. The structures of all of the compounds were determined using normal organic chemistry methods, especially high field proton, carbon, and fluorine NMR spectra. In particular, $^3J_{C\text{-}H}$ coupling measurements demonstrated that the compounds all had the E-stereochemistry about the key carbon-carbon double bond.

To determine whether these compounds could promote cellular lactate production, we treated cultured epithelial cells with the compounds and measured lactate levels in the culture media using a Nova Biomedical BioProfile Basic Analyzer. Briefly, cultured epithelial cells were treated with DMSO, UK-5099 (also called JXL001), or certain of the exemplary compounds disclosed herein for 24-30 hours, and media lactate levels were measured and normalized to cell number and duration of the experiment to acquire a cellular lactate production rate (nmol lactate, million cells, hour). The results are shown in FIGS. 8 and 9.

Figure 8:
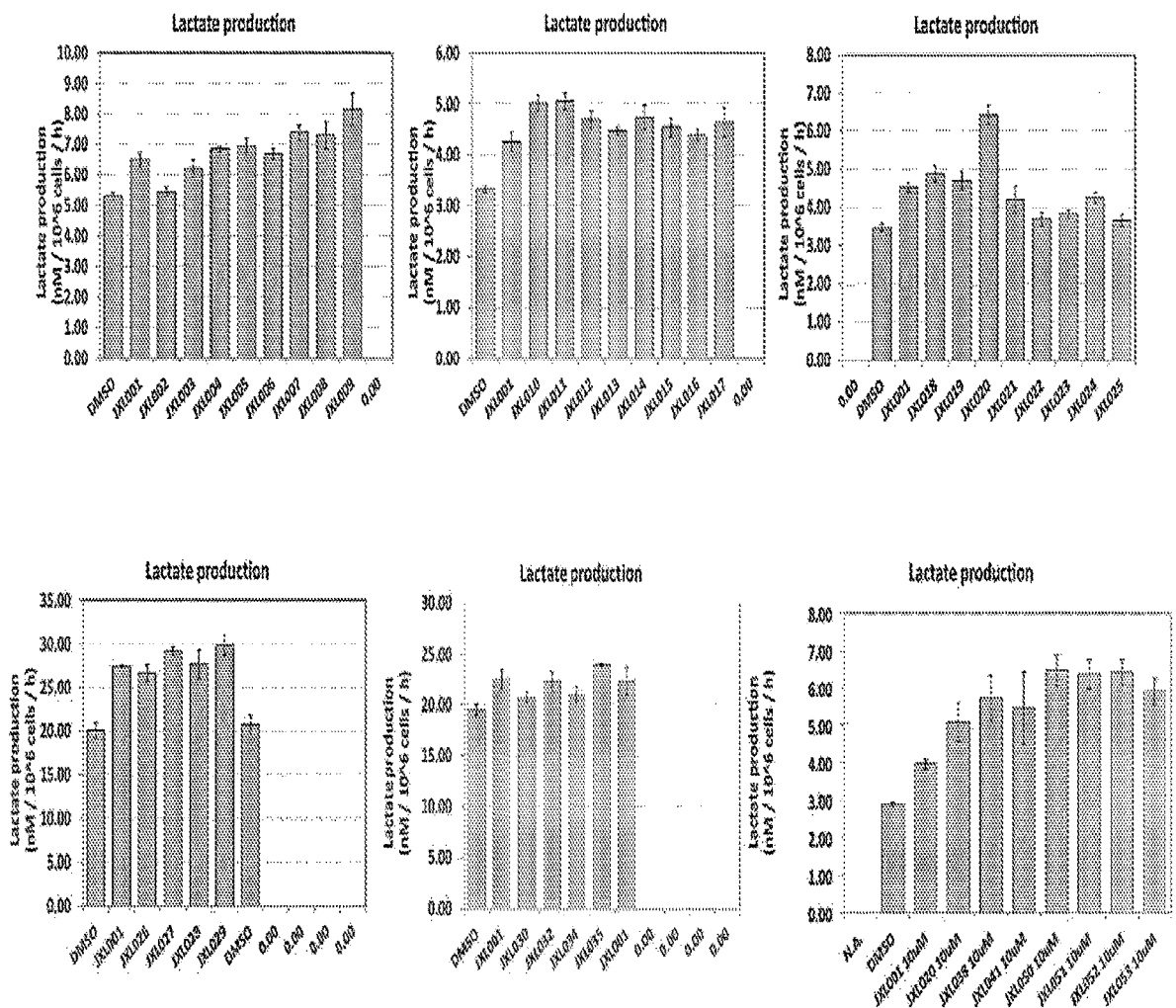
FIG. 8 shows the effect on lactate production of certain Mpc1 inhibitors described herein.
Figure 9:
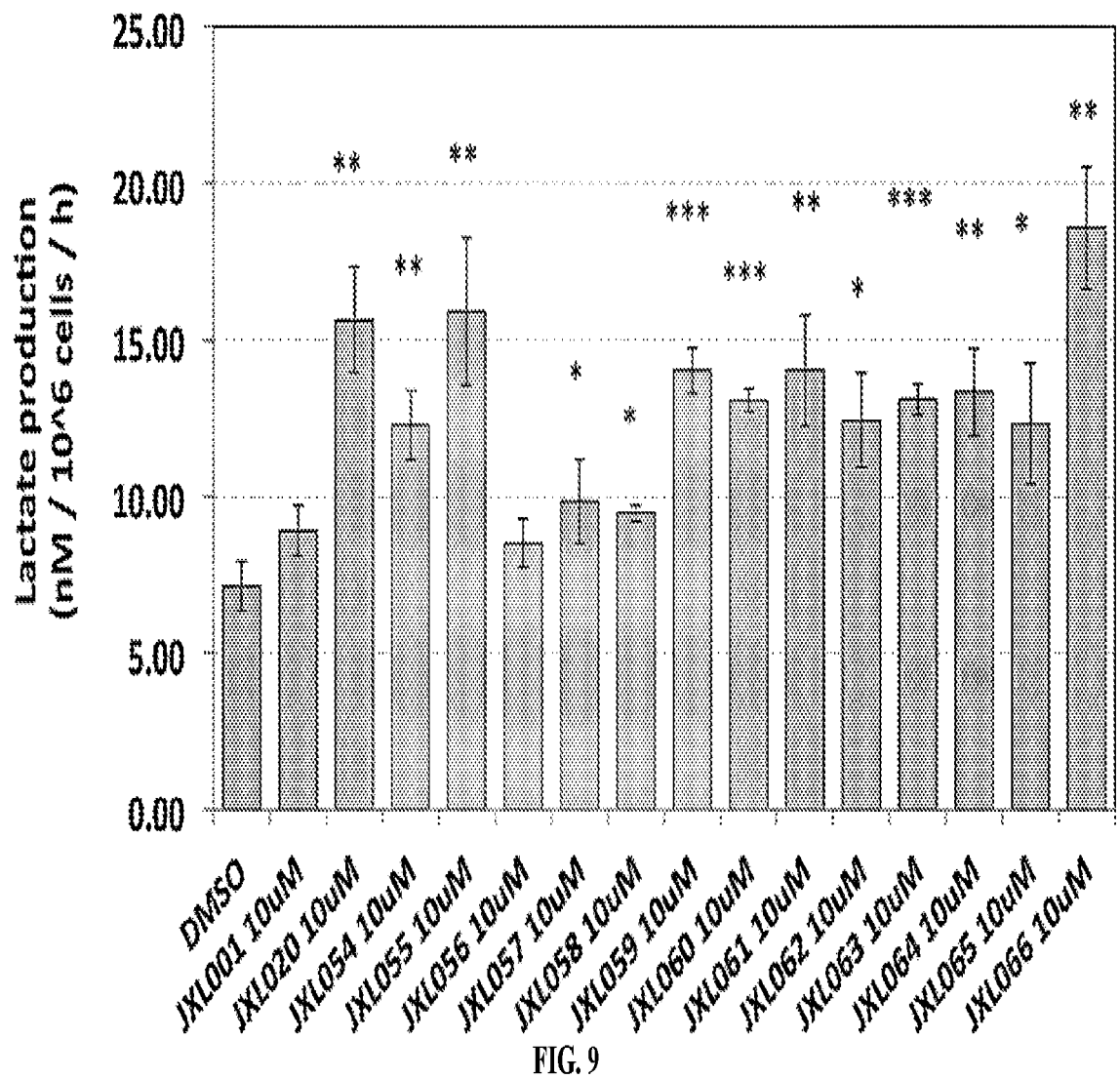
FIG. 9 shows the effect on lactate production of the certain Mpc1 inhibitor described herein.
Figure 10:
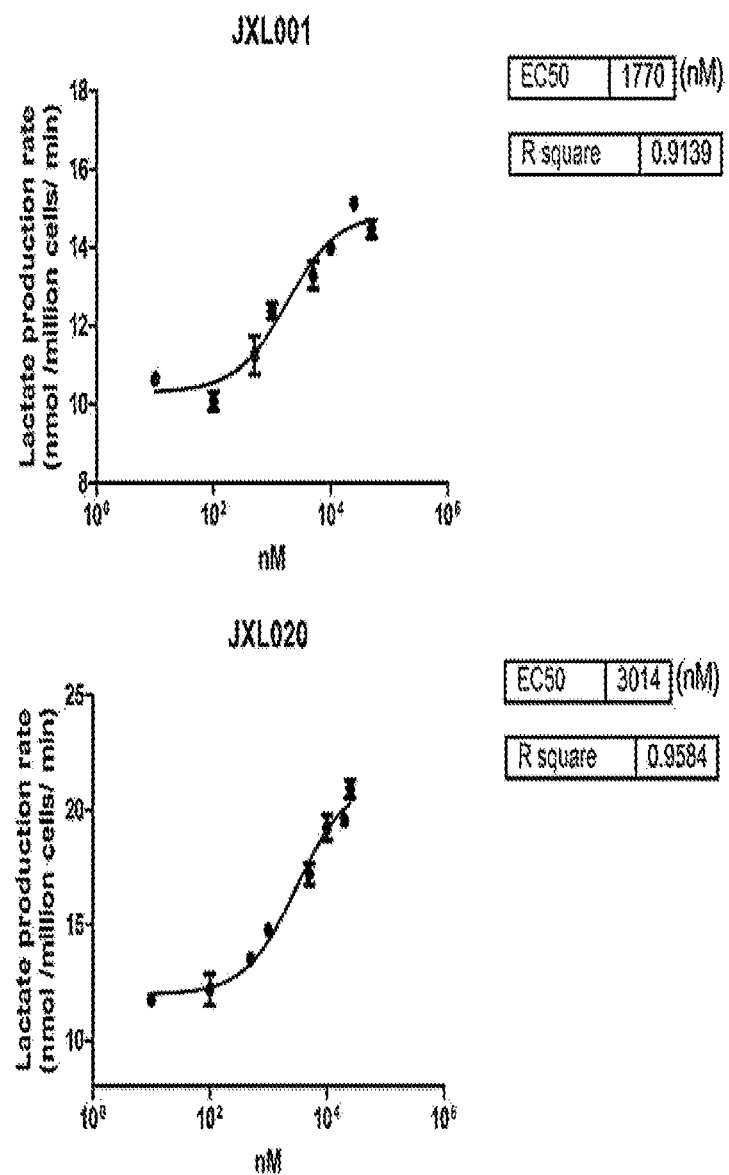
FIG. 10 shows the EC50 calculation for UK5099 and JXL020.

Lactate production rates of treated cells are shown in FIG. 8. As expected since they are UK-5099 analogues, most of the novel compounds assayed increased lactate production. A separate assay was performed to calculate the EC50 of some of the compounds as shown in FIG. 10.

Figure 11:
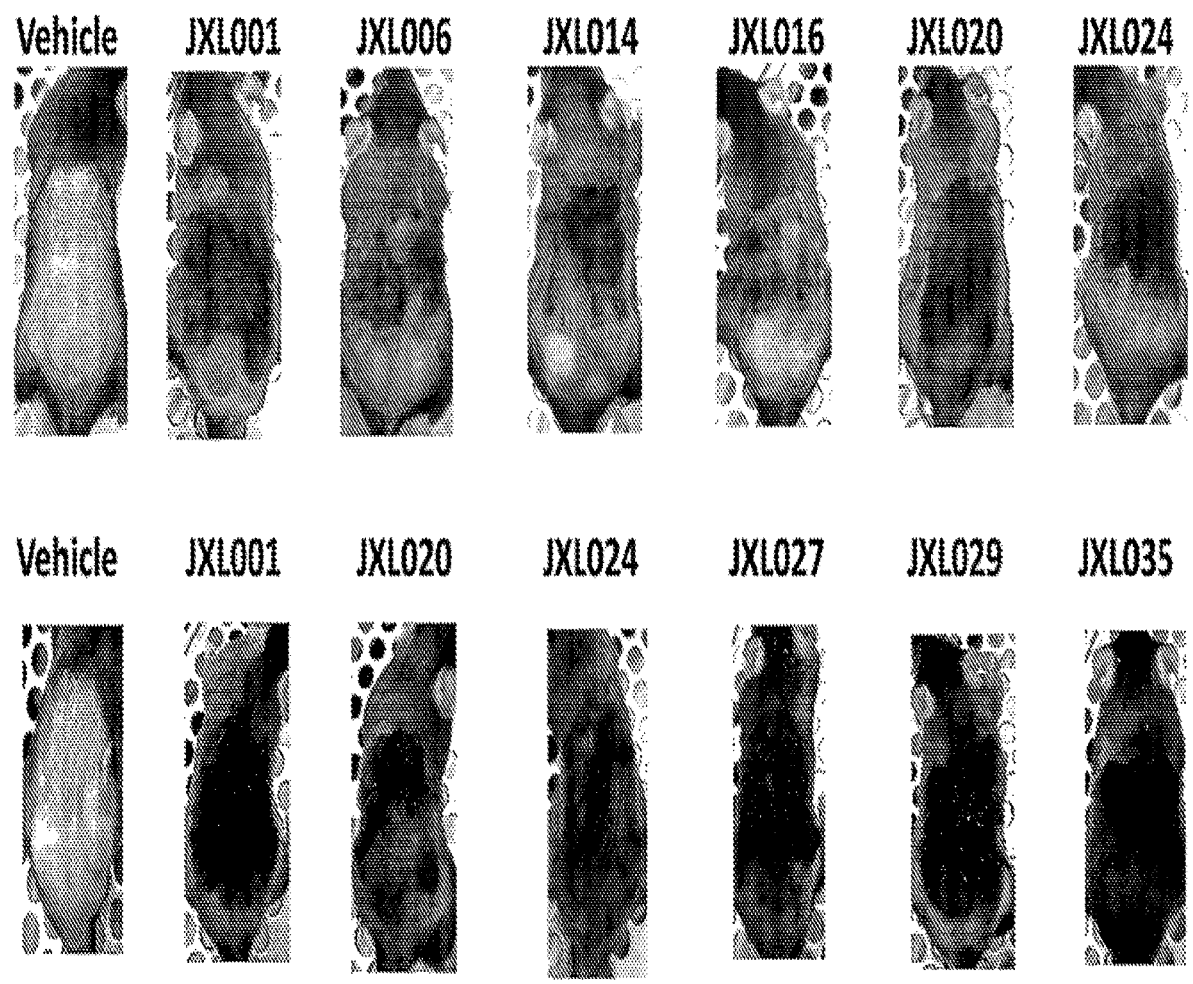
FIG. 11 shows that the Mpc1 inhibitors of the present invention induce hair growth.

To determine the efficacy of the compounds on the hair cycle, mice were shaved at postnatal day 50, and topically treated with a compound disclosed herein suspended in lotion in every other day for 3 weeks. As seen in FIG. 11, all the analogues that showed the ability to promote lactate production in the in vitro assay were also able to stimulate hair growth over the course of 2 weeks.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the amount of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject, will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x-C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

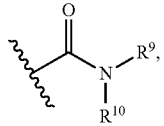

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

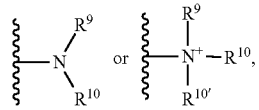

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

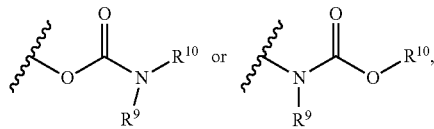

wherein $R^9$ and $R^{10}$ independently represent hydrogen or a hydrocarbyl group.

The term "carbocyclylalkyl", as used herein, refers to an alkyl group substituted with a carbocycle group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —OCO$_2$—.

The term "carboxy", as used herein, refers to a group represented by the formula —CO$_2$H.

The term "ester", as used herein, refers to a group —C(O)OR$^9$ wherein R$^9$ represents a hydrocarbyl group.

The term "ether" as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical.

Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

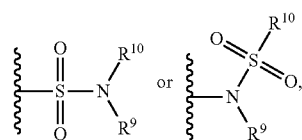

wherein $R^9$ and $R^{10}$ independently represents hydrogen or hydrocarbyl.

The term "sulfoxide" is art-recognized and refers to the group-S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein R$^9$ represents a hydrocarbyl.

The term "thioether", as used herein, is equivalent to an ether, wherein the oxygen is replaced with a sulfur.

The term "urea" is art-recognized and may be represented by the general formula

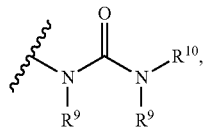

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by formula I or II. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of formula I or II are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of formula I or II for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by formula I or II or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I or II). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of formula I or II. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

EXAMPLES

The invention now being generally described, it will be more readily understood by reference to the following examples which are included merely for purposes of illustration of certain aspects and embodiments of the present invention, and are not intended to limit the invention.

Example 1: Preparation of Exemplary Compounds

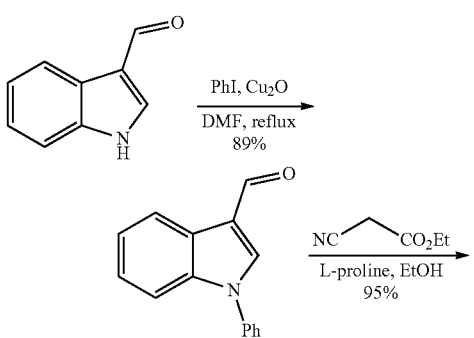

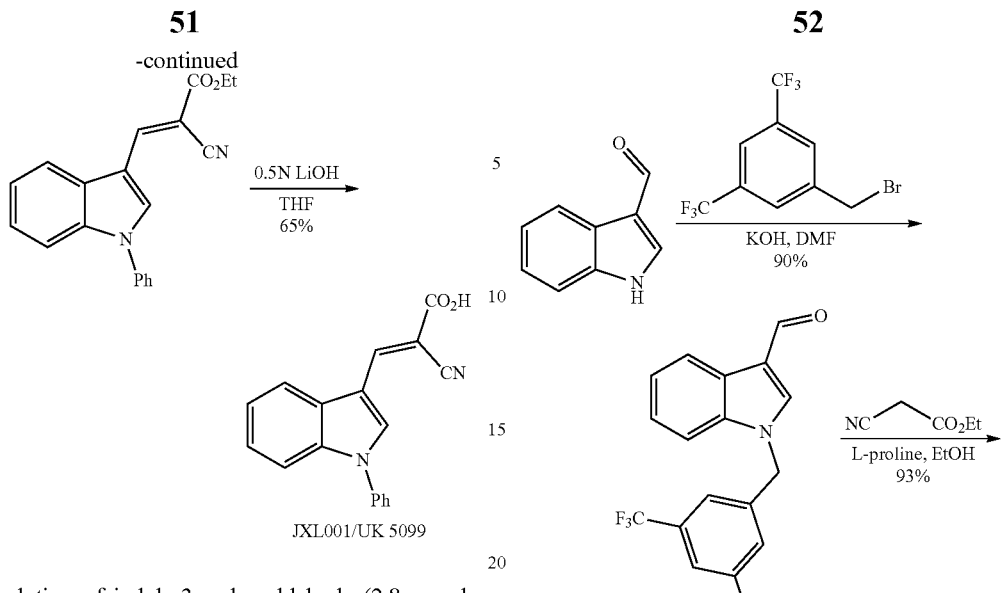

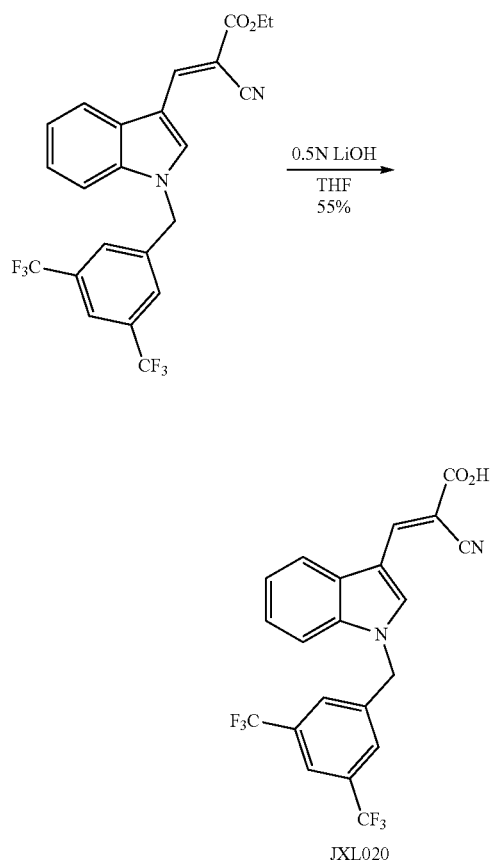

To the solution of indole-3-carboxaldehyde (2.8 mmol, 411 mg) in dry DMF (6 mL) were added Cu$_2$O (0.3 equiv, 0.84 mmol, 120 mg), K$_2$CO$_3$ (2.0 equiv, 5.6 mmol, 774 mg), and iodobenzene (2.0 equiv, 5.6 mmol, 624 μL) sequentially. The reaction was stirred and refluxed for 24 h, at which point TLC indicated that the reaction was completed. After it was cooled to 21° C., the reaction mixture was filtrated through a Celite pad eluting with ethyl acetate. The filtrate was washed by saturated NaCl solution and organic phase was dried by sodium sulfate and concentrated. The residue was purified by flash column chromatography (hexanes/EtOAc=8:1) to provide the desired product. yield: 89%, 550.7 mg.

To the solution of 1-phenyl-indole-3-carbaldehyde (1 mmol, 221 mg) in ethanol (1 mL) were added ethyl 2-cyanoacetate (1.3 equiv, 1.3 mmol, 140 μL) and L-proline (40 mol %, 0.4 mmol, 58 mg). The reaction was stirred at 21° C. for 12 h and yellow solid precipitated gradually. After completion of the reaction, ice-cold water (2 mL) was added into the reaction vial. The solid was separated by Buchner funnel filtration and washed with water (2 mL×3) and dried to afford the desired product. yield: 95%, 300 mg.

To the solution of (E)-ethyl 2-cyano-3-(1-phenyl-1H-indol-3-yl)acrylate (0.32 mmol, 100 mg) in THF (2 mL) was added 0.5N LiOH solution (3 equiv, 0.6 mmol, 1.2 mL). The reaction mixture was stirred at 21° C. for 1 h. After reaction completion shown by TLC, THF was evaporated. Concentrated HCl was added dropwise to acidify the reaction mixture until the pH was lower than 1, meanwhile yellow solid precipitated. Ice-cold water (5 mL) was added to the reaction mixture and the solid was separated by Buchner funnel filtration and washed with water (5 mL×3). After dried by vacuum, the solid was washed by 2 mL of solvent mixture (hexanes/EtOAc=5:1) 5 to 10 times and monitored by TLC until non-polar impurities disappear (The non-polar compound was the retro-Aldol condensation product, which can be recovered from the filtrate). Finally, the purity of the product was checked by NMR. yield: 65%, 60 mg.

(E)-2-Cyano-3-(1-phenyl-1H-indol-3-yl)acrylic acid (JXL001/UK5099)

$^1$H NMR (500 MHz, DMSO-d$_6$) δ 8.59 (s, 1H), 8.56 (s, 1H), 8.06 (m, 1H), 7.65 (m, 4H), 7.53 (m, 2H), 7.34 (m, 2H).
$^{13}$C NMR (126 MHz, DMSO-d$_6$) δ 164.5, 145.6, 137.7, 136.3, 133.6, 130.5, 128.9, 128.0, 125.0, 124.9, 123.3, 119.9, 118.4, 111.9, 96.7.

The following compounds were synthesized by a route similar to that described for JXL001: JXL002, JXL003, JXL004, JXL005, JXL006, JXL007, JXL012, JXL013, JXL014, JXL021, JXL025 JXL026, JXL027, JXL028, JXL029, JXL035, JXL093.

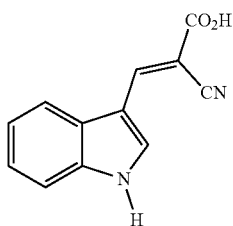

(E)-2-Cyano-3-(1H-indol-3-yl)acrylic Acid (JXL002)

¹H NMR (500 MHz, DMSO-d₆) δ 12.48 (s, 1H), 8.51 (s, 1H), 8.49 (s, 1H), 7.91 (d, J=6.5 Hz, 1H), 7.53 (d, J=7.0 Hz, 1H), 7.23 (m, 2H).
¹³C NMR (126 MHz, DMSO-d₆) δ 165.0, 146.5, 136.5, 132.4, 127.3, 123.9, 122.4, 118.9, 118.8, 113.2, 110.2, 94.0.

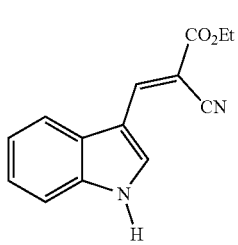

Ethyl (E)-2-cyano-3-(1H-indol-3-yl)acrylate

¹H NMR (500 MHz, CDCl₃) δ 12.55 (s, 1H), 8.53 (s, 1H), 8.52 (s, 1H), 7.92 (d, J=7.6 Hz, 1H), 7.53 (d, J=7.8 Hz, 1H), 7.26 (app. t, J=7.4 Hz, 1H), 7.22 (app. t, J=7.4 Hz, 1H), 4.24 (q, J=7.0 Hz, 2H), 1.26 (t, J=7.0 Hz, 3H).
¹³C NMR (126 MHz, CDCl₃) δ 163.6, 147.0, 136.6, 133.0, 127.3, 124.0, 122.5, 118.9, 118.4, 113.3, 110.3, 92.6, 61.8, 14.5.

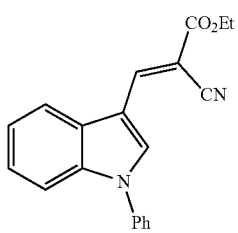

Ethyl (E)-2-cyano-3-(1-phenyl-1H-indol-3-yl)acrylate (JXL004)

¹H NMR (500 MHz, CDCl₃) δ 8.71 (s, 1H), 8.66 (s, 1H), 7.90 (d, J=7.2 Hz, 1H), 7.54 (m, 6H), 7.36 (m, 2H), 4.39 (q, J=7.1 Hz, 2H), 1.42 (t, J=7.1 Hz, 3H).
¹³C NMR (126 MHz, CDCl₃) δ 163.6, 145.6, 137.8, 136.4, 133.2, 129.9, 128.5, 124.8, 124.4, 123.0, 118.5, 117.9, 111.6, 111.5, 95.4, 62.0, 14.3.

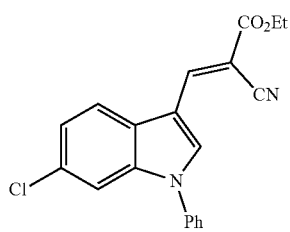

Ethyl (E)-3-(6-chloro-1-phenyl-1H-indol-3-yl)-2-cyanoacrylate (JXL005)

¹H NMR (500 MHz, CDCl₃) δ 8.67 (s, 1H), 8.58 (s, 1H), 7.81 (d, J=8.5 Hz, 1H), 7.60 (m, 2H), 7.52 (m, 4H), 7.34 (d, J=8.4 Hz, 1H), 4.39 (q, J=7.1 Hz, 2H), 1.41 (t, J=7.1 Hz, 3H).
¹³C NMR (126 MHz, CDCl₃) δ 163.4, 145.1, 137.3, 136.8, 133.5, 130.5, 130.0, 128.8, 126.8, 124.8, 123.6, 119.5, 117.5, 111.6, 111.4, 96.4, 62.1, 14.2.

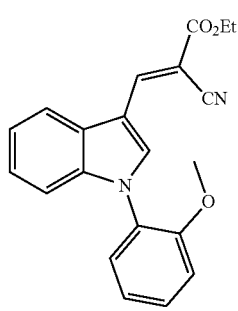

Ethyl (E)-2-cyano-3-(1-(2-methoxyphenyl)-1H-indol-3-yl)acrylate (JXL006)

¹H NMR (500 MHz, CDCl₃) δ 8.67 (s, 1H), 8.66 (s, 1H), 7.89 (d, J=7.8 Hz, 1H), 7.49 (app. t, J=8.6 Hz, 1H), 7.41 (d, J=7.6 Hz, 1H), 7.35 (app. t, J=7.3 Hz, 1H), 7.30 (t, J=7.5 Hz, 1H), 7.23 (d, J=8.1 Hz, 1H), 7.13 (m, 2H), 4.39 (q, J=7.1 Hz, 2H), 3.81 (s, 3H), 1.41 (t, J=7.1 Hz, 3H).
¹³C NMR (126 MHz, CDCl₃) δ 163.8, 154.2, 146.0, 137.2, 135.2, 130.3, 127.8, 126.0, 124.0, 122.6, 120.8, 118.2, 118.0, 112.3, 111.8, 111.0, 94.7, 61.8, 55.7, 14.3.

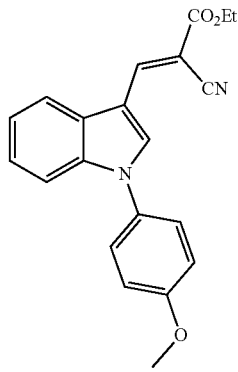

Ethyl (E)-2-cyano-3-(1-(4-methoxyphenyl)-1H-indol-3-yl)acrylate (JXL007)

¹H NMR (500 MHz, CDCl₃) δ 8.65 (s, 1H), 8.64 (s, 1H), 7.89 (d, J=7.2 Hz, 1H), 7.44 (m, 3H), 7.35 (m, 2H), 7.07 (d, J=8.8 Hz, 2H), 4.38 (q, J=7.1 Hz, 2H), 3.90 (s, 3H), 1.41 (t, J=7.1 Hz, 3H).

¹³C NMR (126 MHz, CDCl₃) δ 163.8, 159.5, 145.6, 136.8, 133.5, 130.6, 128.3, 126.2, 124.2, 122.9, 118.4, 118.0, 115.0, 111.5, 111.1, 94.9, 61.9, 55.6, 14.2.

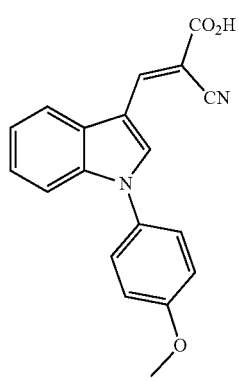

JXL012

(E)-2-Cyano-3-(1-(4-methoxyphenyl)-1H-indol-3-yl) acrylic acid (JXL012)

¹H NMR (500 MHz, DMSO-d₆) δ 8.54 (s, 1H), 8.52 (s, 1H), 8.05 (d, J=7.7 Hz, 1H), 7.58 (app. d, J=8.7 Hz, 2H), 7.44 (m, 1H), 7.33 (m, 2H), 7.16 (app. d, J=8.7 Hz, 2H), 3.82 (s, 3H).

¹³C NMR (126 MHz, DMSO-d₆) δ 164.7, 160.5, 136.7, 133.9, 130.5, 127.8, 126.6, 124.8, 123.2, 120.0, 119.5, 118.6, 115.6, 115.4, 111.9, 110.9, 55.9.

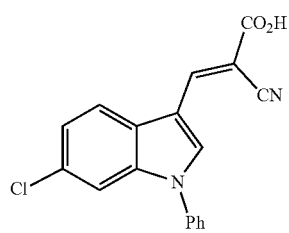

JXL013

(E)-3-(6-Chloro-1-phenyl-1H-indol-3-yl)-2-cyano-acrylic Acid (JXL013)

¹H NMR (500 MHz, DMSO-d₆) δ 13.58 (br. s, 1H), 8.59 (s, 1H), 8.54 (s, 1H), 8.11 (d, J=7.5 Hz, 1H), 7.67 (m, 4H), 7.53 (m, 2H), 7.35 (d, J=7.5 Hz, 1H).

¹³C NMR (126 MHz, DMSO-d₆) δ 164.3, 145.4, 137.3, 136.7, 134.4, 130.6, 129.6, 129.1, 126.7, 125.1, 123.5, 121.5, 118.2, 111.6, 111.3, 97.9.

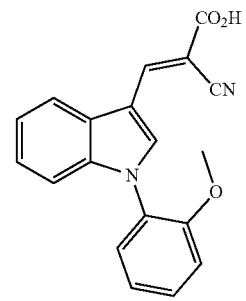

JXL014

(E)-2-Cyano-3-(1-(2-methoxyphenyl)-1H-indol-3-yl) acrylic acid (JXL014)

¹H NMR (500 MHz, DMSO-d₆) δ 8.55 (s, 1H), 8.47 (s, 1H), 8.02 (d, J=7.4 Hz, 1H), 7.54 (m, 2H), 7.31 (m, 3H), 7.15 (m, 2H), 3.74 (s, 3H).

¹³C NMR (126 MHz, DMSO-d₆) δ 164.6, 154.2, 145.8, 137.3, 135.1, 131.1, 128.2, 127.3, 125.7, 124.6, 123.0, 121.5, 119.3, 118.5, 113.6, 112.2, 110.8, 96.1, 56.2.

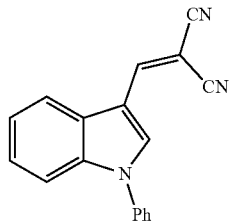

JXL021

2-((1-Phenyl-1H-indol-3-yl)methylene)malononitrile (JXL021)

¹H NMR (500 MHz, CDCl₃) δ 8.62 (s, 1H), 8.13 (s, 1H), 7.80 (d, J=7.4 Hz, 1H), 7.61 (m, 2H), 7.53 (m, 4H), 7.40 (m, 2H).

¹³C NMR (126 MHz, CDCl₃) δ 149.8, 137.3, 136.5, 133.6, 130.1, 128.9, 127.7, 124.9, 124.8, 123.7, 118.2, 115.1, 115.0, 111.9, 111.8, 73.7.

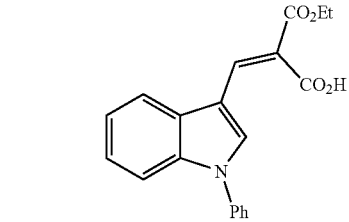

JXL025

2-(Ethoxycarbonyl)-3-(1-phenyl-1H-indol-3-yl) acrylic acid (a mixture of E/Z isomers, 1:1 ratio) (JXL025)

¹H NMR (500 MHz, DMSO-d₆) δ 13.08 (br. s, 1H), 7.87 (m, 3H), 7.61 (m, 4H), 7.52 (m, 2H), 7.30 (m, 2H), 4.26 (m, 2H), 1.23 (m, 3H).

$^{13}$C NMR (126 MHz, DMSO-d$_6$) δ 168.9, 167.8, 166.1, 164.9, 138.3, 136.1, 132.9, 132.1, 131.1, 130.9, 130.8, 128.5, 124.9, 124.4, 122.6, 122.2, 119.5, 111.6, 111.0, 61.7, 61.3, 14.7, 14.4.

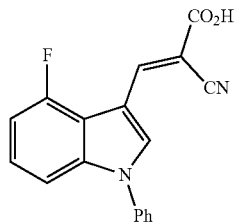

JXL026

(E)-2-Cyano-3-(4-fluoro-1-phenyl-1H-indol-3-yl) acrylic acid (JXL026)

$^{1}$H NMR (500 MHz, DMSO-d$_6$) δ 8.65 (s, 1I), 8.61 (s, 1H), 7.67 (m, 4H), 7.57 (m, 1H), 7.36 (m, 2H), 7.19 (m, 1H).
$^{13}$C NMR (126 MHz, DMSO-d$_6$) δ 164.4, 156.8 (d, $J_{c-f}$=245.6 Hz), 146.4, 138.7, 137.6, 133.4, 130.7, 129.5, 125.9, 125.4, 118.2, 116.3, 116.2, 109.5 (d, $J_{c-f}$=34.5 Hz), 109.2 (d, $J_{c-f}$=23.2 Hz), 98.0.

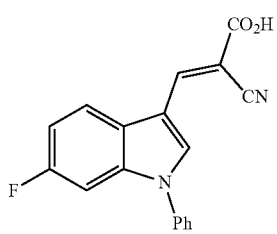

JXL027

(E)-2-Cyano-3-(6-fluoro-1-phenyl-1H-indol-3-yl) acrylic Acid (JXL027)

$^{1}$H NMR (500 MHz, DMSO-d$_6$) δ 13.59 (br. s, 1H), 8.62 (s, 1H), 8.59 (s, 1H), 8.16 (m, 1H), 7.66 (m, 4H), 7.56 (m, 1H), 7.36 (d, J=9.2 Hz, 1H), 7.25 m, 1H).
$^{13}$C NMR (126.1 Hz, DMSO-d$_6$) δ 164.6, 160.8 (d, $J_{c-f}$=240.0 Hz), 145.7, 137.6, 136.6, 134.4, 130.8, 129.1, 125.0, 124.7, 121.6, 118.4, 111.8 (d, $J_{c-f}$=24.2 Hz), 111.5, 98.7 (d, $J_{c-f}$=26.2 Hz), 97.7.

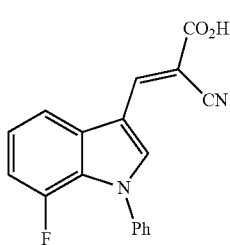

JXL028

(E)-2-Cyano-3-(7-fluoro-1-phenyl-1H-indol-3-yl) acrylic Acid (JXL028)

$^{1}$H NMR (500 MHz, DMSO-d$_6$) δ 13.62 (br. s, 1H), 8.56 (s, 1H), 8.47 (s, 1H), 7.89 (br. s, 1H), 7.61 (m, 5H), 7.30 (br. s, 1H), 7.17 (br. s, 1H).

$^{13}$C NMR (126 MHz, DMSO-d$_6$) δ 164.4, 149.7 (d, $J_{c-f}$=247.5 Hz), 145.5, 139.0, 135.5, 131.9, 129.9, 129.3, 126.2, 124.3, 124.0, 118.3, 115.9, 111.8, 110.9 (d, $J_{c-f}$=17.4 Hz), 98.1.

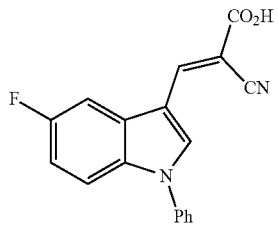

JXL029

(E)-2-Cyano-3-(5-fluoro-1-phenyl-1H-indol-3-yl) acrylic acid (JXL029)

$^{1}$H NMR (500 MHz, DMSO-d$_6$) δ 13.57 (br. s, 1H), 8.67 (s, 1H), 8.60 (s, 1H), 8.01 (d, J=9.0 Hz, 1H), 7.70 (m, 4H), 7.58 (m, 2H), 7.24 (m, 1H).
$^{13}$C NMR (126 MHz, DMSO-d$_6$) δ 164.6, 159.4 (d, $J_{c-f}$=237.8 Hz), 145.8, 137.7, 135.1, 133.1, 130.7, 129.2, 129.1, 125.2, 118.5, 113.7, 113.2 (d, $J_{c-f}$=26.5 Hz), 111.4, 105.7 (d, $J_{c-f}$=24.2 Hz), 97.2.

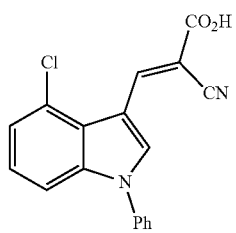

JXL035

(E)-3-(4-Chloro-1-phenyl-1H-indol-3-yl)-2-cyanoacrylic Acid (JXL035)

$^{1}$H NMR (500 MHz, DMSO-d$_6$) δ 9.22 (s, 1H), 8.68 (s, 1H), 7.64 (m, 3H), 7.59 (m, 2H), 7.48 (d, J=7.6 Hz, 1H), 7.38 (m, 1H), 7.32 (m, 1H).
$^{13}$C NMR (126 MHz, DMSO-d$_6$) δ 164.5, 146.4, 138.0, 137.4, 134.5, 130.7, 130.5, 129.5, 125.7, 125.3, 124.9, 123.7, 118.4, 111.7, 110.9, 97.5.

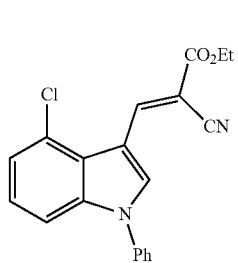

JXL093

Ethyl (E)-3-(4-chloro-1-phenyl-1H-indol-3-yl)-2-cyanoacrylate (JXL093)

$^{1}$H NMR (500 MHz, CDCl$_3$) δ 9.51 (s, 1H), 8.78 (s, 1H), 7.59 (m, 2H), 7.51 (m, 3H), 7.40 (dd, J=8.3, 0.8 Hz, 1H), 7.32 (dd, J=7.7, 0.8 Hz, 1H), 7.22 (app. t, J=8.0 Hz, 1H), 4.38 (q, J=7.1 Hz, 2H), 1.40 (t, J=7.1 Hz, 3H).

$^{13}$C NMR (126 MHz, CDCl$_3$) δ 163.6, 147.6, 138.1, 137.4, 134.2, 130.1, 129.0, 126.9, 125.3, 124.6, 124.5, 124.3, 118.0, 111.8, 110.6, 96.0, 62.1, 14.3.

Experimental Details for the Synthesis of JXL020

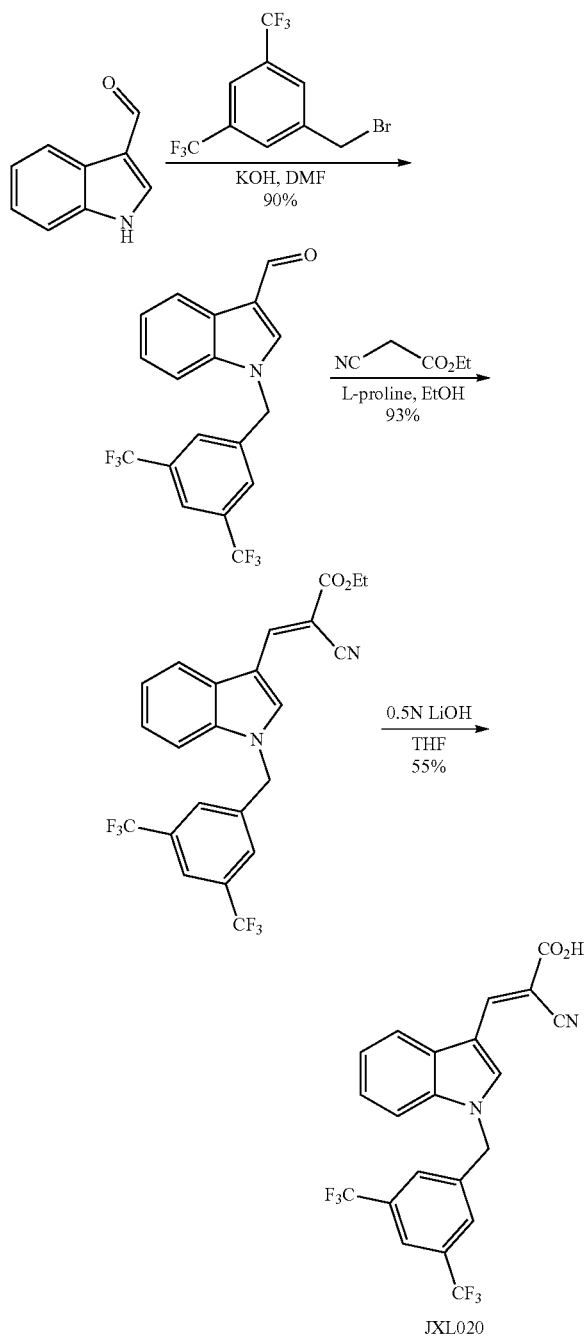

To the solution of indole-3-carboxaldehyde (3 mmol, 435 mg) in dry DMF (6 mL) were added 3,5-bis(trifluoromethyl) benzyl bromide (1.2 equiv, 3.6 mmol, 660 µL) and KOH (1.2 equiv, 3.6 mmol, 200 mg) at 0° C. The reaction mixture was stirred at 21° C. for 2 h. After the reaction completion shown by TLC, water (6 mL) was added to the reaction vial. The reaction mixture was extracted by dichloromethane (15 mL×3). The combined organic layer was dried by sodium sulfate and concentrated. The residue was purified by flash column chromatography (hexanes/EtOAc=8:1) to provide the desired product. yield: 90%, 1001.7 mg.

To the solution of 1-(3,5-bis(trifluoromethyl)benzyl)-1H-indole-3-carbaldehyde (1 mmol, 371 mg) in ethanol (1 mL) were added ethyl 2-cyanoacetate (1.3 equiv, 1.3 mmol, 140 µL) and L-proline (40 mol %, 0.4 mmol, 58 mg). The reaction was stirred at 21° C. for 12 h and yellow solid precipitated gradually. After completion of the reaction, ice-cold water (2 mL) was added into the reaction vial. The solid was separated by Buchner funnel filtration and washed with water (2 mL×3) and dried to afford the desired product. yield: 93%, 433 mg. To the solution of (E)-ethyl 3-(1-(3,5-bis(trifluoromethyl)benzyl)-1H-indol-3-yl)-2-cyanoacrylate (0.21 mmol, 100 mg) in THF (2 mL) was added 0.5N LiOH solution (3 equiv, 0.4 mmol, 0.8 mL). The reaction mixture was stirred at 21° C. for 1 h. After reaction completion shown by TLC, THF was evaporated. Concentrated HCl was added dropwise to acidify the reaction mixture until pH was lower than 1, meanwhile yellow solid precipitated. Ice-cold water (5 mL) was added to the reaction mixture and the solid was separated by Buchner funnel filtration and washed with water (5 mL×3). After dried by vacuum, the solid was washed by 2 mL of solvent mixture (hexanes/EtOAc=5:1) 5 to 10 times and monitored by TLC until non-polar impurities disappear (The non-polar compound was the retro-Aldol condensation product, which can be recovered from the filtrate). Finally, the purity of the product was checked by NMR. yield: 55%, 52 mg.

(E)-3-(1-(3,5-Bis(trifluoromethyl)benzyl)-1H-indol-3-yl)-2-cyanoacrylic Acid (JXL020)

$^1$H NMR (500 MHz, DMSO-d$_6$) δ 13.37 (br. s, 1H), 8.75 (s, 1H), 8.48 (s, 1H), 7.99 (m, 4H), 7.65 (s, 1H), 7.28 (m, 2H), 5.83 (s, 2H).

$^{13}$C NMR (126 MHz, DMSO-d$_6$) δ 164.7, 145.7, 140.3, 136.3, 134.8, 131.1, 130.8 (q, J=31.1 Hz), 128.9, 128.7, 127.9, 124.8, 124.3, 122.9 (q, J=273.4 Hz), 122.2, 119.3, 118.3, 95.6, 49.2.

The following compounds were synthesized by a route similar to that described for JXL020: JXL008, JXL009, JXL010, JXL011, JXL015, JXL016, JXL017, JXL018, JXL019, JXL036, JXL037, JXL038, JXL039, JXL040, JXL041, JXL050, JXL051, JXL052, JXL053, JXL054, JXL055, JXL56, JXL057, JXL058, JXL059, JXL060, JXL061, JXL062, JXL063, JXL064, JXL065, JXL066, JXL068, JXL069, JXL072, JXL073, JXL076, JXL077, JXL078, JXL081, JXL082, JXL087, JXL088, JXL089, JXL090, JXL091.

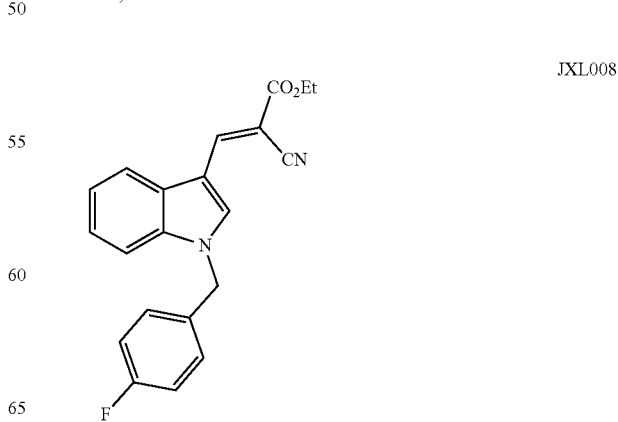

JXL008

Ethyl (E)-2-cyano-3-(1-(4-fluorobenzyl)-1H-indol-3-yl)acrylate (JXL008)

$^1$H NMR (500 MHz, CDCl$_3$) δ 8.60 (app. s, 2H), 7.85 (d, J=6.8 Hz, 1H), 7.32 (m, 3H), 7.15 (m, 2H), 7.03 (app. t, 2H), 5.39 (s, 2H), 4.37 (q, J=7.1 Hz, 2H), 1.40 (t, J=7.1 Hz, 3H).

$^{13}$C NMR (126 MHz, CDCl$_3$) δ 163.7, 162.5 (d, J$_{c-f}$=247.7 Hz), 145.7, 136.1, 133.8, 130.9, 128.6, 128.5, 124.0, 122.7, 118.6, 118.0, 116.0 (d, J$_{c-f}$=21.9 Hz), 110.9, 110.4, 94.6, 61.9, 50.7, 14.2.

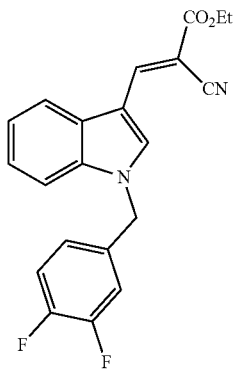

JXL009

Ethyl (E)-2-cyano-3-(1-(3,4-difluorobenzyl)-1H-indol-3-yl)acrylate (JXL009)

$^1$H NMR (500 MHz, CDCl$_3$) δ 8.60 (s, 1H), 8.59 (s, 1H), 7.86 (d, J=7.8 Hz, 1H), 7.33 (m, 2H), 7.28 (s, 1H), 7.13 (m, 1H), 6.95 (m, 1H), 6.89 (m, 1H), 5.39 (s, 2H), 4.38 (q, J=7.1 Hz, 2H), 1.40 (t, J=7.1 Hz, 3H).

$^{13}$C NMR (126 MHz, CDCl$_3$) δ 163.7, 150.7 (dd, J=251.2, 13.2 Hz), 150.2 (dd, J=250.4, 12.6 Hz), 145.7, 136.1, 133.7, 132.3, 128.6, 124.3, 122.9, 122.7, 120.0, 118.8, 118.0 (d, J=17.5 Hz), 115.9 (d, J=18.0 Hz), 110.8, 110.6, 95.2, 62.1, 50.4, 14.4.

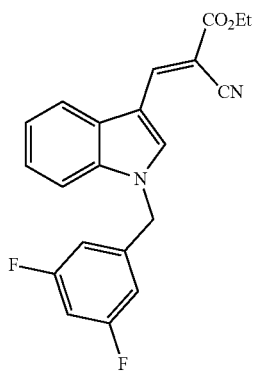

JXL010

Ethyl (E)-2-cyano-3-(1-(3,5-difluorobenzyl)-1H-indol-3-yl)acrylate (JXL010)

$^1$H NMR (500 MHz, CDCl$_3$) δ 8.61 (s, 1H), 8.59 (s, 1H), 7.87 (d, J=7.1 Hz, 1H), 7.33 (m, 2H), 7.26 (d, J=7.2 Hz, 1H), 6.75 (app. t, J=8.7 Hz, 1H), 6.64 (app. d, J=5.7 Hz, 2H), 5.41 (s, 2H), 4.38 (q, J=7.1 Hz, 2H), 1.40 (t, J=7.1 Hz, 3H).

$^{13}$C NMR (126 MHz, CDCl$_3$) δ 163.6, 163.3 (dd, J$_{c-f}$=251.0, 12.5 Hz), 145.5, 139.2, 136.0, 133.6, 128.4, 124.3, 122.9, 118.7, 118.0, 110.7, 110.6, 109.5 (dd, J$_{c-f}$=19.9, 6.4 Hz), 103.8 (t, J$_{c-f}$=25.2 Hz), 95.3, 62.0, 50.4, 14.2.

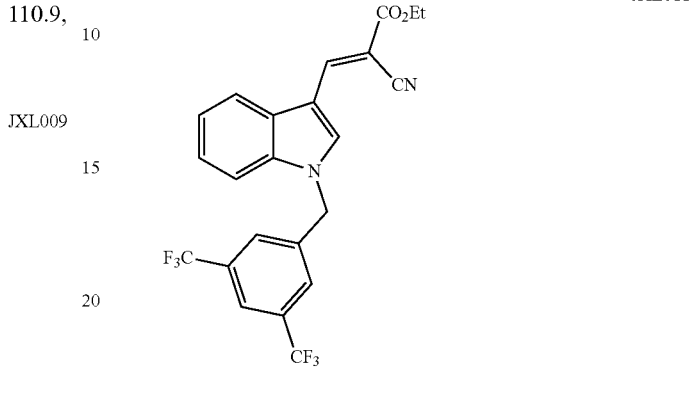

Ethyl (E)-3-(1-(3,5-bis(trifluoromethyl)benzyl)-1H-indol-3-yl)-2-cyanoacrylate (JXL011)

$^1$H NMR (500 MHz, CDCl$_3$) δ 8.62 (s, 1H), 8.61 (s, 1H), 7.90 (d, J=7.7 Hz, 1H), 7.85 (s, 1H), 7.57 (s, 2H), 7.35 (m, 2H), 7.23 (d, J=7.8 Hz, 1H), 5.56 (s, 2H), 4.38 (q, J=7.1 Hz, 2H), 1.40 (t, J=7.1 Hz, 3H).

$^{13}$C NMR (126 MHz, CDCl$_3$) δ 163.6, 145.6, 138.1, 136.0, 133.4, 132.7 (q, J=33.8 Hz), 128.6, 126.8, 124.7, 123.2, 122.9 (q, J=273.4 Hz), 122.6, 119.0, 118.0, 111.2, 110.4, 95.9, 62.1, 50.5, 14.3.

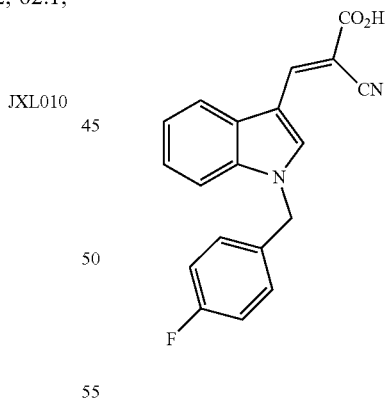

JXL015

(E)-2-Cyano-3-(1-(4-fluorobenzyl)-1H-indol-3-yl) acrylic Acid (JXL015)

$^1$H NMR (500 MHz, DMSO-d$_6$) δ 8.64 (s, 1H), 8.46 (s, 1H), 7.93 (d, J=7.1 Hz, 1H), 7.61 (d, J=7.3 Hz, 1H), 7.33 (m, 2H), 7.26 (m, 2H), 7.16 (m, 2H), 5.60 (s, 2H).

$^{13}$C NMR (126 MHz, DMSO-d$_6$) δ 164.8, 162.0 (d, J$_{c-f}$=244.3 Hz), 145.6, 136.4, 134.6, 133.1, 130.0, 128.0, 124.1, 122.8, 119.2, 118.5, 116.0 (d, J$_{c-f}$=21.7 Hz), 112.0, 109.8, 95.0, 49.6.

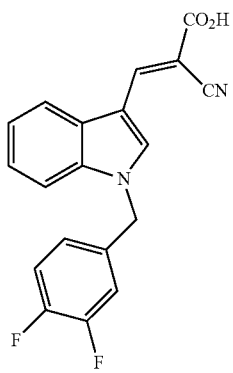

(E)-2-Cyano-3-(1-(3,4-difluorobenzyl)-1H-indol-3-yl)acrylic Acid (JXL016)

$^1$H NMR (500 MHz, DMSO-d$_6$) δ 13.34 (br. s, 1H), 8.62 (s, 1H), 8.47 (s, 1H), 7.94 (d, J=7.3 Hz, 1H), 7.61 (d, J=7.6 Hz, 1H), 7.40 (m, 2H), 7.27 (m, 2H), 7.10 (br. s, 1H), 5.61 (s, 2H).

$^{13}$C NMR (126 MHz, DMSO-d$_6$) δ 164.8, 149.7 (dd, J=253.3, 13.6 Hz), 149.4 (dd, J$_{c-f}$=246.3, 11.6 Hz), 145.7, 136.4, 134.7, 134.5, 128.0, 124.7 (dd, J$_{c-f}$=5.9, 3.0 Hz), 124.2, 122.8, 119.2, 118.4, 118.3 (d, J$_{c-f}$=17.0 Hz), 117.1 (d, J$_{c-f}$=17.6 Hz), 112.0, 109.9, 95.0, 49.3.

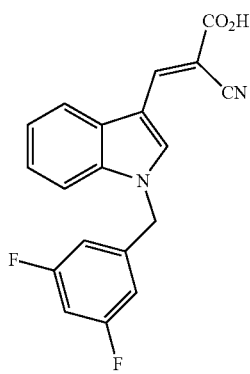

(E)-2-Cyano-3-(1-(3,5-difluorobenzyl)-1H-indol-3-yl)acrylic acid (JXL017)

$^1$H NMR (500 MHz, DMSO-d$_6$) δ 8.67 (s, 1H), 8.48 (s, 1H), 7.95 (d, J=4.8 Hz, 1H), 7.59 (d, J=4.4 Hz, 1H), 7.27 (m, 2H), 7.15 (s, 1H), 6.98 (br. s, 2H), 5.65 (s, 2H).

$^{13}$C NMR (126 MHz, DMSO-d$_6$) δ 164.8, 162.9 (dd, J$_{c-f}$=247.0, 12.8 Hz), 145.6, 141.4, 136.4, 134.8, 128.0, 124.2, 122.9, 119.3, 118.4, 111.9, 111.0 (d, J$_{c-f}$=26.1 Hz), 110.8, 103.8 (t, J$_{c-f}$=26.5 Hz), 95.5, 49.5.

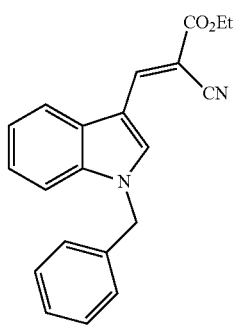

Ethyl (E)-3-(1-benzyl-1H-indol-3-yl)-2-cyanoacrylate (JXL018)

$^1$H NMR (500 MHz, CDCl$_3$) δ 8.61 (s, 1H), 8.60 (s, 1H), 7.85 (d, J=7.9 Hz, 1H), 7.33 (m, 6H), 7.17 (m, 2H), 5.42 (s, 2H), 4.37 (q, J=7.1 Hz, 2H), 1.40 (t, J=7.1 Hz, 3H).

$^{13}$C NMR (126 MHz, CDCl$_3$) δ 163.8, 145.7, 136.2, 135.1, 134.0, 129.0, 128.5, 128.2, 126.8, 124.0, 122.6, 118.5, 118.1, 111.0, 110.3, 94.3, 61.8, 51.4, 14.2.

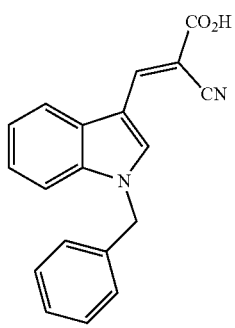

(E)-3-(1-Benzyl-1H-indol-3-yl)-2-cyanoacrylic acid (JXL019)

$^1$H NMR (500 MHz, DMSO-d$_6$) δ 13.34 (br. s, 1H), 8.65 (s, 1H), 8.48 (s, 1H), 7.93 (d, J=6.9 Hz, 1H), 7.60 (d, J=6.8 Hz, 1H), 7.25 (m, 7H), 5.62 (s, 2H).

$^{13}$C NMR (126 MHz, DMSO-d$_6$) δ 164.8, 145.7, 136.8, 136.5, 134.7, 129.1, 128.2, 127.6, 124.0, 122.7, 120.0, 119.2, 118.5, 112.1, 109.7, 94.7, 50.4.

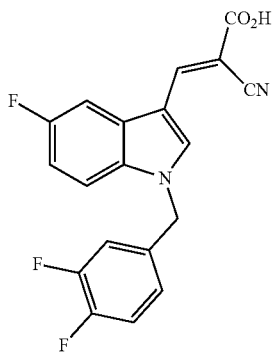

(E)-2-Cyano-3-(1-(3,4-difluorobenzyl)-5-fluoro-1H-indol-3-yl)acrylic acid (JXL036)

$^1$H NMR (500 MHz, DMSO-d$_6$) δ 8.69 (s, 1H), 8.47 (s, 1H), 7.84 (d, J=9.6 Hz, 1H), 7.63 (dd, J=8.9, 4.3 Hz, 1H), 7.41 (m, 2H), 7.14 (m, 2H), 5.61 (s, 2H).
$^{13}$C NMR (126 MHz, DMSO-d$_6$) δ 164.9, 159.4 (d, J$_{c-f}$=237.3 Hz), 149.8 (dd, J$_{c-f}$=247.1, 12.7 Hz), 149.5 (dd, J$_{c-f}$=246.6, 12.3 Hz), 146.0, 136.1, 134.5, 133.1, 129.1, 125.0, 118.5, 118.4, 117.4, 113.6, 112.5 (d, J$_{c-f}$=26.2 Hz), 110.1, 105.2 (d, J$_{c-f}$=25.1 Hz), 95.5, 49.7.

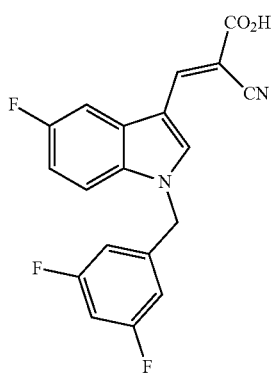

(E)-2-Cyano-3-(1-(3,5-difluorobenzyl)-5-fluoro-1H-indol-3-yl)acrylic acid (JXL037)

$^1$H NMR (500 MHz, DMSO-d$_6$) δ 8.71 (s, 1H), 8.48 (s, 1H), 7.85 (dd, J=9.6, 2.0 Hz, 1H), 7.62 (dd, J=8.9, 4.3 Hz, 1H), 7.16 (m, 2H), 7.00 (app. d, J=6.2 Hz, 2H), 5.65 (s, 2H).
$^{13}$C NMR (126 MHz, DMSO-d$_6$) δ 164.9, 163.0 (d, J$_{c-f}$=247.7 Hz), 159.3 (d, J$_{c-f}$=237.6 Hz), 145.9, 141.4, 136.3, 133.2, 129.1, 118.5, 113.6, 112.6 (d, J$_{c-f}$=26.3 Hz), 111.3, 110.2, 105.3 (d, J$_{c-f}$=24.9 Hz), 104.0 (t, J$_{c-f}$=25.2 Hz), 95.9, 49.8.

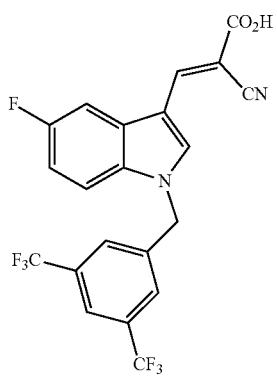

(E)-3-(1-(3,5-Bis(trifluoromethyl)benzyl)-5-fluoro-1H-indol-3-yl)-2-cyanoacrylic acid (JXL038)

$^1$H NMR (500 MHz, DMSO-d$_6$) δ 8.80 (s, 1H), 8.49 (s, 1H), 8.06 (s, 1H), 8.04 (s, 2H), 7.86 (dd, J=9.6, 2.1 Hz, 1H), 7.69 (dd, J=8.9, 4.3 Hz, 1H), 7.17 (dt, J=9.0, 2.2 Hz, 1H), 5.83 (s, 2H).
$^{13}$C NMR (126 MHz, DMSO-d$_6$) δ 164.8, 159.3 (d, J$_{c-f}$=237.5 Hz), 145.9, 140.3, 136.2, 133.1, 131.1 (q, J$_{c-f}$=33.1 Hz), 129.1, 123.6 (q, J$_{c-f}$=272.2 Hz), 118.4, 113.5, 112.7, 112.5, 110.4, 105.5, 105.3, 96.1, 49.6.

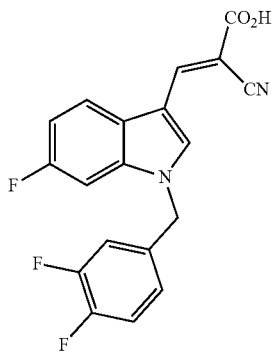

E)-2-Cyano-3-(1-(3,4-difluorobenzyl)-6-fluoro-1H-indol-3-yl)acrylic acid (JXL039)

$^1$H NMR (500 MHz, DMSO-d$_6$) δ 8.64 (s, 1H), 8.46 (s, 1H), 7.99 (dd, J=8.7, 5.1 Hz, 1H), 7.58 (dd, J=9.8, 1.8 Hz, 1H), 7.43 (m, 2H), 7.12 (m, 2H), 5.57 (s, 2H).
$^{13}$C NMR (126 MHz, DMSO-d$_6$) δ 164.8, 160.3 (d, J$_{c-f}$=239.3 Hz), 149.8 (dd, J$_{c-f}$=239.3, 25.2 Hz), 149.6 (dd, J$_{c-f}$=246.3, 25.2 Hz), 145.8, 136.8, 135.3, 134.5, 125.1, 125.0, 124.6, 121.1, 118.5, 117.5, 111.3 (d, J$_{c-f}$=23.9 Hz), 110.2, 98.7 (d, J$_{c-f}$=26.5 Hz), 96.2, 49.4.

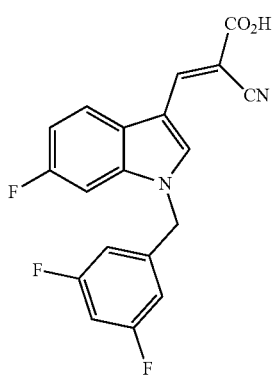

(E)-2-Cyano-3-(1-(3,5-difluorobenzyl)-6-fluoro-1H-indol-3-yl)acrylic acid (JXL040)

$^1$H NMR (500 MHz, DMSO-d$_6$) δ 8.65 (s, 1H), 8.46 (s, 1H), 8.00 (dd, J=8.6, 5.2 Hz, 1H), 7.57 (d, J=9.7 Hz, 1H), 7.15 (m, 2H), 7.03 (s, 1H), 7.02 (s, 1H), 5.62 (s, 2H).
$^{13}$C NMR (126 MHz, DMSO-d$_6$) δ 164.8, 163.0 (d, J$_{c-f}$=239.4 Hz), 162.9 (d, J$_{c-f}$=248.6 Hz), 160.4 (d, J$_{c-f}$=239.4 Hz), 145.5, 141.3, 136.8, 135.2, 124.6, 121.1, 118.4, 111.3, 111.1, 110.3, 104.0 (t, J$_{c-f}$=25.2 Hz), 98.7 (d, J$_{c-f}$=26.5 Hz), 96.9, 49.6.

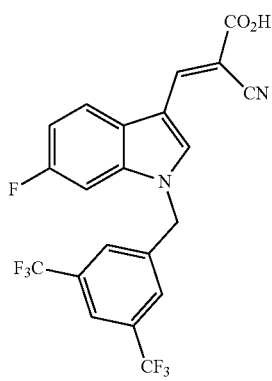

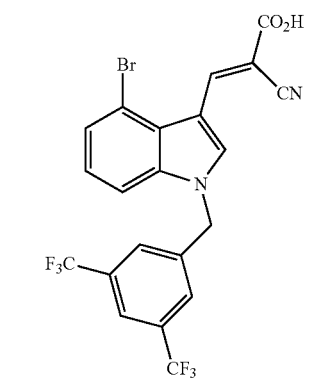

(E)-3-(1-(3,5-Bis(trifluoromethyl)benzyl)-6-fluoro-1H-indol-3-yl)-2-cyanoacrylic Acid (JXL041)

$^1$H NMR (500 MHz, DMSO-d$_6$) δ 8.74 (s, 1H), 8.48 (s, 1H), 8.06 (app. s, 3H), 8.01 (dd, J=8.7, 5.1 Hz, 1H), 7.66 (dd, J=9.8, 2.0 Hz, 1H), 7.13 (dt, J=9.3, 2.1 Hz, 1H), 5.78 (s, 2H).

$^{13}$C NMR (126 MHz, DMSO-d$_6$) δ 164.7, 159.9 (d, J$_{c-f}$=264.6 Hz), 145.8, 140.2, 136.8, 135.3, 131.1 (q, J$_{c-f}$=33.3 Hz), 129.1, 124.5, 123.6 (q, J$_{c-f}$=273.7 Hz), 122.5, 121.2, 118.4, 111.4 (d, J$_{c-f}$=25.2 Hz), 110.4, 98.6 (d, J$_{c-f}$=27.2 Hz), 96.7, 49.4.

(E)-3-(1-(3,5-Bis(trifluoromethyl)benzyl)-4-bromo-1H-indol-3-yl)-2-cyanoacrylic Acid (JXL051)

$^1$H NMR (500 MHz, DMSO-d$_6$) δ 9.37 (s, 1H), 8.91 (s, 1H), 8.07 (app. s, 3H), 7.77 (d, J=8.2 Hz, 1H), 7.51 (d, J=7.6 Hz, 1H), 7.23 (t, J=8.0 Hz, 1H), 5.85 (s, 2H).

$^{13}$C NMR (126 MHz, DMSO-d$_6$) δ 164.7, 146.3, 140.0, 138.0, 135.8, 131.0 (q, J$_{c-f}$=33.1 Hz), 129.1, 127.9, 125.4, 124.9, 123.7 (q, J$_{c-f}$=273.2 Hz), 122.5, 118.2, 113.6, 122.1, 110.2, 96.6, 49.5.

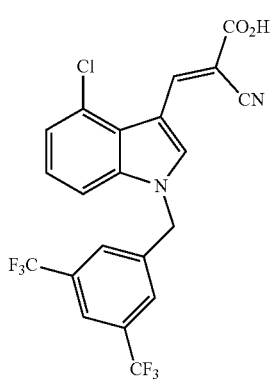

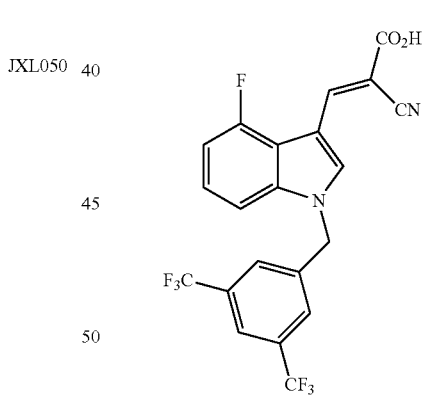

(E)-3-(1-(3,5-Bis(trifluoromethyl)benzyl)-4-chloro-1H-indol-3-yl)-2-cyanoacrylic Acid (JXL050)

$^1$H NMR (500 MHz, DMSO-d$_6$) δ 9.20 (s, 1H), 8.90 (s, 1H), 8.06 (m, 3H), 7.72 (d, J=7.5 Hz, 1H), 7.32 (m, 2H), 5.86 (s, 2H).

$^{13}$C NMR (126 MHz, DMSO-d$_6$) δ 164.7, 146.7, 140.0, 138.0, 135.6, 131.1 (q, J$_{c-f}$=33.1 Hz), 129.1, 125.6, 125.1, 124.7, 124.5, 123.7, 123.6 (q, J$_{c-f}$=273.7 Hz), 122.5, 111.6, 109.9, 96.7, 49.6.

(E)-3-(1-(3,5-Bis(trifluoromethyl)benzyl)-4-fluoro-1H-indol-3-yl)-2-cyanoacrylic Acid (JXL052)

$^1$H NMR (500 MHz, DMSO-d$_6$) δ 8.80 (s, 1H), 8.58 (s, 1H), 8.05 (app. s, 3H), 7.54 (d, J=8.2 Hz, 1H), 7.29 (d, J=12.9 Hz, 1H), 7.09 (dd, J=11.1, 8.2 Hz, 1H), 5.85 (s, 2H).

$^{13}$C NMR (126 MHz, DMSO-d$_6$) δ 164.5, 155.7 (d, J$_{c-f}$=239.4 Hz), 146.5, 140.1, 138.8, 134.5, 131.1 (q, J$_{c-f}$=33.0 Hz), 129.0, 125.1 (d, J$_{c-f}$=7.6 Hz), 124.7, 123.6 (q, J$_{c-f}$=273.5 Hz), 122.5, 118.1, 116.1 (d, J$_{c-f}$=18.5 Hz), 108.8, 108.5, 97.2, 49.7.

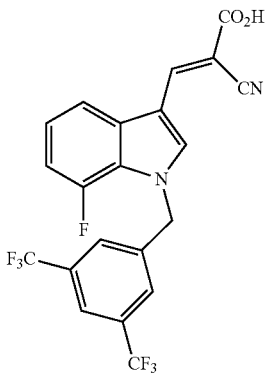

(E)-3-(1-(3,5-Bis(trifluoromethyl)benzyl)-7-fluoro-1H-indol-3-yl)-2-cyanoacrylic Acid (JXL053)

$^{1}$H NMR (500 MHz, DMSO-d$_{6}$) δ 8.73 (br. s, 1H), 8.48 (br. s, 1H), 8.06 (br. s, 1H), 7.89 (br. s, 2H), 7.78 (br. s, 1=7.4 Hz, 1H), 7.22 (br. s, 1H), 7.10 (br. s, 1H), 5.89 (s, 2H).

$^{13}$C NMR (126 MHz, DMSO-d$_{6}$) δ 164.6, 159.7 (d, $J_{c-f}$=245.7 Hz), 145.6, 141.0, 136.2, 132.1, 130.0 (q, $J_{c-f}$=33.0 Hz), 128.4, 123.9, 123.8, 123.6 (q, $J_{c-f}$=273.3 Hz), 122.4 (d, $J_{c-f}$=18.9 Hz), 118.1, 115.8, 110.6, 110.2 (d, $J_{c-f}$=18.9 Hz), 97.3, 52.0.

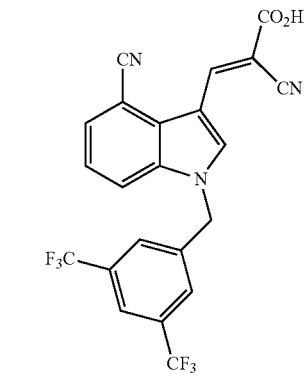

(E)-3-(1-(3,5-Bis(trifluoromethyl)benzyl)-4-cyano-1H-indol-3-yl)-2-cyanoacrylic Acid (JXL055)

$^{1}$H NMR (500 MHz, DMSO-d$_{6}$) δ 9.03 (s, 1H), 9.00 (s, 1H), 8.09 (m, 4H), 7.80 (d, J=7.3 Hz, 1H), 7.47 (t, J=7.8 Hz, 1H), 5.90 (s, 2H).

$^{13}$C NMR (126 MHz, DMSO-d$_{6}$) δ 164.4, 144.4, 139.9, 136.7, 131.1 (q, $J_{c-f}$=330.0 Hz), 129.7, 129.2, 126.6, 124.3, 123.6 (q, $J_{c-f}$=273.7 Hz), 122.7, 118.6, 117.9, 117.8, 109.3, 101.7, 98.1, 49.5.

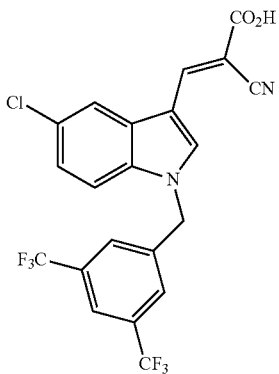

(E)-3-(1-(3,5-Bis(trifluoromethyl)benzyl)-5-chloro-1H-indol-3-yl)-2-cyanoacrylic Acid (JXL054)

$^{1}$H NMR (500 MHz, DMSO-d$_{6}$) δ 8.78 (s, 1H), 8.51 (s, 1H), 8.12 (s, 1H), 8.06 (s, 1H), 8.03 (s, 2H), 7.70 (d, J=7.4 Hz, 1H), 7.33 (d, J=7.0 Hz, 1H), 5.83 (s, 2H).

$^{13}$C NMR (126 MHz, DMSO-d$_{6}$) δ 164.7, 145.7, 140.2, 135.9, 135.1, 131.1 (q, $J_{c-f}$=33.0 Hz), 129.3, 129.0, 127.9, 124.4, 123.6 (q, $J_{c-f}$=274.0 Hz), 122.5, 119.5, 118.4, 113.6, 109.9, 96.9, 49.5.

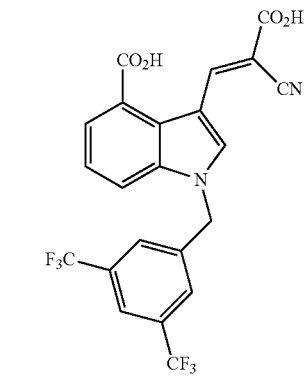

(E)-1-(3,5-Bis(trifluoromethyl)benzyl)-3-(2-carboxy-2-cyanovinyl)-1H-indole-4-carboxylic Acid (JXL056)

$^{1}$H NMR (500 MHz, DMSO-d$_{6}$) δ 9.26 (br. s, 1H), 8.88 (br. s, 1H), 8.05 (app. s, 3H), 7.94 (br. s, 1H), 7.76 (br. s, 1H), 7.37 (br. s, 1H), 5.85 (s, 2H).

$^{13}$C NMR (126 MHz, DMSO-d$_{6}$) δ 169.3, 165.0, 150.6, 140.2, 137.7, 136.0, 131.1 (q, $J_{c-f}$=33.0 Hz), 129.0, 125.9, 125.2, 124.7, 123.6 (q, $J_{c-f}$=273.7 Hz), 123.5, 122.5, 118.3, 116.1, 110.1, 96.4, 49.3.

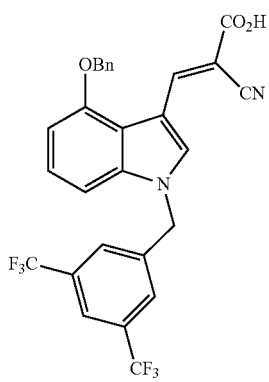

(E)-3-(4-(Benzyloxy)-1-(3,5-bis(trifluoromethyl) benzyl)-1H-indol-3-yl)-2-cyanoacrylic Acid (JXL057)

$^1$H NMR (500 MHz, DMSO-d$_6$) δ 9.15 (s, 1H), 8.72 (s, 1H), 8.04 (s, 1H), 7.99 (s, 2H), 7.54 (br. s, 3H), 7.37 (br. s, 2H), 7.28 (m, 2H), 6.95 (s, 1H), 5.81 (s, 2H), 5.28 (s, 2H).

$^{13}$C NMR (126 MHz, DMSO-d$_6$) δ 165.0, 153.7, 148.6, 140.5, 137.9, 133.4, 131.2 (q, J$_{c-f}$=32.8 Hz), 128.9, 128.8, 128.1, 127.5, 125.4, 124.7, 123.6 (q, J$_{c-f}$=273.7 Hz), 122.3, 118.5, 117.0, 110.5, 105.6, 105.2, 95.5, 70.0, 49.5.

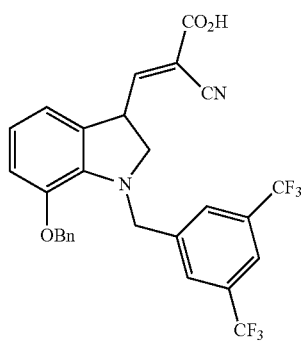

(E)-3-(7-(Benzyloxy)-1-(3,5-bis(trifluoromethyl) benzyl)-1H-indol-3-yl)-2-cyanoacrylic Acid (JXL059)

$^1$H NMR (500 MHz, DMSO-d$_6$) δ 8.61 (br. s, 1H), 8.45 (br. s, 1H), 7.97 (br. s, 1H), 7.60 (br. s, 2H), 7.51 (br. s, 1H), 7.25 (br. s, 2H), 7.16 (br. s, 2H), 6.91 (br. s, 1H), 5.94 (s, 2H), 5.13 (s, 2H).

$^{13}$C NMR (126 MHz, DMSO-d$_6$) δ 164.8, 146.6, 145.7, 142.3, 136.6, 135.4, 130.7 (q, J$_{c-f}$=32.8 Hz), 130.5, 128.8, 128.4, 128.0, 127.5, 125.7, 124.1, 123.6 (q, J$_{c-f}$=273.7 Hz), 121.8, 118.3, 111.8, 110.3, 107.1, 96.2, 70.3, 52.4.

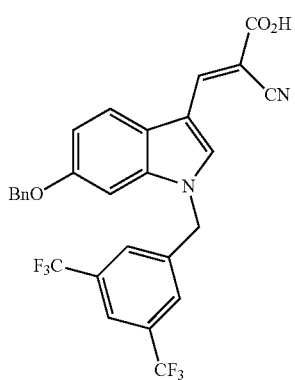

(E)-3-(6-(Benzyloxy)-1-(3,5-bis(trifluoromethyl) benzyl)-1H-indol-3-yl)-2-cyanoacrylic acid (JXL058)

$^1$H NMR (500 MHz, DMSO-d$_6$) δ 8.63 (s, 1H), 8.43 (s, 1H), 8.05 (s, 1H), 8.03 (s, 2H), 7.86 (d, J=8.5 Hz, 1H), 7.32 (m, 6H), 6.97 (d, J=8.3 Hz, 1H), 5.77 (s, 2H), 5.09 (s, 2H).

$^{13}$C NMR (126 MHz, DMSO-d$_6$) δ 165.0, 156.7, 146.1, 140.5, 137.5, 137.3, 134.3, 131.0 (q, J$_{c-f}$=32.8 Hz), 128.9, 128.8, 128.3, 128.2, 126.9, 123.6 (q, J$_{c-f}$=273.4 Hz), 122.4, 121.9, 118.5, 113.3, 110.5, 96.8, 95.6, 70.2, 49.2.

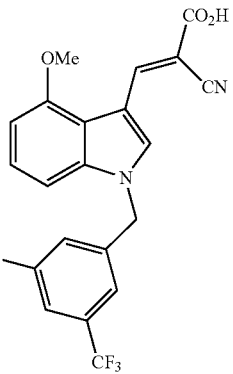

(E)-3-(1-(3,5-Bis(trifluoromethyl)benzyl)-4-methoxy-1H-indol-3-yl)-2-cyanoacrylic Acid (JXL060)

$^1$H NMR (500 MHz, DMSO-d$_6$) δ 8.99 (s, 1H), 8.71 (s, 1H), 8.05 (s, 1H), 8.00 (s, 2H), 7.24 (app. s, 2H), 6.82 (d, J=6.0 Hz, 1H), 5.81 (s, 2H), 3.92 (s, 3H).

$^{13}$C NMR (126 MHz, DMSO-d$_6$) δ 165.0, 154.8, 148.6, 140.5, 137.8, 133.3, 131.0 (q, J$_{c-f}$=32.8 Hz), 128.9, 125.4, 123.6 (q, J$_{c-f}$=273.7 Hz), 122.5, 118.5, 116.8, 110.5, 105.0, 104.3, 95.3, 56.2, 49.5.

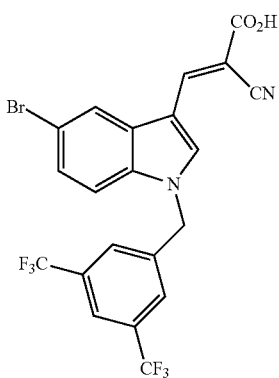

JXL061

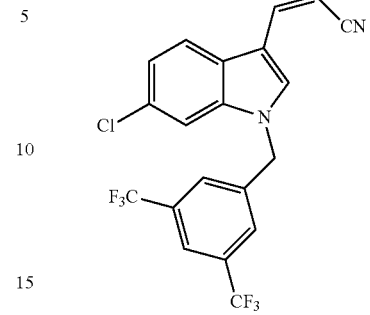

JXL063

(E)-3-(1-(3,5-Bis(trifluoromethyl)benzyl)-5-bromo-1H-indol-3-yl)-2-cyanoacrylic Acid (JXL061)

¹H NMR (500 MHz, DMSO-d₆) δ 8.75 (s, 1H), 8.49 (s, 1H), 8.25 (s, 1H), 8.06 (s, 1H), 8.02 (m, 3H), 7.64 (app. s, 1H), 7.44 (app. s, 1H), 5.82 (s, 2H).

¹³C NMR (126 MHz, DMSO-d₆) δ 164.7, 145.3, 140.3, 135.5, 135.3, 131.1 (q, $J_{c-f}$=32.8 Hz), 129.8, 128.9, 127.0, 124.7, 123.6 (q, $J_{c-f}$=274.0 Hz), 122.5, 122.3, 118.5, 113.9, 109.9, 97.7, 49.5.

(E)-3-(1-(3,5-Bis(trifluoromethyl)benzyl)-6-chloro-1H-indol-3-yl)-2-cyanoacrylic Acid (JXL063)

¹H NMR (500 MHz, DMSO-d₆) δ 8.75 (s, 1H), 8.47 (s, 1H), 8.05 (m, 3H), 8.00 (d, J=7.4 Hz, 1H), 7.89 (s, 1H), 7.28 (d, J=6.5 Hz, 1H), 5.81 (s, 2H).

¹³C NMR (126 MHz, DMSO-d₆) δ 164.7, 145.6, 140.2, 137.0, 135.4, 131.1 (q, $J_{c-f}$=32.8 Hz), 129.2, 129.0, 126.7, 123.6 (q, $J_{c-f}$=274.0 Hz), 123.3, 122.5, 121.2, 118.2, 111.9, 110.3, 97.0, 49.3.

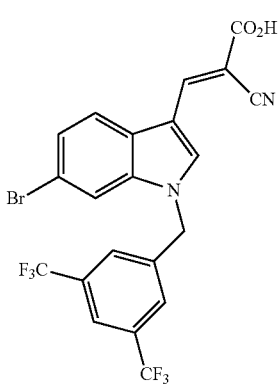

JXL062

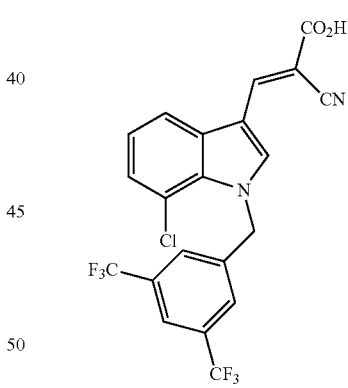

JXL064

(E)-3-(1-(3,5-Bis(trifluoromethyl)benzyl)-6-bromo-1H-indol-3-yl)-2-cyanoacrylic Acid (JXL062)

¹H NMR (500 MHz, DMSO-d₆) δ 8.72 (s, 1H), 8.47 (s, 1H), 8.06 (s, 2H), 8.03 (s, 1H), 7.94 (d, J=8.2 Hz, 1H), 7.39 (d, J=7.9 Hz, 1H), 5.81 (s, 2H).

¹³C NMR (126 MHz, DMSO-d₆) δ 164.7, 145.6, 140.2, 137.4, 135.3, 131.1 (q, $J_{c-f}$=32.8 Hz), 129.1, 127.0, 125.9, 123.6 (q, $J_{c-f}$=274.0 Hz), 122.5, 121.5, 118.2, 117.2, 114.8, 110.3, 96.9, 49.3.

(E)-3-(1-(3,5-Bis(trifluoromethyl)benzyl)-7-chloro-1H-indol-3-yl)-2-cyanoacrylic Acid (JXL064)

¹H NMR (500 MHz, DMSO-d₆) δ 8.69 (s, 1H), 8.50 (s, 1H), 8.03 (s, 1H), 7.97 (d, J=7.5 Hz, 1H), 7.73 (s, 2H), 7.32 (d, J=7.1 Hz, 1H), 7.25 (m, 1H), 6.14 (s, 2H).

¹³C NMR (126 MHz, DMSO-d₆) δ 164.5, 145.1, 142.1, 136.9, 131.5, 131.2 (q, $J_{c-f}$=32.8 Hz), 127.6, 126.1, 124.1, 123.6 (q, $J_{c-f}$=274.0 Hz), 122.5, 122.0, 118.8, 118.0, 116.9, 110.3, 97.9, 51.8.

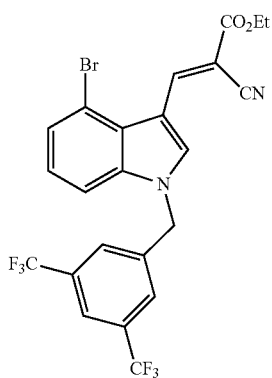

Ethyl (E)-3-(1-(3,5-bis(trifluoromethyl)benzyl)-4-bromo-1H-indol-3-yl)-2-cyanoacrylate (JXL065)

¹H NMR (500 MHz, DMSO-d₆) δ 9.67 (s, 1H), 8.71 (s, 1H), 7.86 (s, 1H), 7.56 (s, 2H), 7.52 (d, J=7.4 Hz, 1H), 7.17 (m, 2H), 5.55 (s, 2H), 4.37 (q, J=7.1 Hz, 2H), 1.40 (t, J=7.1 Hz, 3H).

¹³C NMR (126 MHz, DMSO-d₆) δ 163.4, 146.9, 137.6, 137.4, 134.3, 132.7 (q, $J_{c-f}$=33.9 Hz), 128.2, 126.7, 125.6, 125.1, 122.8 (q, $J_{c-f}$=273.4 Hz), 122.7, 118.0, 114.9, 111.8, 109.9, 96.3, 62.2, 50.6, 14.3.

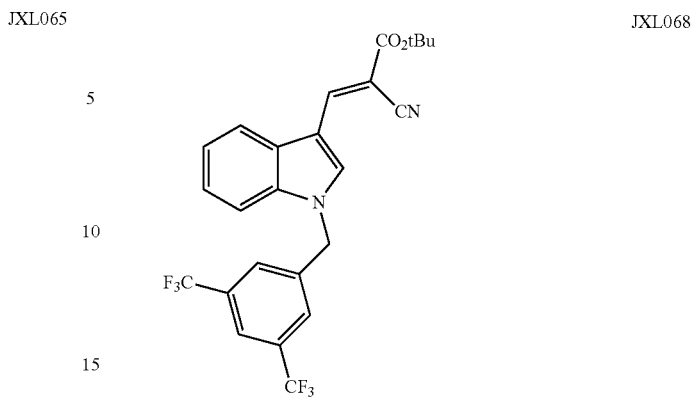

Tert-Butyl (E)-3-(1-(3,5-bis(trifluoromethyl)benzyl)-1H-indol-3-yl)-2-cyanoacrylate (JXL068)

¹H NMR (500 MHz, CDCl₃) δ 8.57 (s, 1H), 8.54 (s, 1H), 7.86 (d, J=7.6 Hz, 1H), 7.84 (s, 1H), 7.56 (s, 2H), 7.33 (m, 2H), 7.22 (d, J=7.4 Hz, 1H), 5.55 (s, 2H), 1.59 (s, 9H).

¹³C NMR (126 MHz, CDCl₃) δ 162.4, 144.7, 138.2, 135.9, 133.0, 132.7 (q, $J_{c-f}$=32.8 Hz), 128.6, 126.7, 124.5, 123.0, 122.9 (q, $J_{c-f}$=277.2 Hz), 122.6, 119.0, 118.2, 111.1, 110.4, 97.7, 82.9, 50.4, 28.1.

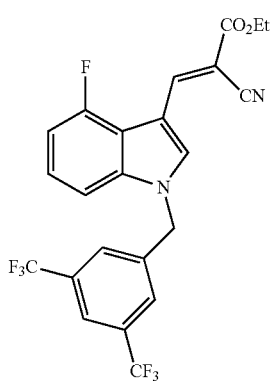

Ethyl (E)-3-(1-(3,5-bis(trifluoromethyl)benzyl)-4-fluoro-1H-indol-3-yl)-2-cyanoacrylate (JXL066)

¹H NMR (500 MHz, DMSO-d₆) δ 8.86 (s, 1H), 8.61 (s, 1H), 7.86 (s, 1H), 7.56 (s, 2H), 7.23 (m, 1H), 7.01 (m, 2H), 5.54 (s, 2H), 4.37 (q, J=7.1 Hz, 2H), 1.39 (t, J=7.1 Hz, 3H).

¹³C NMR (126 MHz, DMSO-d₆) δ 163.1, 157.4 (d, J=243.9 Hz), 147.4, 138.2 (d, J=10.1 Hz), 137.8, 133.2, 132.7 (q, $J_{c-f}$=33.9 Hz), 126.7, 125.3, 122.8 (q, $J_{c-f}$=273.4 Hz), 122.7, 117.9, 116.9 (d, $J_{c-f}$=17.6 Hz), 110.0, 109.0 (d, $J_{c-f}$=19.5 Hz), 106.6, 97.1, 62.2, 50.7, 14.3.

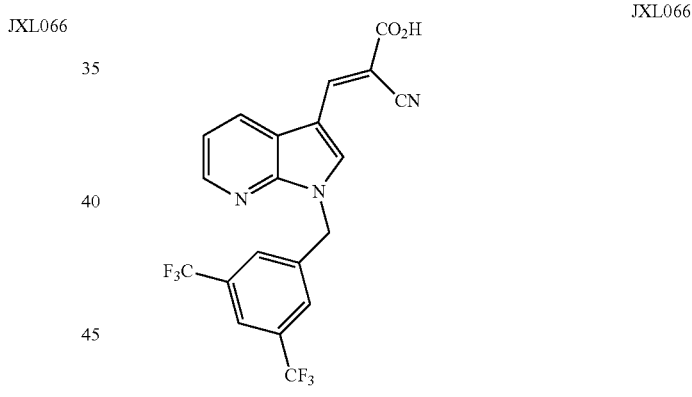

(E)-3-(1-(3,5-Bis(trifluoromethyl)benzyl)-1H-pyrrolo[2,3-b]pyridin-3-yl)-2-cyanoacrylic Acid (JXL069)

¹H NMR (500 MHz, DMSO-d₆) δ 8.85 (s, 1H), 8.47 (m, 3H), 8.09 (s, 2H), 8.04 (s, 1H), 7.35 (dd, J=7.1, 4.6 Hz, 1H), 5.84 (s, 2H).

¹³C NMR (126 MHz, DMSO-d₆) δ 185.9, 164.6, 147.8, 146.1, 145.5, 141.0, 135.2, 131.0 (q, $J_{c-f}$=32.8 Hz), 129.4, 126.9, 123.6 (q, $J_{c-f}$=274.0 Hz), 122.3, 120.1, 119.1, 118.2, 97.1, 47.8.

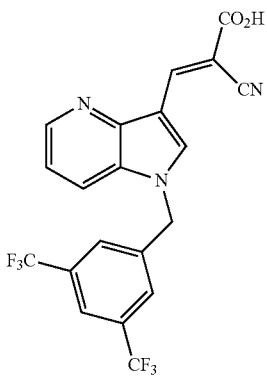

(E)-3-(1-(3,5-Bis(trifluoromethyl)benzyl)-1H-pyrrolo[3,2-b]pyridin-3-yl)-2-cyanoacrylic Acid (JXL072)

$^1$H NMR (500 MHz, DMSO-d$_6$) δ 8.94 (s, 1H), 8.68 (s, 1H), 8.54 (s, 1H), 8.11 (m, 4H), 7.35 (s, 1H), 5.87 (s, 2H).

$^{13}$C NMR (126 MHz, DMSO-d$_6$) δ 164.5, 145.9, 144.2, 140.1, 135.9, 131.1 (q, J$_{c-f}$=32.8 Hz), 129.6, 129.2, 124.7, 123.6 (q, J$_{c-f}$=274.0 Hz), 122.5, 120.0, 119.5, 117.9, 110.1, 97.2, 49.8.

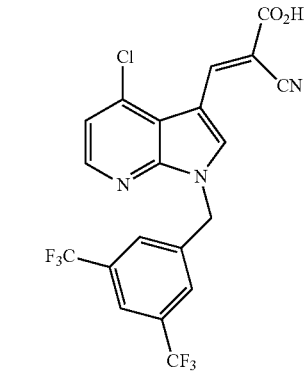

(E)-3-(1-(3,5-Bis(trifluoromethyl)benzyl)-4-chloro-1H-pyrrolo[2,3-b]pyridin-3-yl)-2-cyanoacrylic Acid (JXL076)

$^1$H NMR (500 MHz, DMSO-d$_6$) δ 9.00 (s, 1H), 8.98 (s, 1H), 8.36 (s, 1H), 8.12 (s, 2H), 8.04 (br. s, 1H), 7.47 (br. s, 1H), 5.85 (s, 2H).

$^{13}$C NMR (126 MHz, DMSO-d$_6$) δ 164.4, 148.7, 145.8, 145.7, 140.2, 136.1, 135.3, 131.0 (q, J$_{c-f}$=32.8 Hz), 129.5, 123.6 (q, J$_{c-f}$=274.0 Hz), 122.4, 120.4, 117.7, 116.8, 108.2, 98.1, 48.2.

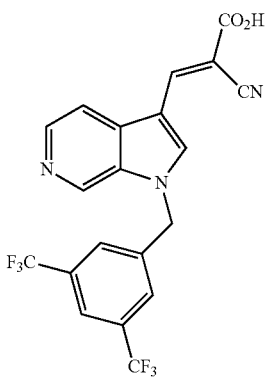

(E)-3-(1-(3,5-Bis(trifluoromethyl)benzyl)-1H-pyrrolo[2,3-c]pyridin-3-yl)-2-cyanoacrylic Acid (JXL073)

$^1$H NMR (500 MHz, DMSO-d$_6$) δ 9.14 (s, 1H), 8.96 (s, 1H), 8.55 (s, 1H), 8.40 (d, J=5.1 Hz, 1H), 8.19 (s, 2H), 8.11 (app. s, 2H), 5.95 (s, 2H).

$^{13}$C NMR (126 MHz, DMSO-d$_6$) δ 164.5, 145.5, 140.7, 139.9, 138.1, 134.5, 133.6, 131.1 (q, J$_{c-f}$=32.8 Hz), 129.4, 127.2, 123.6 (q, J$_{c-f}$=274.0 Hz), 122.7, 118.0, 114.6, 109.7, 97.9, 49.8.

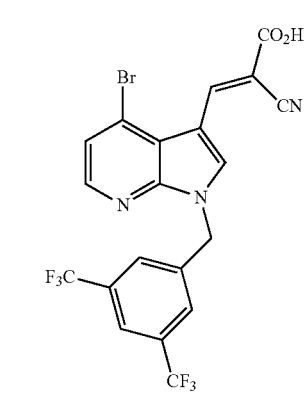

(E)-3-(1-(3,5-Bis(trifluoromethyl)benzyl)-4-bromo-1H-pyrrolo[2,3-b]pyridin-3-yl)-2-cyanoacrylic Acid (JXL077)

$^1$H NMR (500 MHz, DMSO-d$_6$) δ 9.17 (s, 1H), 9.02 (s, 1H), 8.27 (d, J=5.0 Hz, 1H), 8.12 (s, 2H), 8.05 (s, 1H), 7.63 (d, J=5.0 Hz, 1H), 5.85 (s, 2H).

$^{13}$C NMR (126 MHz, DMSO-d$_6$) δ 164.4, 148.2, 145.5, 145.3, 140.2, 135.4, 131.0 (q, J$_{c-f}$=32.8 Hz), 129.6, 124.9, 123.7, 123.6 (q, J$_{c-f}$=274.0 Hz), 122.4, 118.4, 117.7, 108.6, 97.9, 48.2.

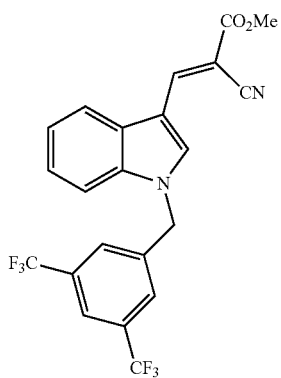

Methyl (E)-3-(1-(3,5-bis(trifluoromethyl)benzyl)-1H-indol-3-yl)-2-cyanoacrylate (JXL078)

$^1$H NMR (500 MHz, CDCl$_3$) δ 8.62 (s, 1H), 8.61 (s, 1H), 7.89 (d, J=7.7 Hz, 1H), 7.84 (s, 1H), 7.57 (s, 2H), 7.35 (m, 2H), 7.24 (m, 1H), 5.55 (s, 2H), 3.92 (s, 3H).

$^{13}$C NMR (126 MHz, CDCl$_3$) δ 164.5, 145.8, 138.1, 136.0, 133.5, 132.7 (q, J$_{c-f}$=32.8 Hz), 128.6, 126.8, 124.7, 123.9, 123.6 (q, J$_{c-f}$=274.0 Hz), 123.2, 119.1, 118.0, 111.2, 110.5, 95.4, 53.0, 50.5.

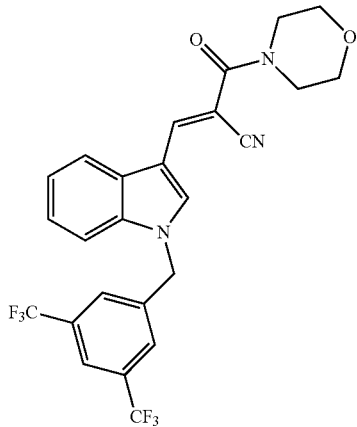

(E)-3-(1-(3,5-Bis(trifluoromethyl)benzyl)-1H-indol-3-yl)-2-(morpholine-4-carbonyl)acrylonitrile (JXL081)

$^1$H NMR (500 MHz, CDCl$_3$) δ 8.48 (s, 1H), 8.34 (s, 1H), 7.84 (s, 2H), 7.56 (app. s, 2H), 7.32 (m, 2H), 7.22 (m, 1H), 5.54 (s, 2H), 3.77 (br. s, 8H).

$^{13}$C NMR (126 MHz, CDCl$_3$) δ 164.0, 145.2, 138.4, 135.8, 132.7 (q, J$_{c-f}$=34.0 Hz), 131.8, 128.4, 126.8, 125.0, 124.5, 123.1 (q, J$_{c-f}$=273.3 Hz), 122.8, 121.8, 119.0, 118.6, 111.4, 110.3, 98.1, 66.7, 50.3, 50.0.

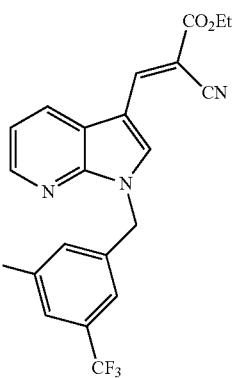

Ethyl (E)-3-(1-(3,5-bis(trifluoromethyl)benzyl)-1H-pyrrolo[2,3-b]pyridin-3-yl)-2-cyanoacrylate (JXL082)

$^1$H NMR (500 MHz, CDCl$_3$) δ 8.64 (s, 1H), 8.51 (s, 1H), 8.48 (dd, J=4.6, 1.2 Hz, 1H), 8.21 (dd, J=7.9, 1.2 Hz, 1H), 7.83 (s, 1H), 7.77 (s, 2H), 7.34 (dd, J=7.9, 4.6 Hz, 1H), 5.69 (s, 2H), 4.38 (q, J=7.1 Hz, 2H), 1.40 (t, J=7.1 Hz, 3H).

$^{13}$C NMR (126 MHz, CDCl$_3$) δ 163.3, 147.6, 145.7, 145.0, 138.5, 132.7, 132.3 (q, J$_{c-f}$=33.6 Hz), 127.9, 127.7, 123.1 (q, J$_{c-f}$=273.3 Hz), 122.5, 120.3, 119.0, 117.6, 109.4, 97.0, 62.3, 48.3, 14.3.

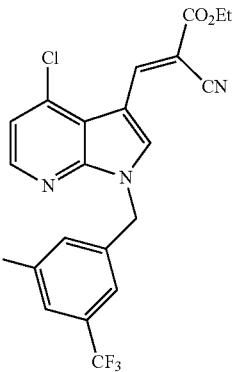

Ethyl (E)-3-(1-(3,5-bis(trifluoromethyl)benzyl)-4-chloro-1H-pyrrolo[2,3-b]pyridin-3-yl)-2-cyanoacrylate (JXL087)

$^1$H NMR (500 MHz, CDCl$_3$) δ 9.22 (s, 1H), 8.77 (s, 1H), 8.32 (d, J=5.2 Hz, 1H), 7.83 (s, 1H), 7.77 (s, 2H), 7.31 (d, J=5.2 Hz, 1H), 5.67 (s, 2H), 4.37 (q, J=7.1 Hz, 2H), 1.39 (t, J=7.1 Hz, 3H).

$^{13}$C NMR (126 MHz, CDCl$_3$) δ 163.0, 148.5, 146.2, 145.4, 138.1, 137.4, 133.1, 132.4 (q, J$_{c-f}$=33.7 Hz), 128.0, 122.9 (q, J$_{c-f}$=273.4 Hz), 122.6, 121.8, 117.6, 117.2, 109.7, 97.8, 62.4, 48.6, 14.3.

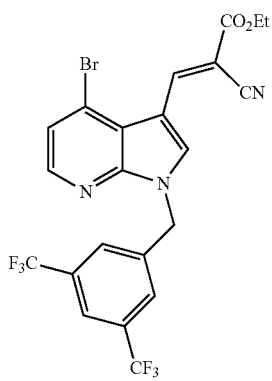

Ethyl (E)-3-(1-(3,5-bis(trifluoromethyl)benzyl)-4-bromo-1H-pyrrolo[2,3-b]pyridin-3-yl)-2-cyanoacrylate (JXL088)

$^1$H NMR (500 MHz, CDCl$_3$) δ 9.40 (s, 1H), 8.78 (s, 1H), 8.22 (d, J=5.1 Hz, 1H), 7.83 (s, 1H), 7.77 (s, 2H), 7.49 (d, J=5.1 Hz, 1H), 5.67 (s, 2H), 4.37 (q, J=7.1 Hz, 2H), 1.39 (t, J=7.1 Hz, 3H).

$^{13}$C NMR (126 MHz, CDCl$_3$) δ 163.1, 148.1, 145.7, 145.1, 138.1, 137.4, 133.4, 132.4 (q, J$_{c-f}$=33.7 Hz), 123.7, 122.9 (q, J$_{c-f}$=273.4 Hz), 122.6, 119.7, 117.6, 110.0, 101.4, 97.4, 62.4, 48.6, 14.3.

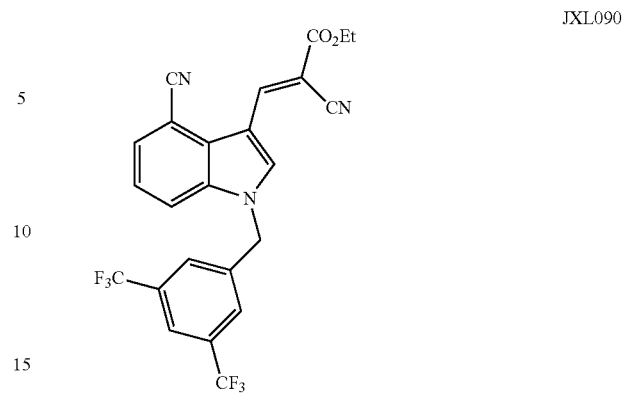

Ethyl (E)-3-(1-(3,5-bis(trifluoromethyl)benzyl)-4-cyano-1H-indol-3-yl)-2-cyanoacrylate (JXL090)

$^1$H NMR (500 MHz, CDCl$_3$) δ 9.29 (s, 1H), 8.78 (s, 1H), 7.87 (s, 1H), 7.68 (dd, J=7.4, 0.8 Hz, 1H), 7.56 (s, 2H), 7.49 (dd, J=8.4, 0.8 Hz, 1H), 7.38 (dd, J=8.4, 7.4 Hz, 1H), 5.62 (s, 2H), 4.38 (q, J=7.1 Hz, 2H), 1.40 (t, J=7.1 Hz, 3H).

$^{13}$C NMR (126 MHz, CDCl$_3$) δ 162.6, 144.3, 137.3, 136.2, 135.1, 132.9 (q, J$_{c-f}$=33.7 Hz), 129.4, 127.3, 126.7, 124.1, 123.0, 122.8 (q, J$_{c-f}$=273.4 Hz), 117.9, 117.5, 115.4, 110.7, 103.5, 98.6, 62.4, 50.6, 14.3.

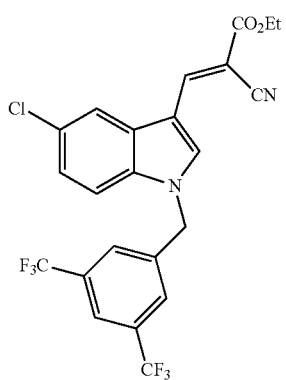

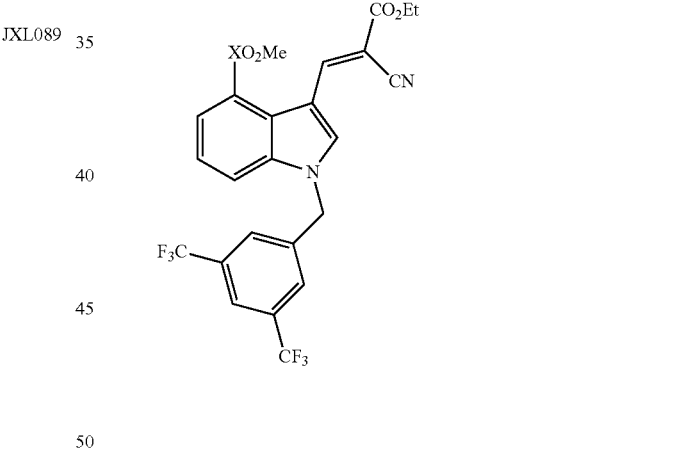

Methyl (E)-1-(3,5-bis(trifluoromethyl)benzyl)-3-(2-cyano-3-ethoxy-3-oxoprop-1-en-1-yl)-1H-indole-4-carboxylate (JXL091)

$^1$H NMR (500 MHz, CDCl$_3$) δ 9.36 (s, 1H), 8.71 (s, 1H), 7.93 (dd, 1H, J=7.4, 1.1 Hz, 1H), 7.85 (s, 1H), 7.55 (s, 2H), 7.40 (dd, J=8.3, 1.1 Hz, 1H), 7.34 (dd, J=8.3, 7.4 Hz, 1H), 5.58 (s, 2H), 4.37 (q, J=7.1 Hz, 2H), 4.04 (s, 3H), 1.40 (t, J=7.1 Hz, 3H).

$^{13}$C NMR (126.1 MHz, CDCl$_3$) δ 167.8, 163.5, 150.1, 137.8, 137.2, 134.9, 132.8 (q, J$_{c-f}$=33.7 Hz), 126.7, 125.8, 125.1, 123.6, 122.8 (q, J$_{c-f}$=273.4 Hz), 122.7, 121.7, 118.0, 114.6, 111.3, 96.4, 62.1, 52.6, 50.5, 14.3.

Ethyl (E)-3-(1-(3,5-bis(trifluoromethyl)benzyl)-5-chloro-1H-indol-3-yl)-2-cyanoacrylate (JXL089)

$^1$H NMR (500 MHz, CDCl$_3$) δ 8.60 (s, 1H), 8.50 (s, 1H), 7.85 (s, 1H), 7.83 (s, 1H), 7.55 (s, 2H), 7.28 (dd, J=8.7, 1.7 Hz, 1H), 7.14 (d, J=8.7 Hz, 1H), 5.54 (s, 2H), 4.38 (q, J=7.1 Hz, 2H), 1.40 (t, J=7.1 Hz, 3H).

$^{13}$C NMR (126 MHz, CDCl$_3$) δ 163.2, 144.8, 137.7, 134.3, 134.1, 132.8 (q, J$_{c-f}$=33.7 Hz), 129.7, 129.3, 126.7, 125.1, 122.8 (q, J$_{c-f}$=273.4 Hz), 122.7, 118.9, 117.7, 111.6, 110.6, 96.9, 62.3, 50.6, 14.3.

Experimental Detail for the Synthesis of JXL024

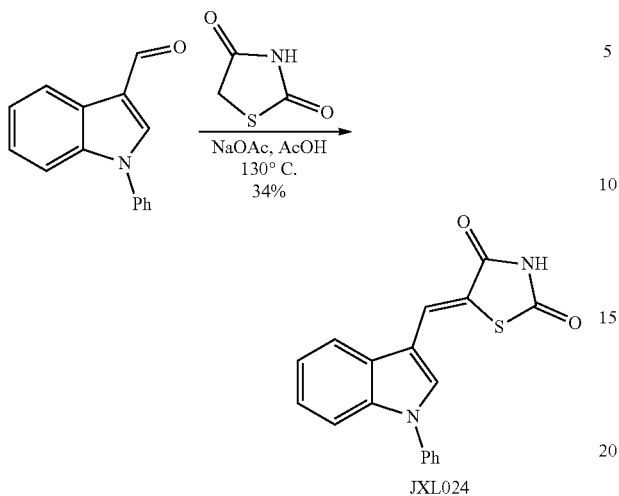

To the solution of 1-phenyl-1H-indole-3-carbaldehyde (0.4 mmol, 90 mg) in AcOH (3 mL) were added thiazolidine-2,4-dione (1 equiv, 0.4 mmol, 46.8 mg) and NaOAc (3 equiv, 98 mg). The reaction mixture was stirred at reflux for 24 hours. After it was cooled to 21° C., the reaction mixture was filtered by vacuum filtration and washed by AcOH (3 mL×3) and water (5 mL×3). After drying by vacuum, the desired product was produced. yield: 34%, 44 mg.

(Z)-5-((1-Phenyl-1H-indol-3-yl)methylene)thiazolidine-2,4-dione (JXL024)

$^1$H NMR (500 MHz DMSO-$d_6$) δ 7.98 (m, 2H), 7.79 (s, 1H), 7.66 (app. d, J=7.7 Hz, 2H), 7.62 (app. t, J=7.7 Hz, 2H), 7.54 (d, J=8.0 Hz, 1H), 7.49 (t, J=7.1 Hz, 1H), 7.30 (m, 2H).
$^{13}$C NMR (126 MHz, DMSO-$d_6$) δ 172.5, 169.5, 138.4, 136.2, 130.5, 129.9, 128.3, 128.2, 125.0, 124.6, 122.4, 121.5, 121.4, 119.6, 113.0, 111.5.

The following compounds were synthesized by a route similar to that described for JXL024: JXL067, JXL070, JXL072, JXL074, JXL075.

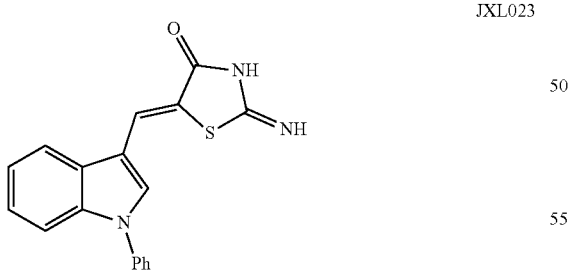

(Z)-2-Imino-5-((1-phenyl-1H-indol-3-yl)methylene)thiazolidin-4-one (JXL023)

$^1$H NMR (500 MHz, DMSO-$d_6$) δ 11.94 (br. s, 1H), 9.33 (br. s, 1H), 8.97 (s, 1H), 7.64 (m, 10H).
$^{13}$C NMR (126 MHz, DMSO-$d_6$) δ 180.9, 174.8, 172.5, 138.6, 136.2, 130.5, 129.3, 128.1, 126.3, 124.8, 124.5, 122.2, 120.3, 119.7, 113.5, 111.5.

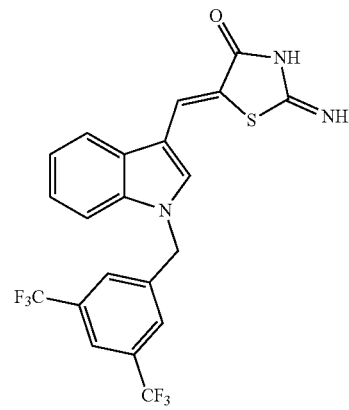

(Z)-5-((1-(3,5-Bis(trifluoromethyl)benzyl)-1H-indol-3-yl)methylene)-2-iminothiazolidin-4-one (JXL067)

$^1$H NMR (500 MHz, DMSO-$d_6$) δ 9.21 (s, 1H), 9.01 (s, 1H), 8.03 (s, 1H), 7.94 (br. s, 3H), 7.86 (d, J=7.7 Hz, 1H), 7.81 (s, 11H), 7.58 (d, J=7.9 Hz, 11H), 7.24 (m, 11H), 7.19 (m, 1H), 5.76 (s, 2H).
$^{13}$C NMR (126 MHz, DMSO-$d_6$) δ 180.0, 174.9, 141.4, 136.5, 131.0 (q, $J_{c-f}$=32.8 Hz), 130.4, 128.5, 127.9, 125.1, 123.8, 123.6 (q, $J_{c-f}$=274.0 Hz), 122.1, 121.7, 120.8, 119.3, 111.8, 111.3, 48.9.

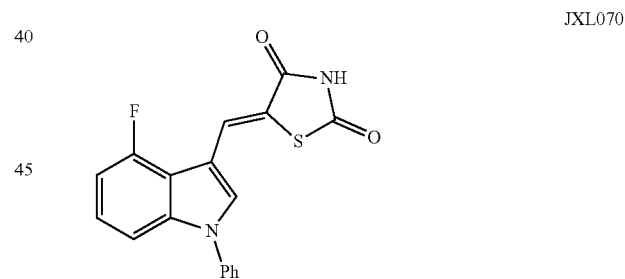

(Z)-5-((4-Fluoro-1-phenyl-1H-indol-3-yl)methylene)thiazolidine-2,4-dione (JXL070)

$^1$H NMR (500 MHz, DMSO-$d_6$) δ 12.45 (br. s, 1H), 8.11 (s, 1H), 7.83 (s, 1H), 7.65 (m, 4H), 7.52 (s, 1H), 7.32 (m, 2H), 7.12 (m, 1H).
$^{13}$C NMR (126 MHz, DMSO-$d_6$) δ 168.0, 167.7, 156.9 (d, $J_{c-f}$=245.7 Hz), 138.7 (d, $J_{c-f}$=10.1 Hz), 137.9, 130.8, 130.5, 128.8, 125.5, 125.4, 124.3, 120.0, 116.2 (d, $J_{c-f}$=18.9 Hz), 110.7, 108.5, 108.1 (d, $J_{c-f}$=18.9 Hz).

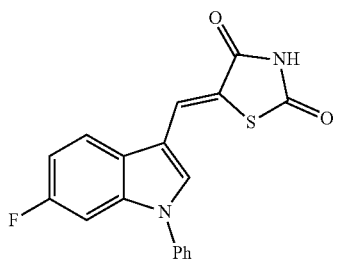

(Z)-5-((6-Fluoro-1-phenyl-1H-indol-3-yl)methylene)thiazolidine-2,4-dione (JXL071)

$^1$H NMR (500 MHz, DMSO-$d_6$) δ 12.42 (s, 1H), 8.06 (app. s, 2H), 7.85 (s, 1H), 7.67 (m, 2H), 7.62 (m, 2H), 7.50 (m, 1H), 7.31 (d, J=9.6 Hz, 1H), 7.16 (t, J=8.5 Hz, 1H).

$^{13}$C NMR (126 MHz, DMSO-$d_6$) δ 168.0, 167.7, 160.6 (d, $J_{c-f}$=245.7 Hz), 138.0, 136.3 (d, $J_{c-f}$=12.6 Hz), 131.0, 130.6, 128.5, 125.0, 124.8, 123.5, 121.3 (d, $J_{c-f}$=10.0 Hz), 120.0, 112.6, 111.1 (d, $J_{c-f}$=18.9 Hz), 98.2 (d, $J_{c-f}$=18.9 Hz).

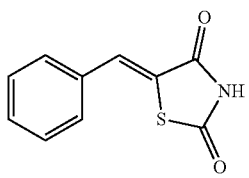

(Z)-5-Benzylidenethiazolidine-2,4-dione (JXL074)

$^1$H NMR (500 MHz, DMSO-$d_6$) δ 12.60 (br. s, 1H), 7.77 (s, 1H), 7.58 (app. d, J=7.3 Hz, 2H), 7.51 (app. t, J=7.4 Hz, 2H), 7.46 (m, 1H).

$^{13}$C NMR (126 MHz, DMSO-$d_6$) δ 168.4, 167.8, 133.5, 132.3, 130.9, 130.5, 129.8, 124.0.

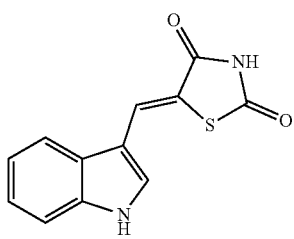

(Z)-5-((1H-Indol-3-yl)methylene)thiazolidine-2,4-dione (JXL075)

$^1$H NMR (500 MHz, DMSO-$d_6$) δ 12.28 (s, 1H), 12.11 (s, 1H), 8.03 (s, 1H), 7.87 (d, J=7.3 Hz, 1H), 7.72 (s, 1H), 7.48 (d, J=7.6 Hz, 1H), 7.23 (m, 1H), 7.18 (m, 1H).

$^{13}$C NMR (126 MHz, DMSO-$d_6$) δ 168.2, 167.8, 136.7, 129.1, 127.3, 125.0, 123.5, 121.5, 118.8, 116.7, 112.9, 110.9.

Experimental Detail for the Synthesis of JXL022

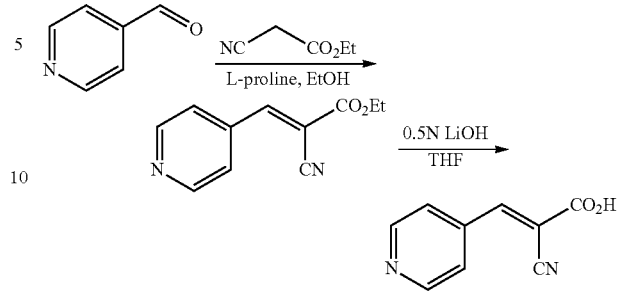

To the solution of 4-pyridinecarboxaldehyde (1 mmol, 107 mg) in ethanol (1 mL) were added ethyl 2-cyanoacetate (1.3 equiv, 1.3 mmol, 140 μL) and L-proline (40 mol %, 0.4 mmol, 58 mg). The reaction was stirred at 21° C. for 12 h and yellow solid precipitated gradually. After completion of the reaction, ice-cold water (2 mL) was added into the reaction vial. The solid was separated by Buchner funnel filtration and washed with water (2 mL×3) and dried to afford the desired product, ethyl (E)-2-cyano-3-(pyridin-4-yl)acrylate, which was used for the next step without further purification.

To the solution of (T)-2-cyano-3-(pyridin-4-yl)acrylate (0.21 mmol, 42.4 mg) in THF (2 mL) was added 0.5N LiOH solution (3 equiv, 0.4 mmol, 0.8 mL). The reaction mixture was stirred at 21° C. for 1 h. After reaction completion shown by TLC, THF was evaporated. Concentrated HCl was added dropwise to acidify the reaction mixture until pH was lower than 1, meanwhile yellow solid precipitated. Ice-cold water (5 mL) was added to the reaction mixture and the solid was separated by Buchner funnel filtration and washed with water (5 mL×3). After dried by vacuum, the solid was washed by 2 mL of solvent mixture (hexanes/EtOAc=5:1) 5 to 10 times and monitored by TLC until non-polar impurities disappear. Finally, the purity of the product was checked by NMR. yield: 64%, 23.4 mg.

Ethyl (E)-2-cyano-3-(pyridin-4-yl)acrylate (JXL022)

$^1$H NMR (500 MHz, CDCl$_3$) δ 8.81 (d, J=5.2 Hz, 2H), 8.18 (s, 1H), 7.74 (d, J=5.2 Hz, 2H), 4.41 (q, J=7.1 Hz, 2H), 1.41 (t, J=7.1 Hz, 3H).

$^{13}$C NMR (126 MHz, CDCl$_3$) δ 161.2, 152.0, 151.0, 137.9, 123.2, 114.2, 108.2, 63.2, 14.0.

The following compounds were synthesized by a route similar to that described for JXL022: JXL030, JXL031, JXL032, JXL033, JXL034, JXL042, JXL43, JXL044, JXL045, JXL046, JXL047, JXL048, JXL049.

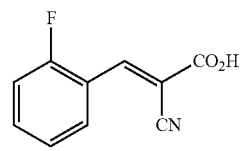

(E)-2-Cyano-3-(2-fluorophenyl)acrylic acid (JXL030)

$^1$H NMR (500 MHz, DMSO-$d_6$) δ 8.49 (s, 1H), 8.31 (t, J=7.4 Hz, 1H), 7.63 (m, 1H), 7.36 (t, J=7.4 Hz, 1H), 7.29 (m, 1H).
$^{13}$C NMR (126 MHz, DMSO-$d_6$) δ 162.9, 161.5 (d, $J_{c-f}$=256.2 Hz), 145.4 (d, $J_{c-f}$=7.8 Hz), 135.0 (d, $J_{c-f}$=9.2 Hz), 128.7, 124.7, 119.8 (d, $J_{c-f}$=10.9 Hz), 115.8 (d, $J_{c-f}$=21.9 Hz), 114.9, 105.9.

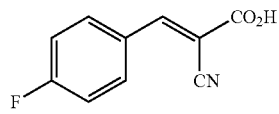

JXL032

(E)-2-Cyano-3-(4-fluorophenyl)acrylic acid (JXL032)

$^1$H NMR (500 MHz, DMSO-$d_6$) δ 8.30 (s, 1H), 8.10 (m, 2H), 7.29 (m, 2H).
$^{13}$C NMR (126 MHz, DMSO-$d_6$) δ 165.2 (d, $J_{c-f}$=255.2 Hz), 163.5, 153.1, 133.3 (d, $J_{c-f}$=9.3 Hz), 128.3, 116.0 (d, $J_{c-f}$=22.4 Hz), 115.3, 103.2.

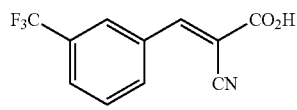

JXL033

(E)-2-cyano-3-(3-(trifluoromethyl)phenyl)acrylic acid (JXL033)

$^1$H NMR (500 MHz, CD$_3$OD) δ 8.24 (s, 1H), 8.17 (m, 2H), 7.80 (d, J=7.8 Hz, 1H), 7.70 (app. t, J=7.8 Hz, 1H).

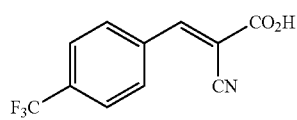

JXL034

(E)-2-Cyano-3-(4-(trifluoromethyl)phenyl)acrylic acid (JXL034)

$^1$H NMR (500 MHz, DMSO-$d_6$) δ 8.39 (s, 1H), 8.17 (d, J=7.7 Hz, 2H), 7.84 (d, J=7.7 Hz, 2H).
$^{13}$C NMR (126 MHz, DMSO-$d_6$) δ 162.8, 152.6, 135.4, 133.1 (q, $J_{c-f}$=32.9 Hz), 131.0, 125.7, 123.7 (q, $J_{c-f}$=272.2 Hz), 114.8, 106.7.

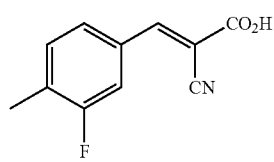

JXL042

(E)-2-Cyano-3-(3-fluoro-4-methylphenyl)acrylic acid (JXL042)

$^1$H NMR (500 MHz, DMSO-$d_6$) δ 8.28 (s, 1H), 7.78 (m, 2H), 7.49 (t, J=8.0 Hz, 1H), 2.30 (s, 3H).
$^{13}$C NMR (126 MHz, DMSO-$d_6$) δ 163.6, 160.9 (d, $J_{c-f}$=244.6 Hz), 153.5, 133.0, 131.6 (d, $J_{c-f}$=7.5 Hz), 130.8 (d, $J_{c-f}$=17.6 Hz), 127.2, 117.9 (d, $J_{c-f}$=23.9 Hz), 116.4, 104.5, 15.0.

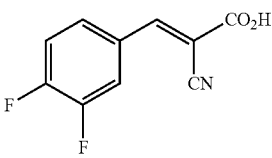

JXL043

(E)-2-Cyano-3-(3,4-difluorophenyl)acrylic Acid (JXL043)

$^1$H NMR (500 MHz, DMSO-$d_6$) δ 8.32 (s, 1H), 8.09 (d, J=8.0 Hz, 1H), 7.94 (br. s, 1H), 7.67 (d, J=8.8 Hz, 1H).
$^{13}$C NMR (126 MHz, DMSO-$d_6$) δ 163.3, 152.3, 152.2 (dd, $J_{c-f}$=255.4, 12.6 Hz), 149.9 (dd, $J_{c-f}$=248.2, 12.6 Hz), 129.8, 128.8, 120.1 (d, $J_{c-f}$=17.6 Hz), 119.1 (d, $J_{c-f}$=17.6 Hz), 116.3, 105.8.

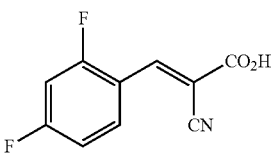

JXL044

(E)-2-Cyano-3-(2,4-difluorophenyl)acrylic Acid (JXL044)

$^1$H NMR (500 MHz, DMSO-$d_6$) δ 14.2 (br. s, 1H), 8.27 (s, 1H), 8.24 (m, 1H), 7.52 (m, 1H), 7.35 (dt, J=8.6, 2.2 Hz, 1H).
$^{13}$C NMR (126 MHz, DMSO-$d_6$) δ 165.5 (dd, $J_{c-f}$=255.8, 12.6 Hz), 163.1, 161.9 (dd, $J_{c-f}$=270.5, 12.6 Hz), 145.1, 131.1, 117.0, 115.9, 113.5 (d, $J_{c-f}$=22.7 Hz), 106.8, 105.6 (t, $J_{c-f}$=26.5 Hz).

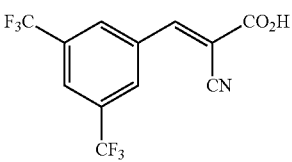

JXL045

(E)-3-(3,5-bis(trifluoromethyl)phenyl)-2-cyano-acrylic Acid (JXL045)

$^1$H NMR (500 MHz, CD$_3$OD) δ 8.59 (s, 2H), 8.48 (s, 1H), 8.19 (s, 1H).

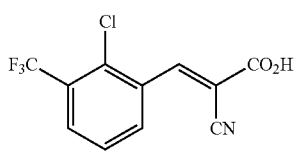

(E)-3-(2-Chloro-3-(trifluoromethyl)phenyl)-2-cyano-acrylic Acid (JXL046)

$^1$H NMR (500 MHz, DMSO-d$_6$) δ 8.50 (s, 1H), 8.23 (d, J=7.7 Hz, 1H), 8.05 (d, J=7.4 Hz, 1H), 7.75 (app. t, J=7.9 Hz, 1H).
$^{13}$C NMR (126 MHz, DMSO-d$_6$) δ 162.6, 150.5, 134.4, 133.5, 132.1, 131.2, 128.9, 128.3 (q, J$_{c-f}$=30.2 Hz), 123.1 (q, J$_{c-f}$=274.1 Hz) 115.1, 111.1.

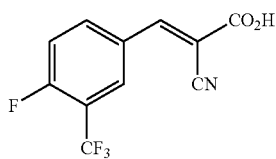

(E)-2-Cyano-3-(4-fluoro-3-(trifluoromethyl)phenyl)acrylic Acid (JXL047)

$^1$H NMR (500 MHz, DMSO-d$_6$) δ 8.46 (dd, J=7.1, 1.8 Hz, 1H), 8.44 (s, 1H), 8.40 (m, 1H), 7.75 (m, 1H).
$^{13}$C NMR (126 MHz, DMSO-d$_6$) δ 163.3, 161.1 (d, J$_{c-f}$=262.1 Hz), 152.2, 137.6 (d, J$_{c-f}$=10.1 Hz), 130.5, 129.3, 122.6 (q, J$_{c-f}$=272.8 Hz), 118.9 (d, J$_{c-f}$=21.2 Hz), 118.2 (qd, J$_{c-f}$=320.9, 12.6 Hz), 116.2, 106.3.

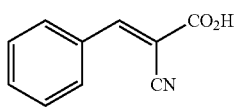

(E)-2-Cyano-3-phenylacrylic Acid (JXL048)

$^1$H NMR (500 MHz, DMSO-d$_6$) δ 8.33 (s, 1H), 8.02 (m, 2H), 7.59 (m, 3H).
$^{13}$C NMR (126 MHz, DMSO-d$_6$) δ 163.7, 154.9, 133.6, 132.0, 131.1, 129.8, 116.5, 104.3.

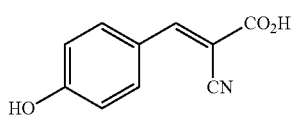

(E)-2-cyano-3-(4-hydroxyphenyl)acrylic Acid (JXL049)

$^1$H NMR (500 MHz, DMSO-d$_6$) δ 8.16 (s, 1H), 7.95 (d, J=8.8 Hz, 2H), 6.92 (d, J=8.8 Hz, 2H).

$^{13}$C NMR (126 MHz, DMSO-d$_6$) δ 164.2, 163.0, 153.7, 133.6, 122.8, 117.2, 116.3, 99.2.

Experimental Detail for the Synthesis of JXL079

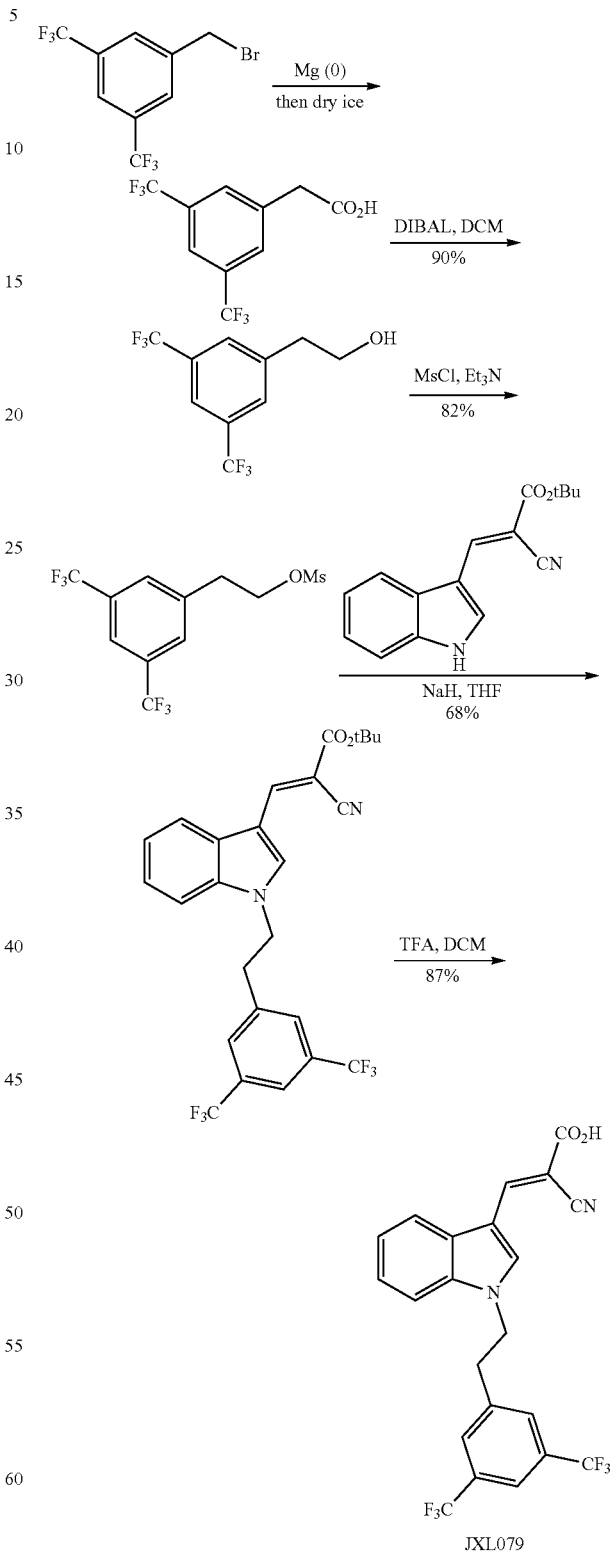

A flask containing Mg powder (10 mmol, 240 mg) and a stir bar was sealed and vacuumed and refilled with argon three times. Anhydrous diethyl ether (32 mL) and bis (trifluoromethyl)benzyl bromide (8 mmol, 1.46 mL) was added to the reaction flask. The reaction mixture was stirred and refluxed for 30 min and then ground dry ice powder (5 g) was added into the reaction flask. After 1 h, the reaction was complete as shown by TLC. The extra Mg powder was filtered off and the solvent was evaporated under vacuum. 1N HCl (20 mL) was added to the residue and the precipitate was filtered and dried to provide the desired carboxylic acid.

A flask containing a stir bar was sealed, vacuumed and refilled with argon three times. Anhydrous dichloromethane (20 mL) and DIBAL (1 M in hexanes, 6 mmol, 6 mL) were added to the flask. The crude carboxylic acid (2 mmol, 544 mg) dissolved in dry dichloromethane (10 mL) was added to the reaction flask at −78° C. After 2 h, the reaction was complete as shown by TLC and it was then quenched by adding sat. ammonium chloride (10 mL). The resulting mixture was extracted with dichloromethane (20 mL×3) and the organic phases were combined and evaporated on the rotavap. The residue was purified by flash column chromatography (hexanes:ethyl acetate=10:1) to afford the desired product 2-(3,5-bis(trifluoromethyl)phenyl)ethan-1-ol (yield: 90%, 464 mg).

To a solution of 2-(3,5-bis(trifluoromethyl)phenyl)ethan-1-ol (0.2 mmol, 51.6 mg) in dichloro-methane (2 mL) was added triethylamine (0.22 mmol, 31 μL) and mesyl chloride (MsCl, 0.2 mmol, 17 μL) at 0° C. After stirring for 1 h, the reaction was complete as shown by TLC. The solvent was removed by flowing air over the open flask. The residue was purified by flash column chromatography (hexanes:ethyl acetate=10:1) to afford the desired product 3,5-bis(trifluoromethyl)phenethyl methanesulfonate (yield: 82%, 55.1 mg).

A flask containing NaH (60%, 0.22 mmol, 8.8 mg) and a stir bar was sealed, vacuumed and refilled with argon three times. Anhydrous THF (3 mL) and a solution of tert-butyl (E)-2-cyano-3-(1H-indol-3-yl)acrylate (0.2 mmol, 53.6 mg) in THF (2 mL) were added into the reaction flask. The reaction mixture was stirred for 30 min and then 3,5-bis(trifluoromethyl)phenethyl methanesulfonate (0.164 mmol, 55.1 mg) in 2 mL THF was added. The reaction was stirred for 24 h and quenched by sat. NH$_4$Cl solution. The resulting mixture was extracted with dichloromethane (4 mL×3) and the organic phases were combined and evaporated on the rotavap. The residue was purified by flash column chromatography (hexanes:ethyl acetate=10:1) to afford the desired product tert-butyl (E)-3-(1-(3,5-bis(trifluoromethyl)phenethyl)-1H-indol-3-yl)-2-cyano-acrylate (yield: 68%, 69 mg).

To a solution of methyl tert-butyl (E)-3-(1-(3,5-bis(trifluoromethyl)phenethyl)-1H-indol-3-yl)-2-cyanoacrylate (0.1 mmol, 50.8 mg) in dichloromethane (2 mL) was added trifluoroacetic acid (3 equiv, 0.3 mmol, 34 μL). The reaction mixture was stirred at 21° C. for 30 min and a yellow solid precipitated. After the reaction was complete as shown by TLC, the reaction solvent was evaporated by flowing air over the open flask. The solid was washed by 2 mL of solvent mixture (hexanes/EtOAc=5:1) 5 to 10 times and monitored by TLC until all the non-polar impurities disappeared. Finally, the purity of the product was checked by NMR. yield: 87%, 39 mg.

(E)-3-(1-(3,5-Bis(trifluoromethyl)phenethyl)-1H-indol-3-yl)-2-cyanoacrylic Acid (JXL079)

$^1$H NMR (500 MHz, CD$_3$OD) δ 8.51 (s, 1H), 8.14 (s, 1H), 7.83 (d, J=7.3 Hz, 1H), 7.74 (s, 1H), 7.52 (m, 3H), 7.31 (m, 2H), 4.64 (t, J=6.4 Hz, 2H), 3.35 (t, J=6.3 Hz, 2H).

$^{13}$C NMR (126 MHz, CD$_3$OD) δ 165.3, 145.3, 141.1, 136.1, 133.6, 131.3 (q, J$_{c-f}$=32.8 Hz), 129.3, 128.3, 123.7, 123.3 (q, J$_{c-f}$=272.5 Hz), 122.3, 120.3, 118.1, 117.6, 110.6, 109.6, 94.1, 47.8, 35.0.

Experimental Detail for the Synthesis of JXL080

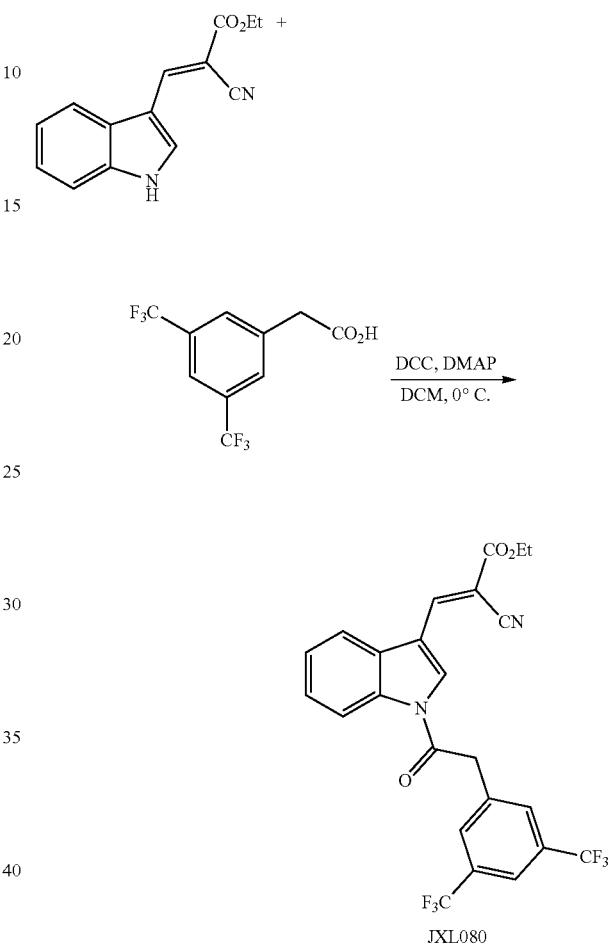

JXL080

To a solution of ethyl (E)-2-cyano-3-(1H-indol-3-yl)acrylate (0.5 mmol, 112 mg) in dichloromethane (5 mL) were added 2-(3,5-bis(trifluoromethyl)phenyl)acetic acid (0.55 mmol, 150 mg), DMAP (catalytic amount, 6 mg), and DCC (0.5 mmol, 103 mg) at 0° C. The mixture was allowed to reach 21° C. and stirred overnight. The white precipitate was filtered, and the resulting solution was concentrated in vacuum. The solid was purified by flash column chromatography (hexanes:ethyl acetate=10:1) to afford the desired product (yield: 78%, 192.6 mg).

Ethyl (E)-3-(1-(2-(3,5-bis(trifluoromethyl)phenyl)acetyl)-1H-indol-3-yl)-2-cyanoacrylate (JXL080)

$^1$H NMR (500 MHz, CDCl$_3$) δ 8.90 (s, 1H), 8.52 (s, 1H), 8.49 (d, J=8.1 Hz, 1H), 7.88 (s, 1H), 7.86 (s, 2H), 7.78 (d, J=7.5 Hz, 1H), 7.47 (m, 2H), 4.50 (s, 2H), 4.41 (q, J=7.1 Hz, 2H), 1.43 (t, J=7.1 Hz, 3H).

$^{13}$C NMR (126 MHz, CDCl$_3$) δ 168.0, 162.2, 144.2, 135.6, 134.4, 132.3 (q, J$_{c-f}$=33.6 Hz), 130.1, 129.8, 128.8, 127.8, 127.3, 125.5, 123.1 (q, J$_{c-f}$=273.3 Hz), 118.3, 117.1, 117.0, 115.9, 101.8, 62.8, 41.9, 14.3.

Experimental Detail for the Synthesis of JXL083

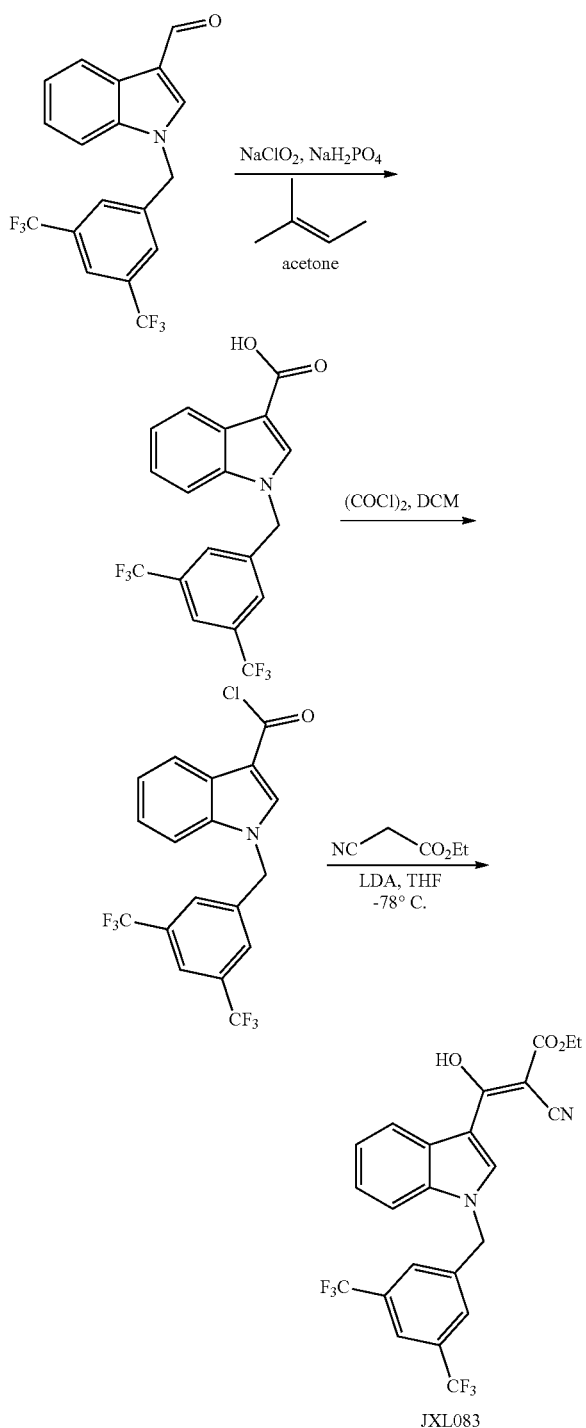

JXL083

To a solution of 1-(3,5-bis(trifluoromethyl)benzyl)-1H-indole-3-carbaldehyde (10 mmol, 3.71 g) in acetone (60 mL) was added 2-methyl-2-butene (9 mL), $NaH_2PO_4$ (3 equiv, 4.4 g) and $NaClO_2$ (6.6 mmol, 6 g) in 6 mL water. The reaction mixture was stirred at 21° C. for 24 h. After the reaction was complete as shown by TLC, the reaction solvent was evaporated on the rotavap. The crude material was dissolved in ethyl acetate (30 mL) and water (30 mL) and extracted with ethyl acetate (30 mL×3). The organic phase was combined, dried with sodium sulfate and evaporated on the rotavap. The solid was purified by flash column chromatography (hexanes:ethyl acetate=2:1) to afford the desired product 1-(3,5-bis(trifluoromethyl)benzyl)-1H-indole-3-carboxylic acid (yield: 89%, 3.44 g).

A 100 mL round bottom flask with a stir bar containing the carboxylic acid (5 mmol, 1935 mg) from the previous step was sealed, vacuumed and refilled with argon three times. To the flask was added 50 mL dichloromethane and oxalyl chloride (25 mmol, 2.1 mL) dropwise. The reaction mixture was stirred at 21° C. for 1.5 h. The reaction solvent was evaporated by vacuum and the resulting compound was used for the next step.

A 100 mL round bottom flask with a stir bar was sealed, vacuumed and refilled with argon three times. Diisopropylamine (5.5 mmol, 765 µL) and THF (10 mL) were added into the flask and it was cooled to −78° C. nBuLi (2.5 M in hexanes, 5 mmol, 2 mL) was added slowly to the flask. After the mixture had stirred for 30 min, a solution of ethyl 2-cyanoacetate (5 mmol, 590 µL) in THF (10 mL) was added slowly to the flask. After the mixture had stirred for 1 h, a solution of the acyl chloride (5 mmol from previous step) in THF (5 mL) was added slowly to the reaction mixture. After 1 h, the reaction was quenched by adding aqueous 1M HCl solution (10 mL) and extracted with ethyl acetate (10 mL×3). The organic phase was combined, dried with sodium sulfate and evaporated by rotavap. The solid was purified by flash column chromatography (hexanes:ethyl acetate=10:1) to afford the desired product Ethyl (Z)-3-(1-(3,5-bis(trifluoromethyl)benzyl)-1H-indol-3-yl)-2-cyano-3-hydroxyacrylate (JXL083) (yield: 80%, 1.93 g).

$^1$H NMR (500 MHz, $CDCl_3$) δ 14.61 (s, 1H), 8.67 (s, 1H), 8.31 (dd, J=7.0 1.3 Hz, 1H), 7.84 (s, 1H), 7.57 (s, 2H), 7.33 (m, 2H), 7.21 (d, J=7.4 Hz, 1H), 5.53 (s, 2H), 4.40 (q, J=7.1 Hz, 2H), 1.41 (t, J=7.1 Hz, 3H).

$^{13}$C NMR (126 MHz, $CDCl_3$) δ 179.1, 172.2, 138.1, 136.0, 135.7, 132.7 (q, $J_{c-f}$=33.6 Hz), 126.9, 124.5, 123.7, 123.6, 122.6, 122.9 (q, $J_{c-f}$=273.4 Hz), 121.8, 118.3, 110.1, 109.6, 73.1, 62.3, 50.4, 14.3.

Experimental Detail for the Synthesis of JXL084

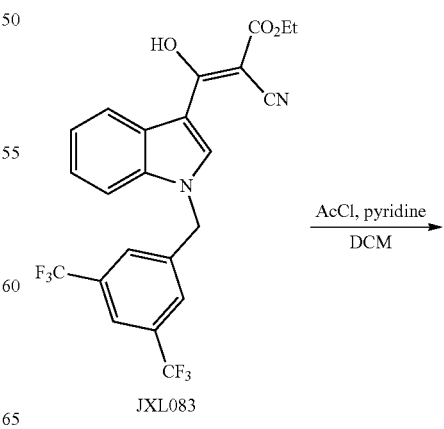

JXL083

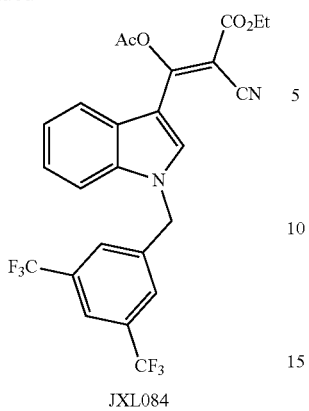

JXL084

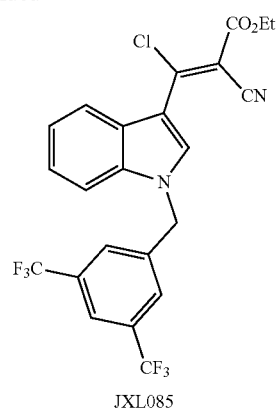

JXL085

To a solution of JXL083 (0.5 mmol, 240 mg) in dichloromethane (10 mL) was added pyridine (0.5 mmol, 40 μL) and acetyl chloride (1.0 mmol, 84 μL). The reaction mixture was stirred for 1 h and TLC indicated that the reaction was complete. The reaction solvent was evaporated by flowing air over the open flask. The residue was purified by flash column chromatography (hexanes:ethyl acetate=10:1) to afford the desired product Ethyl (Z)-3-acetoxy-3-(1-(3,5-bis(trifluoro-methyl)benzyl)-1H-indol-3-yl)-2-cyanoacrylate (JXL084) (yield: 86%, 225 mg).

$^1$H NMR (500 MHz, CDCl$_3$) δ 8.56 (s, 1H), 7.90 (m, 1H), 7.85 (s, 1H), 7.61 (s, 2H), 7.32 (m, 2H), 7.24 (m, 1H), 5.51 (s, 2H), 4.29 (q, J=7.1 Hz, 2H), 2.48 (s, 3H), 1.36 (t, J=7.1 Hz, 3H).

$^{13}$C NMR (126 MHz, CDCl$_3$) δ 166.9, 161.4, 137.7, 136.2, 135.5, 132.8 (q, J$_{c-f}$=33.9 Hz), 127.0, 126.7, 124.6, 123.6, 122.8 (q, J$_{c-f}$=273.4 Hz), 122.7, 121.8, 117.7, 110.7, 109.8, 89.3, 61.8, 50.5, 29.7, 21.3, 14.2.

Experimental Detail for the Synthesis of JXL085

To a solution of JXL083 (0.5 mmol, 240 mg) in dichloromethane (10 mL) was added triethylamine (1.0 mmol, 139.5 μL) and phosphoryl chloride (0.55 mmol, 520 μL). The reaction mixture was stirred for 1 h at reflux and TLC indicated that the reaction was complete. The reaction solvent was evaporated by flowing air over the open flask. The residue was purified by flash column chromatography (hexanes:ethyl acetate=10:1) to afford the desired product Ethyl (Z)-3-(1-(3,5-bis(trifluoromethyl)benzyl)-1H-indol-3-yl)-3-chloro-2-cyanoacrylate (JXL085) (yield: 84%, 210 mg).

$^1$H NMR (500 MHz, CDCl$_3$) δ 7.91 (s, 1H), 7.85 (s, 1H), 7.77 (m, 1H), 7.65 (s, 2H), 7.63 (s, 1H), 7.30 (m, 2H), 5.48 (s, 2H), 4.18 (q, J=7.1 Hz, 2H), 1.18 (t, J=7.1 Hz, 3H).

$^{13}$C NMR (126 MHz, CDCl$_3$) δ 161.0, 155.6, 138.1, 136.2, 135.4, 133.4, 132.7 (q, J$_C$-f=33.7 Hz), 127.1, 126.6, 124.5, 124.3, 122.8 (q, J$_{c-f}$=273.4 Hz), 121.5, 115.8, 122.1, 110.4, 102.5, 62.4, 50.0, 13.9.

Experimental Detail for the Synthesis of JXL086

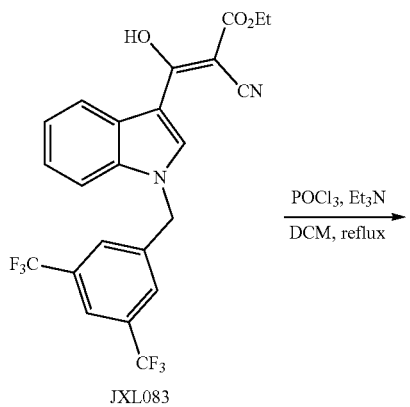

JXL083

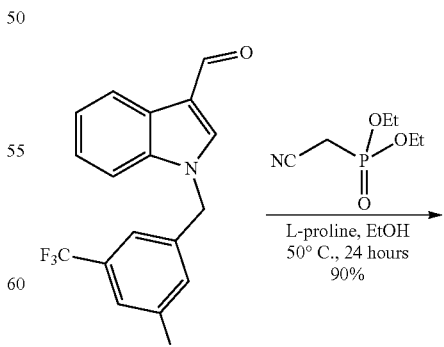

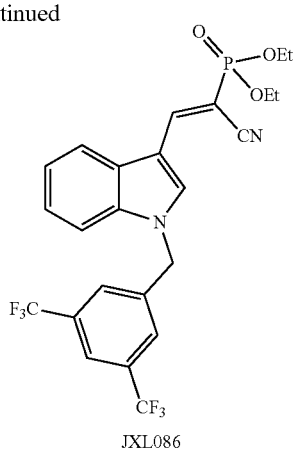

JXL086

Diethyl (E)-(2-(1-(3,5-bis(trifluoromethyl)benzyl)-1H-indol-3-yl)-1-cyanovinyl)phosphonate (JXL086) To the solution of 1-(3,5-bis(trifluoromethyl)benzyl)-1H-indole-3-carboxaldehyde (1 mmol, 371 mg) in ethanol (3 mL) were added diethyl cyanomethylphosphate (1.3 equiv, 1.3 mmol, 204 μL) and L-proline (40 mol %, 0.4 mmol, 58 mg). The reaction was stirred at 50° C. for 24 h. After completion of the reaction as indicated by TLC, the reaction solvent was evaporated by flowing air over the open flask. The solid was purified by flash column chromatography (hexanes:ethyl acetate=2:1) to afford the desired product JXL086 (yield: 90%, 477 mg).

$^1$H NMR (500 MHz, CDCl$_3$) δ 8.55 (s, 1H), 8.33 (d, J=19.7 Hz, 1H), 7.86 (d, J=7.9 Hz, 1H), 7.83 (s, 1H), 7.58 (s, 2H), 7.31 (m, 2H), 7.22 (m, 1H), 5.54 (s, 2H), 4.21 (m, 4H), 1.39 (t, J=7.0 Hz, 6H).

$^{13}$C NMR (126 MHz, CDCl$_3$) δ 149.8, 138.3, 135.8, 132.7 (q, J$_{c-f}$=33.7 Hz), 132.6, 128.2, 126.8, 124.5, 123.0, 122.9 (q, J$_{c-f}$=273.4 Hz), 122.5, 119.0, 117.8 (d, J$_{c-f}$=11.3 Hz), 112.2 (d, J$_{c-f}$=18.9 Hz), 110.3, 91.6 (d, J$_{c-f}$=207.9 Hz), 63.2, 50.4, 16.3.

JXL095 was Synthesized by the Similar Route as JXL086.

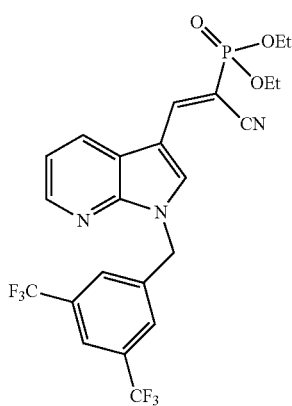

JXL095

Diethyl (E)-(2-(1-(3,5-bis(trifluoromethyl)benzyl)-1H-pyrrolo[2,3-b]pyridin-3-yl)-1-cyanovinyl)phosphonate (JXL095)

$^1$H NMR (500 MHz, CDCl$_3$) δ 8.58 (s, 1H), 8.46 (dd, J=4.7, 1.4 Hz, 1H), 8.24 (d, J=19.5 Hz 1H), 8.20 (dd, J=8.0, 1.4 Hz, 1H), 7.82 (s, 1H), 7.77 (s, 2H), 7.32 (dd, J=8.0, 4.7 Hz, 1H), 5.67 (s, 2H), 4.22 (m, 4H), 1.40 (t, J=7.1 Hz, 6H).

$^{13}$C NMR (126 MHz, CDCl$_3$) δ 149.2 (d, J$_{c-p}$=8.2 Hz), 147.4, 145.6, 138.6, 132.4 (q, J$_{c-f}$=33.7 Hz), 132.0, 127.9, 127.8, 123.0 (q, J$_{c-f}$=273.4 Hz), 122.4, 119.9, 118.9, 117.4 (d, J$_{c-p}$=11.3 Hz), 110.5 (d, J$_{c-p}$=19.5 Hz), 92.8 (d, J$_{c-p}$=205.1 Hz), 63.4, 48.3, 16.3.

Experimental Detail for the Synthesis of JXL096

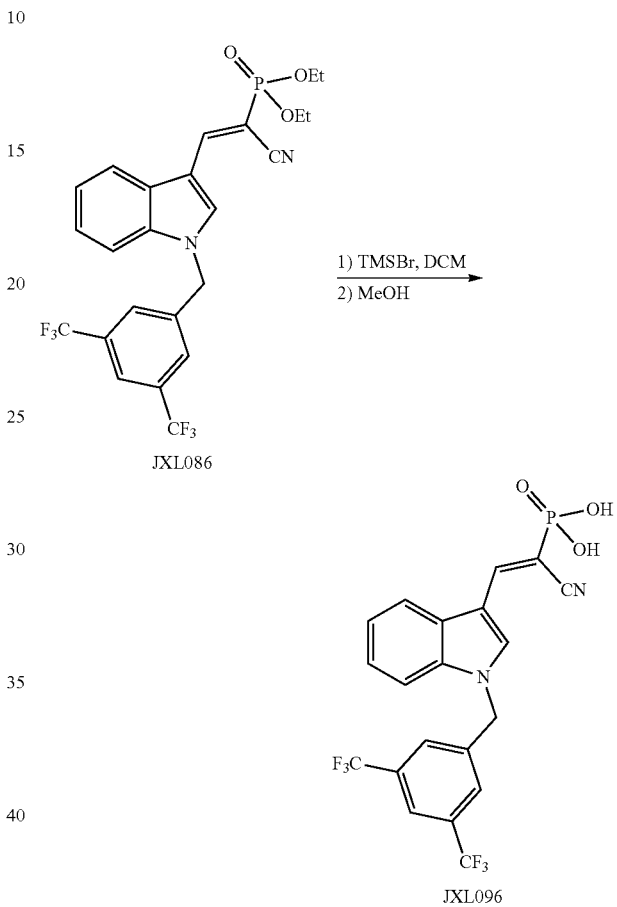

(E)-(2-(1-(3,5-Bis(trifluoromethyl)benzyl)-1H-indol-3-yl)-1-cyanovinyl)phosphonic Acid (JXL096)

A solution of JXL086 (30 mg, 0.057 mmol) in dichloromethane (2 mL) was cooled to 0° C. and bromotrimethylsilane (40 μL, 0.3 mmol) was added dropwise under argon. The mixture was warmed to 21° C. and stirred for 12 h. The solvent was evaporated under vacuum and the resulting residue was then dissolved in methanol (2 mL). The mixture was stirred at 21° C. for 2 h. Evaporation of all volatiles under vacuum gave the phosphoric acid JXL096 (yield: 92%, 25 mg).

$^1$H NMR (500 MHz, CD$_3$OD) δ 8.58 (s, 1H), 8.25 (d, J=19.6 Hz, 1H), 7.90 (s, 1H), 7.87 (m, 1H), 7.76 (s, 2H), 7.45 (m, 1H), 7.31 (m, 2H), 5.75 (s, 2H).

$^{13}$C NMR (126 MHz, CD$_3$OD) δ 146.7 (J$_{c-p}$=7.2 Hz), 140.2, 136.1, 132.1, 131.9 (q, J$_{c-f}$=33.7 Hz), 128.0, 127.2, 123.8, 122.3, 123.2 (q, J$_{c-f}$=273.4 Hz), 121.4, 118.2, 117.4 (d, J$_{c-p}$=11.3 Hz), 111.5 (J$_{c-p}$=18.4 Hz), 110.5, 94.6 (d, J$_{c-p}$=201.2 Hz), 49.1.

Experimental Detail for the Synthesis of JXL092

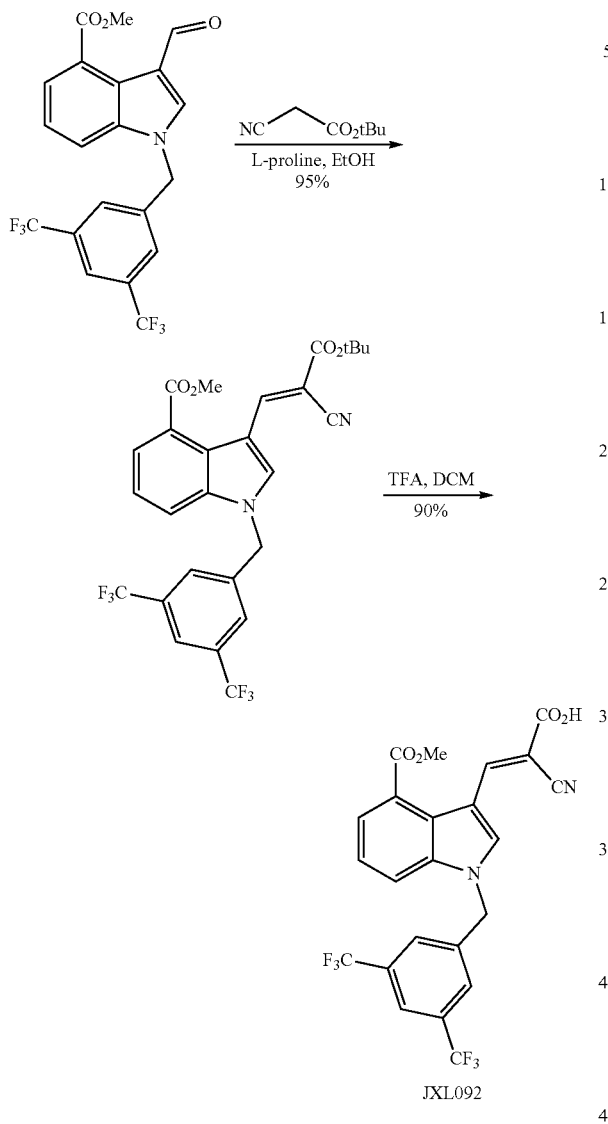

To a solution of methyl 1-(3,5-bis(trifluoromethyl)benzyl)-3-formyl-1H-indole-4-carboxylate (1 mmol, 429 mg) in ethanol (3 mL) were added tert-butyl 2-cyanoacetate (1.3 equiv, 1.3 mmol, 183 µL) and L-proline (40 mol %, 0.4 mmol, 58 mg). The reaction was stirred at 21° C. for 12 h and a yellow solid precipitated gradually. After completion of the reaction, ice-cold water (2 mL) was added into the reaction. The solid was separated by Buchner funnel filtration and washed with water (2 mL×3) and dried to afford the desired product. yield: 95%, 524 mg.

(E)-3-(1-(3,5-Bis(trifluoromethyl)benzyl)-4-(methoxycarbonyl)-1H-indol-3-yl)-2-cyanoacrylic Acid (JXL092)

To the solution of methyl (E)-1-(3,5-bis(trifluoromethyl)benzyl)-3-(3-(tert-butoxy)-2-cyano-3-oxoprop-1-en-1-yl)-1H-indole-4-carboxylate (0.5 mmol, 276 mg) in dichloromethane (2 mL) was added trifluoroacetic acid (3 equiv, 1.5 mmol, 0.2 mL). The reaction mixture was stirred at 21° C. for 30 min and a yellow solid precipitated. After the reaction was complete as shown by TLC, the reaction solvent was evaporated by flowing air over the open flask. The solid was washed by 2 mL of solvent mixture (hexanes/EtOAc=5:1) 5 to 10 times and monitored by TLC until all the non-polar impurities disappeared. Finally, the purity of the product was checked by NMR. yield: 90%, 223 mg.

$^1$H NMR (500 MHz, CDCl$_3$) δ 9.09 (s, 1H), 8.58 (s, 1H), 7.75 (d, J=7.5 Hz, 1H), 7.68 (s, 1H), 7.47 (s, 2H), 7.34 (d, J=8.2 Hz, 1H), 7.20 (app. t, J=7.9 Hz, 1H), 5.51 (s, 2H), 3.87 (s, 3H).

$^{13}$C NMR (126 MHz, CDCl$_3$) δ 167.8, 165.1, 149.5, 138.2, 137.2, 134.8, 132.3 (q, J$_{c-f}$=33.7 Hz), 126.8, 126.2, 125.5, 124.8, 123.3, 122.8 (q, J$_{c-f}$=273.4 Hz), 122.3 118.2, 114.7, 110.9, 97.2, 52.4, 50.2.

Experimental Detail for the Synthesis of JXL094

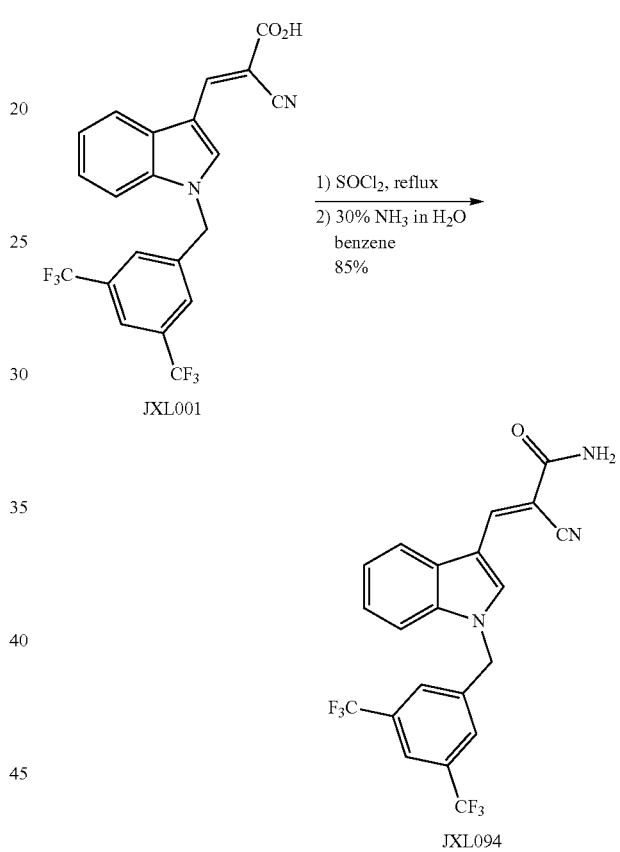

(E)-3-(1-(3,5-Bis(trifluoromethyl)benzyl)-1H-indol-3-yl)-2-cyanoacrylamide (JXL094)

The mixture of (E)-3-(1-(3,5-bis(trifluoromethyl)benzyl)-1H-indol-3-yl)-2-cyanoacrylic acid JXL001 (0.1 mmol, 43.8 mg) and thionyl chloride (0.5 ml) was refluxed for 1 h. After concentration under vacuum, the resulting acyl chloride was dissolved in 1 ml benzene and 30% ammonia in water (1 ml) was added. The reaction mixture was stirred at 21° C. for 24 h. After completion of the reaction as indicated by TLC, the reaction solvent was evaporated under vacuum. The solid was purified by flash column chromatography (hexanes: ethyl acetate=2:1) to afford the desired product JXL094 (yield: 85%, 37 mg).

$^1$H NMR (500 MHz, CDCl$_3$) δ 8.70 (s, 1H), 8.47 (s, 1H), 7.92 (d, J=7.1 Hz, 1H), 7.85 (s, 1H), 7.58 (s, 2H), 7.34 (m, 2H), 7.23 (m, 1H), 5.55 (s, 2H).

$^{13}$C NMR (126 MHz, CDCl$_3$) δ 163.0, 144.8, 138.1, 136.0, 132.7 (q, J$_{c-f}$=33.7 Hz), 132.5, 128.6, 126.8, 126.1, 124.6, 123.1, 122.9 (q, J$_{c-f}$=273.4 Hz), 122.6, 119.3, 111.3, 110.3, 96.1, 50.4.

Additional exemplary compounds of the present invention can be prepared by methods analogous to those described above.

Example 2: Treatment of Epithelial Cells with Exemplary Compounds

To determine whether these compounds could promote cellular lactate production, we treated cultured epithelial cells with the compounds and measured lactate levels in the culture media using a Nova Biomedical BioProfile Basic Analyzer. Briefly, cultured epithelial cells were treated with DMSO, UK-5099 (also called JXL001), or certain of the exemplary compounds disclosed herein for 24-30 hours, and media lactate levels were measured and normalized to cell number and duration of the experiment to acquire a cellular lactate production rate (nmol lactate, million cells, hour).

Figure 12:
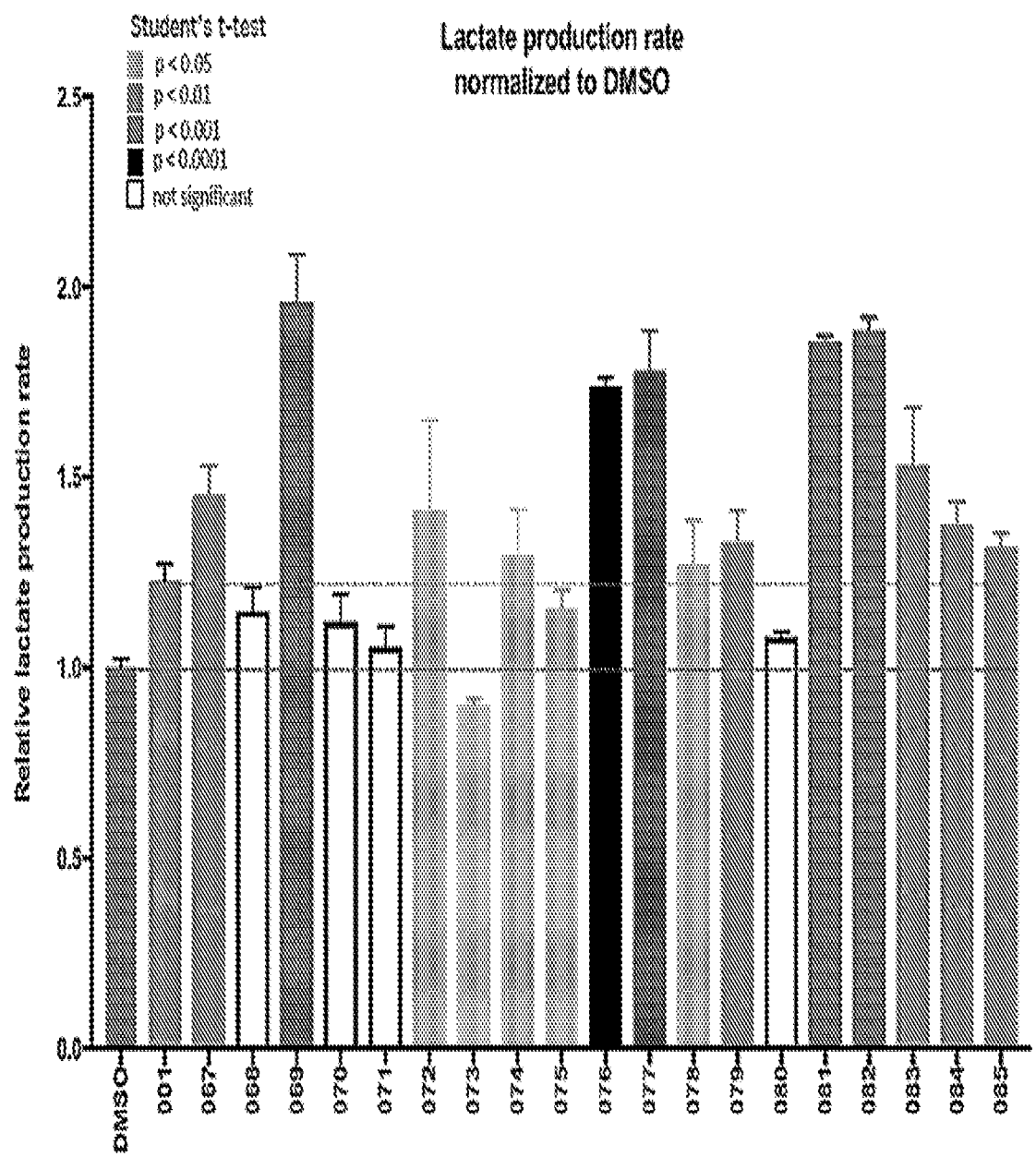
FIG. 12 shows the effect on lactate production of certain Mpc1 inhibitors described herein.
Figure 13:
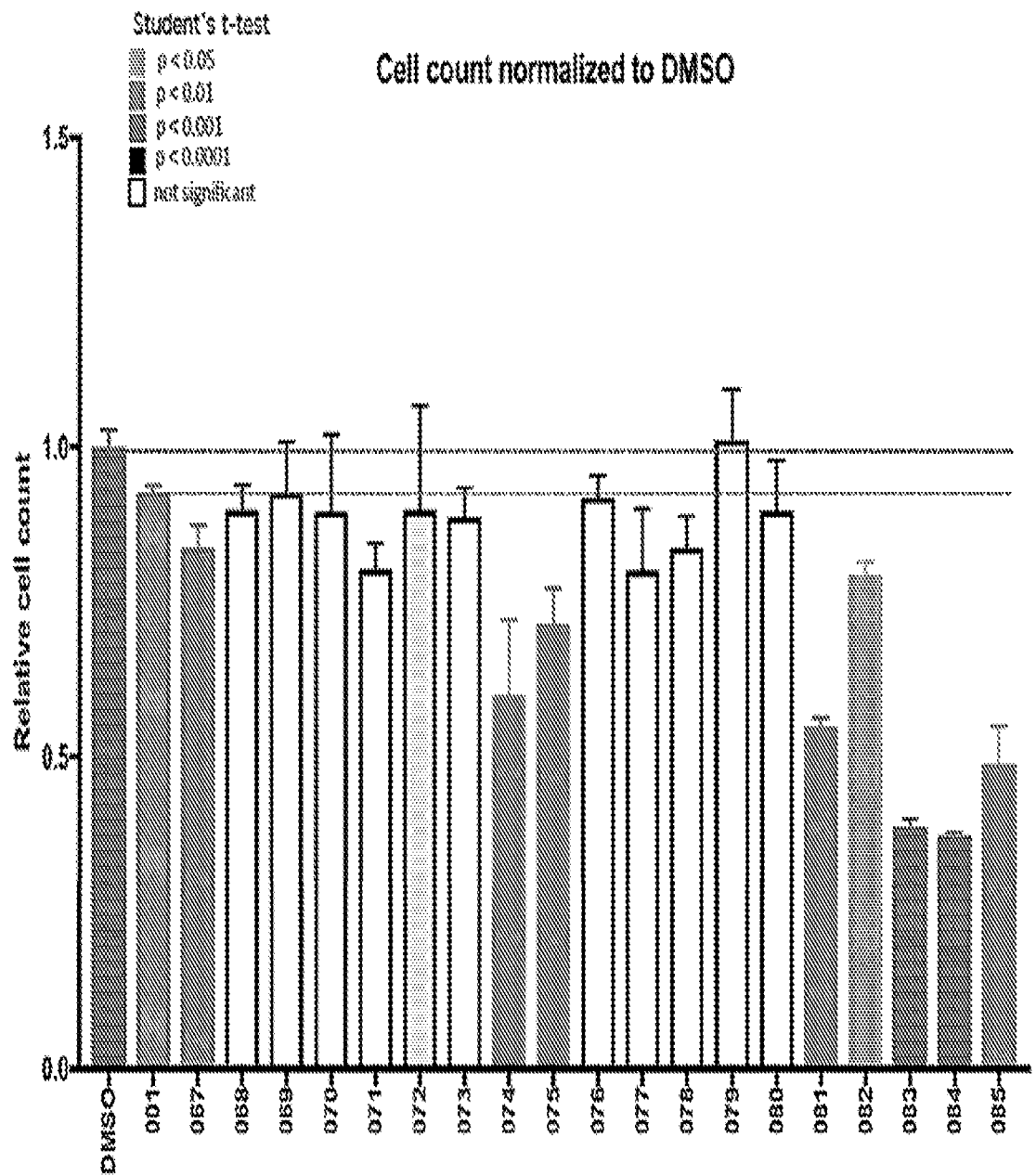
FIG. 13 shows the effect on total cell count of certain Mpc1 inhibitors described herein, normalized to DMSO treatment.
Figure 14:
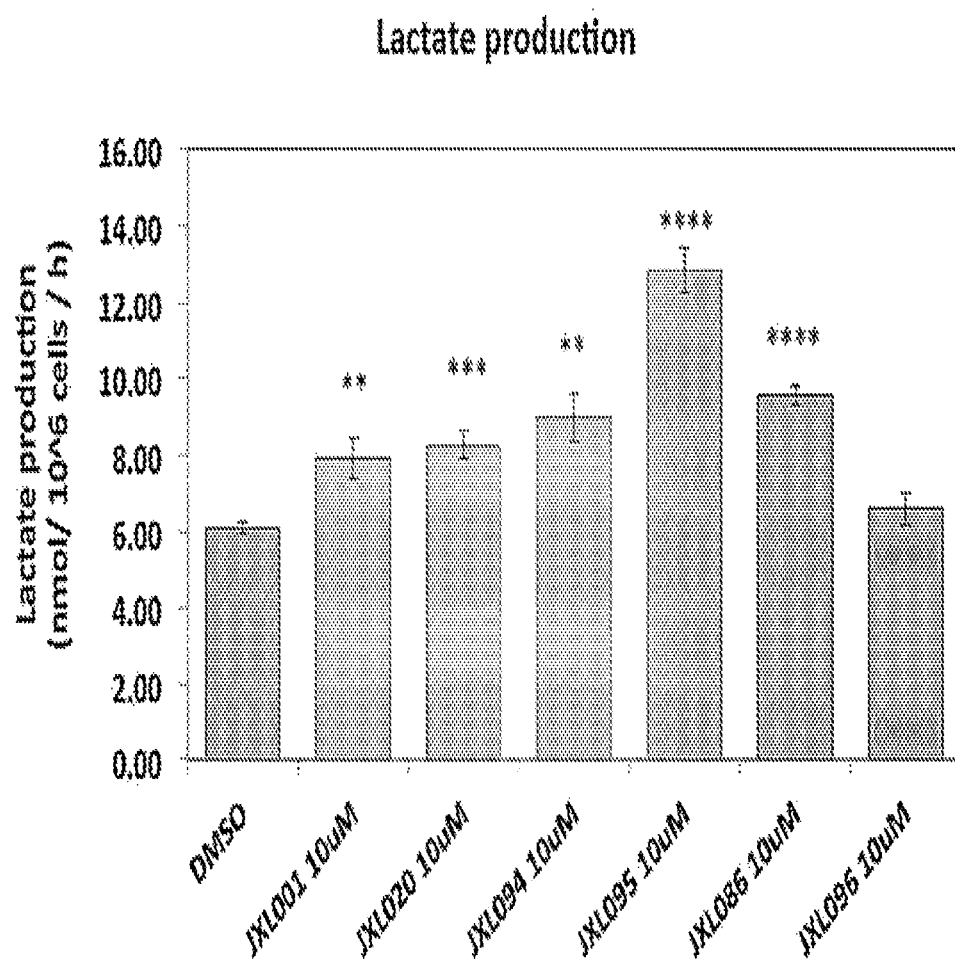
FIG. 14 shows the effect on cell lactate production of certain Mpc1 inhibitors described herein, normalized to DMSO treatment.
Figure 15:
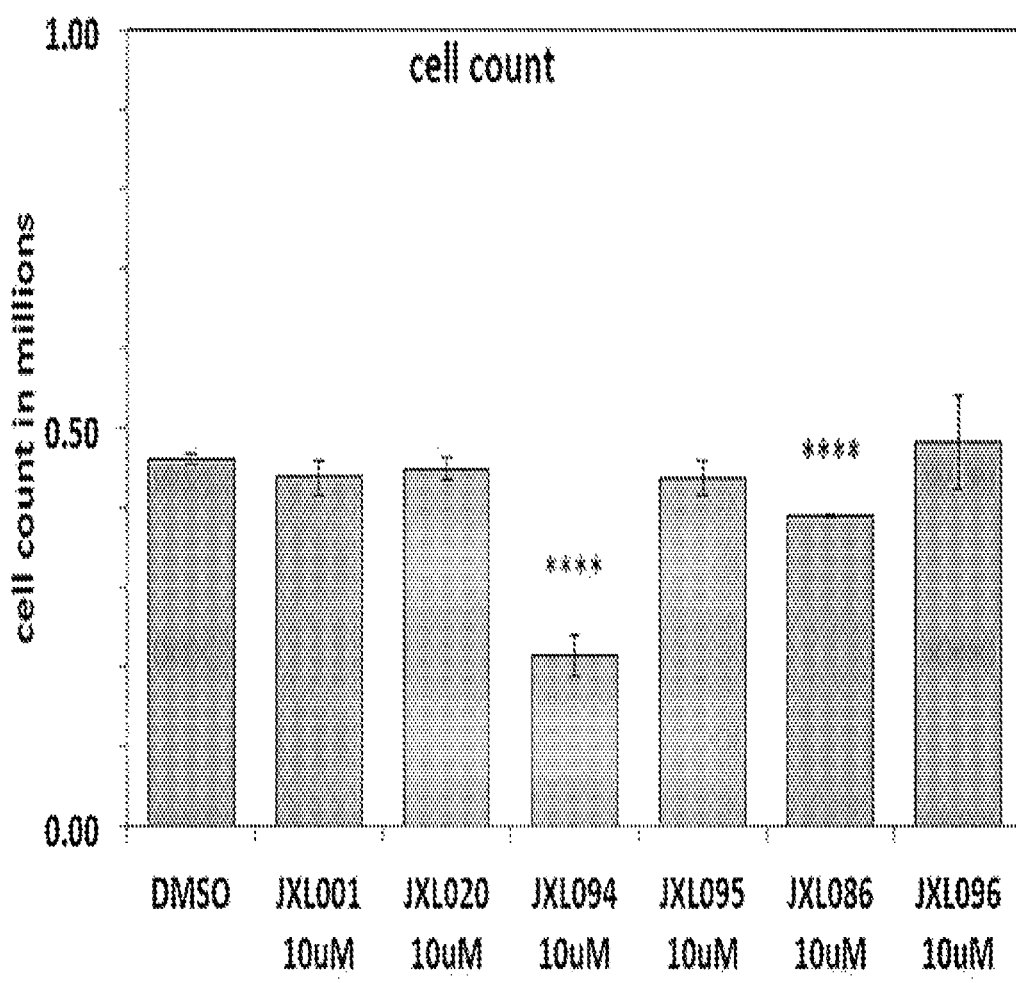
FIG. 15 shows the effect on total cell count of certain Mpc1 inhibitors described herein, normalized to DMSO treatment.
Figure 16:
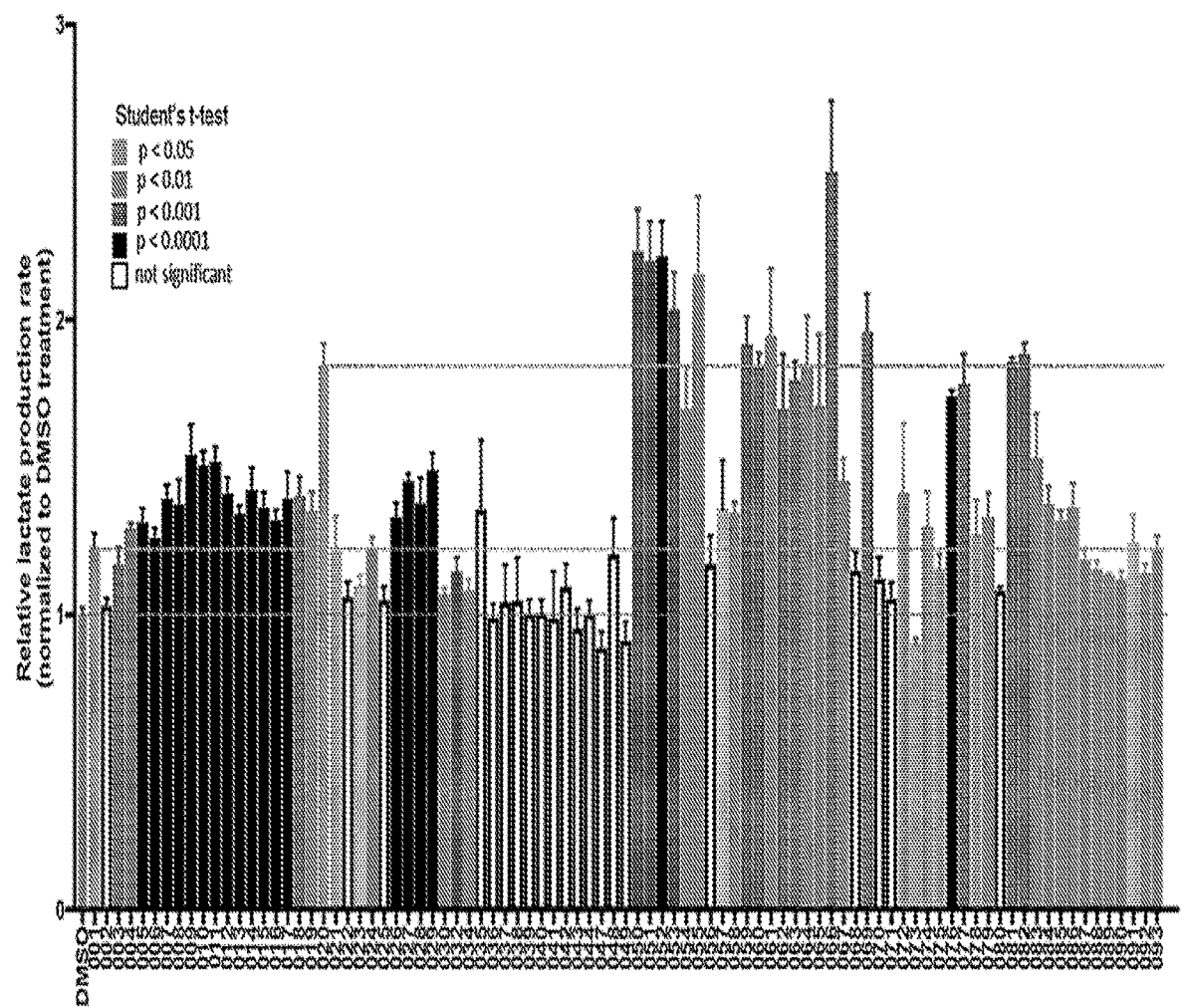
FIG. 16 shows the effect on cell lactate production of certain Mpc1 inhibitors described herein, normalized to DMSO treatment.
Figure 17:
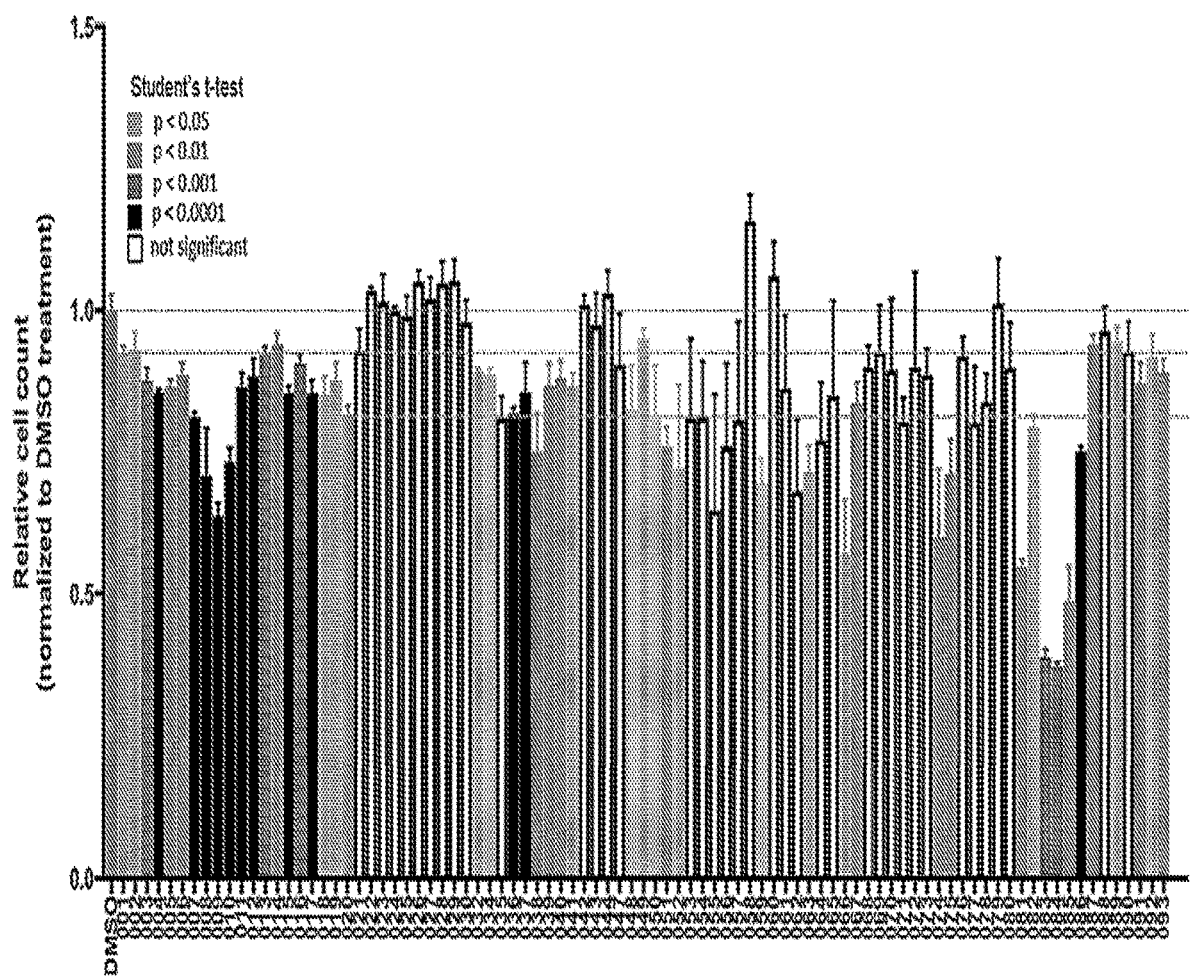
FIG. 17 shows the effect on total cell count of certain Mpc1 inhibitors described herein, normalized to DMSO treatment.
Figure 18:
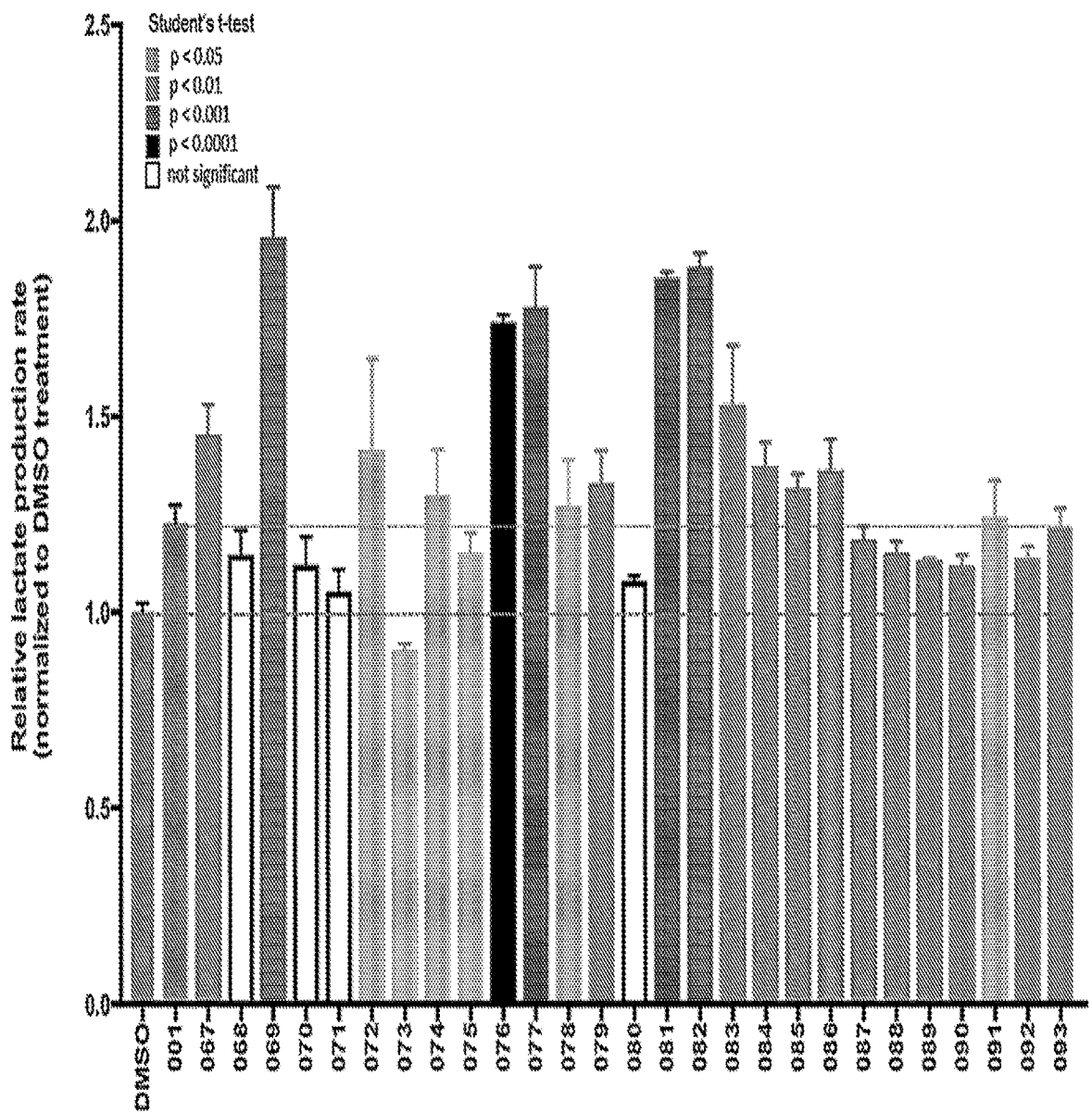
FIG. 18 shows the effect on cell lactate production of certain Mpc1 inhibitors described herein, normalized to DMSO treatment.
Figure 19:
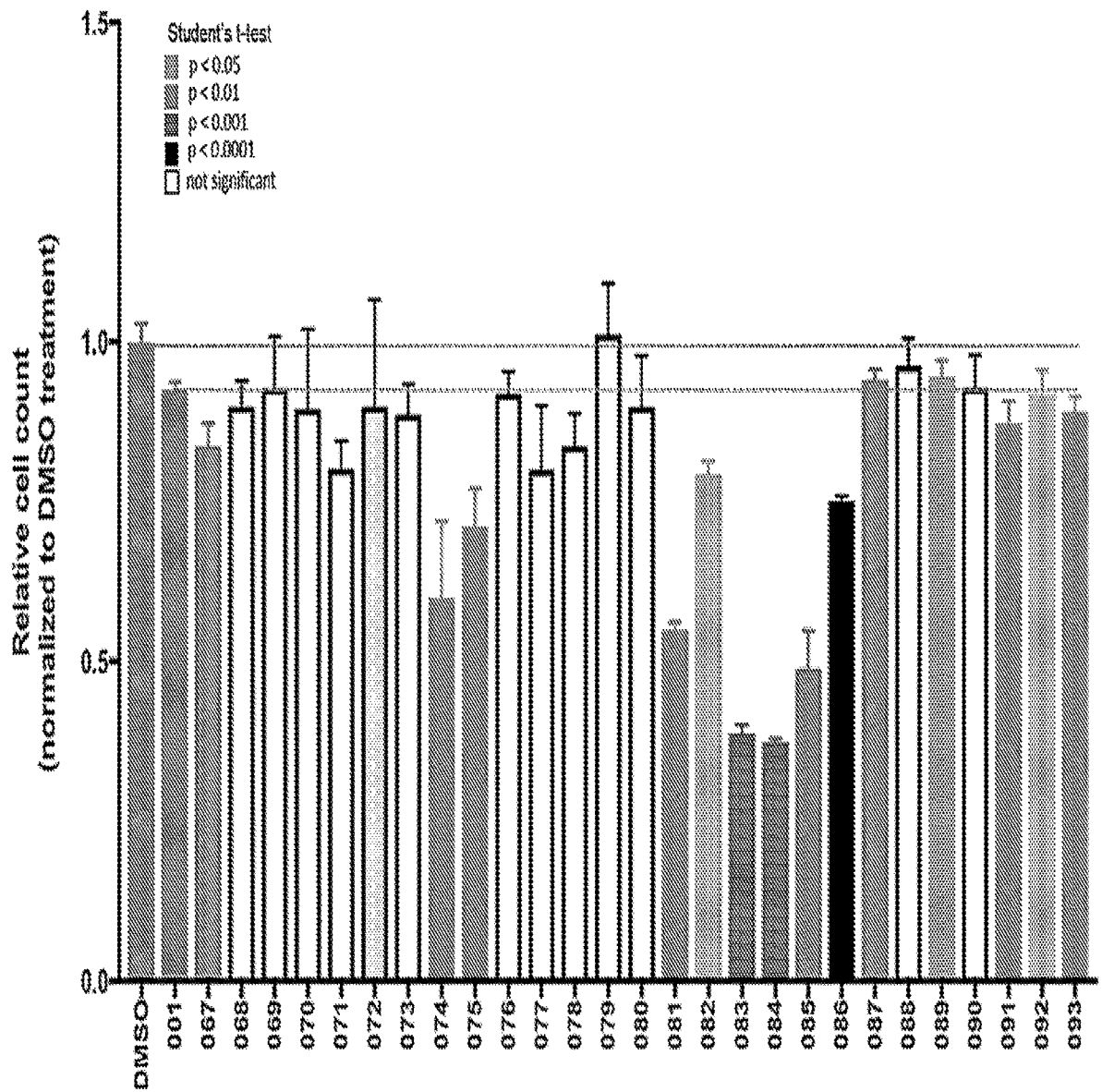
FIG. 19 shows the effect on total cell count of certain Mpc1 inhibitors described herein, normalized to DMSO treatment.

Lactate production rates of treated cells are shown in FIGS. 8, 9, and 12. As expected based on the present disclosure, since they are UK-5099 analogues, most of the novel compounds assayed increased lactate production. Furthermore, the total cell count following treatment with the UK-5099 analogues is shown in FIG. 13. Most of the compounds were tolerated by the cells. A separate assay was performed to calculate the EC50 of some of the compounds as shown in FIG. 10.

Example 3: In Vivo Test of Exemplary Compounds

To determine the efficacy of the compounds on the hair cycle, mice were shaved at postnatal day 50, and topically treated every other day with a compound disclosed herein suspended in lotion in every other day for 2 weeks, and pictures were taken. As seen in FIG. 11, all the analogues that showed the ability to promote lactate production in the in vitro assay were also able to stimulate hair growth over the course of 2 weeks.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound of formula I or a pharmaceutically acceptable salt thereof:

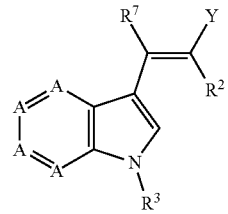

(I)

wherein:
each A is independently CH, CR$^4$, or N;
Y is carboxyl, ester, amide, or

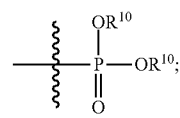

R$^2$ is CN;
R$^3$ is aralkyl substituted by two R$^5$ in the meta positions, wherein each R$^5$ is independently selected from alkyl, alkoxy, and halo;
each R$^4$ is independently alkyl, carboxyl, halo, hydroxy, ester, or CN;
R$^7$ is hydrogen, alkyl, halo, hydroxyl, alkoxy, or acyloxy; and
R$^{10}$ is hydrogen or alkyl.

2. The compound of claim 1, wherein the compound has a structure represented by formula III or a pharmaceutically acceptable salt thereof:

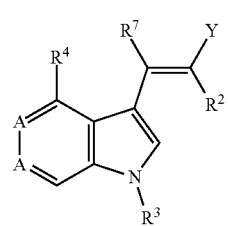

(III)

wherein,
Y is carboxyl, ester, amide, or

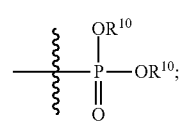

R$^2$ is CN;
R$^3$ is aralkyl substituted by two R$^5$ in the meta positions, wherein each R$^5$ is independently selected from alkyl, alkoxy, and halo;
each R$^4$ is independently alkyl, carboxyl, halo, hydroxy, ester, or CN;
R$^7$ is hydrogen, alkyl, halo, hydroxyl, alkoxy, or acyloxy; and
R$^{10}$ is hydrogen or alkyl.

3. The compound of claim 1, wherein Y is carboxyl, ester, or amide.

4. The compound of claim 1, wherein the compound has a structure represented by formula V or a pharmaceutically acceptable salt thereof:

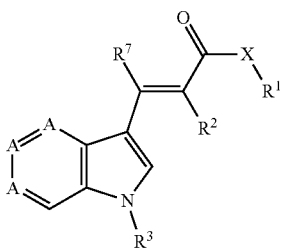

(V)

wherein:
each A is independently CH, $CR^4$, or N;
X is $NR^6$ or O;
$R^1$ is H or lower alkyl; or either $R^1$ and $R^6$ or $R^1$ and $R^2$, together with the atoms that separate them, complete a heterocycle;
$R^2$ is CN;
$R^3$ is aralkyl substituted by two $R^5$ in the meta positions, wherein each $R^5$ is independently selected from alkyl, alkoxy, and halo;
each $R^4$ is independently alkyl, carboxyl, halo, hydroxy, or CN;
$R^6$ is H, alkyl, or cycloalkyl;
$R^7$ is hydrogen, alkyl, halo, hydroxyl, alkoxy, or acyloxy; and
n is 0-4.

5. The compound of claim 1, wherein at least one A is N.

6. The compound of claim 4, wherein X is NH or O.

7. The compound of claim 4, wherein $R^1$ is H or lower alkyl.

8. The compound of claim 1, wherein each $R^5$ is independently selected from fluoroalkyl or fluoro.

9. The compound of claim 4, wherein the compound is represented by formula Vb:

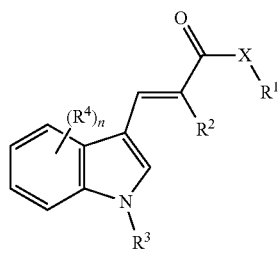

(Vb)

wherein n is 0-3.

10. The compound of claim 9, wherein n is 0 or 1.

11. The compound of claim 1, wherein $R^4$ is halo or haloalkyl.

12. The compound of claim 1, wherein $R^7$ is hydrogen, hydroxyl, halo, or acyloxy.

13. A compound selected from:

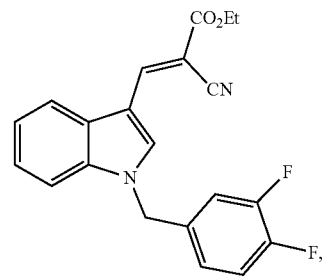

JXL009

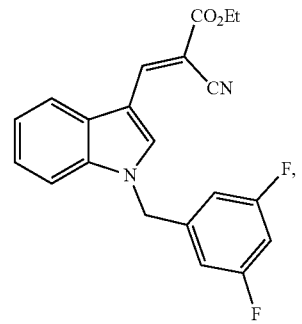

JXL010

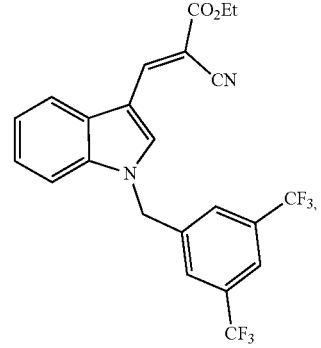

JXL011

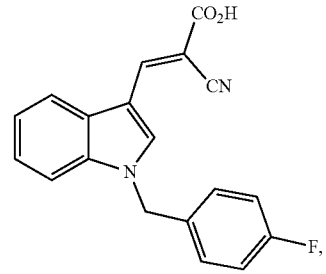

JXL015

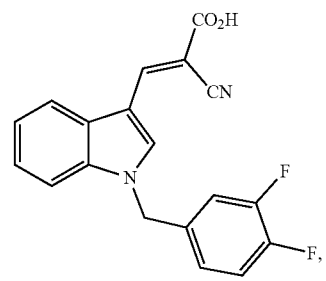

JXL016

JXL017 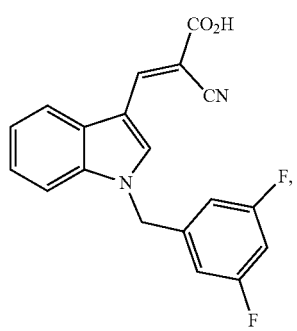
JXL019 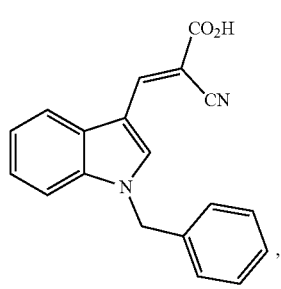
JXL020 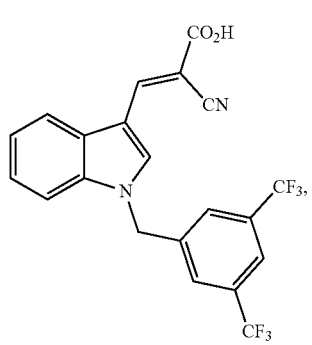
JXL036 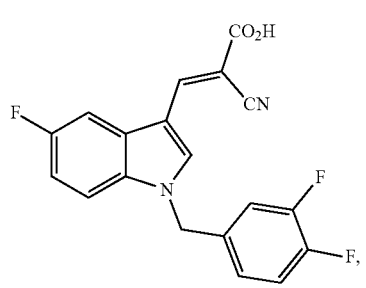
JXL037 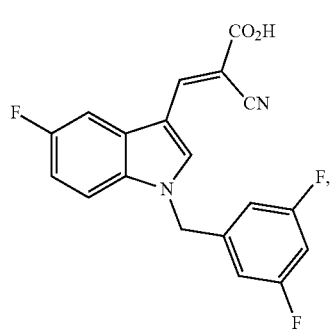
JXL038 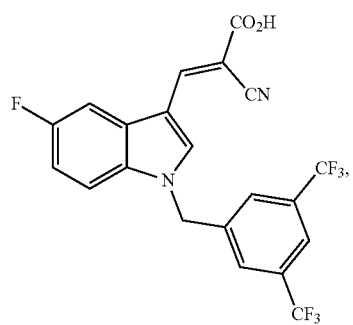
JXL039 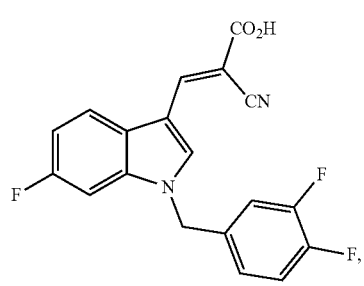
JXL040 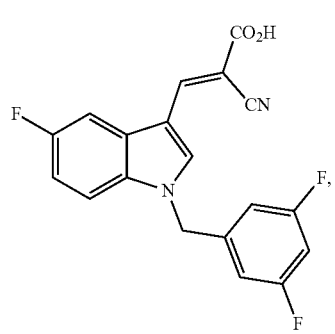
JXL041 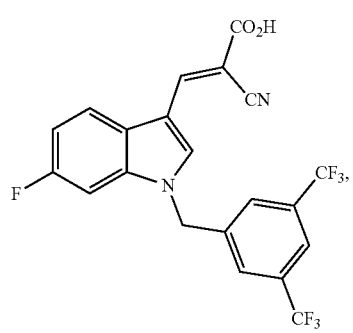
JXL050 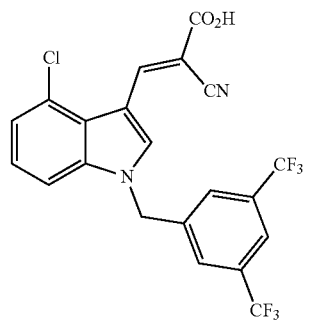

JXL051 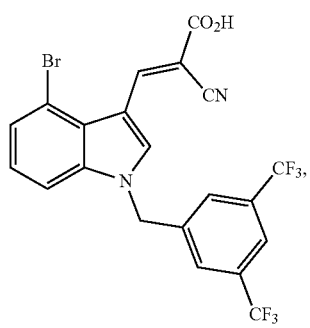
JXL052 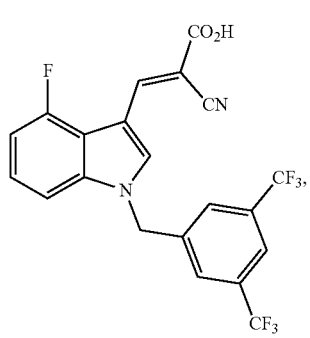
JXL053 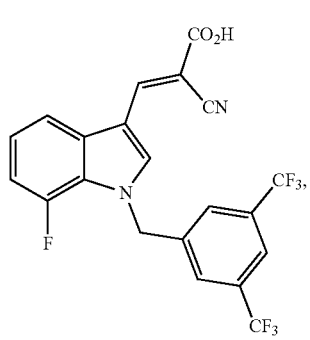
JXL054 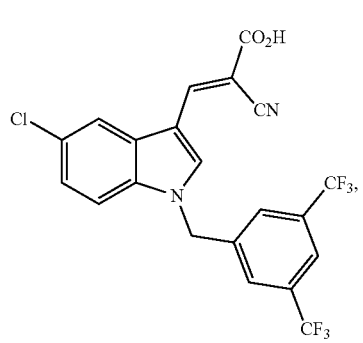
JXL055 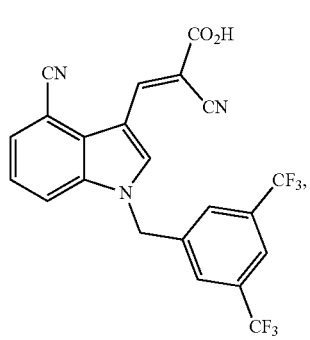
JXL056 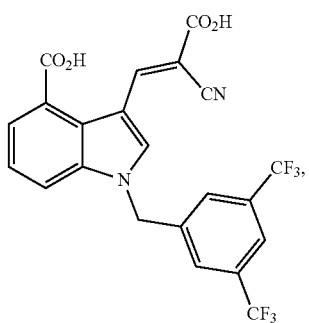
JXL057 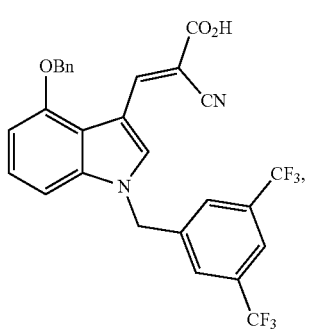
JXL058 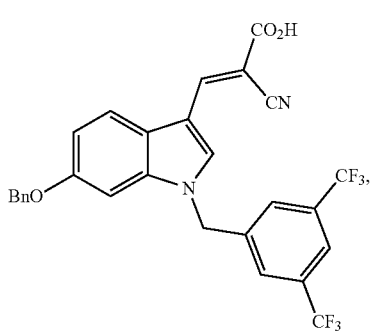
JXL059 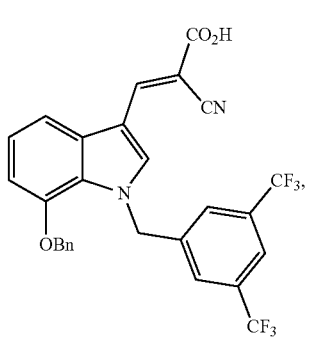
JXL060 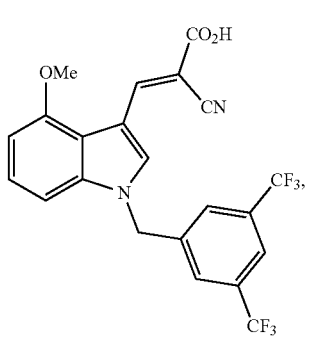

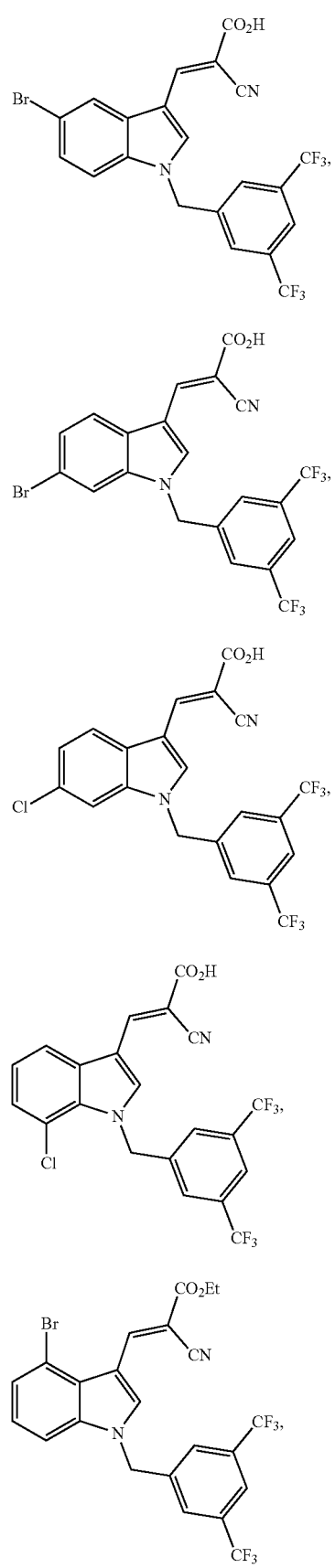
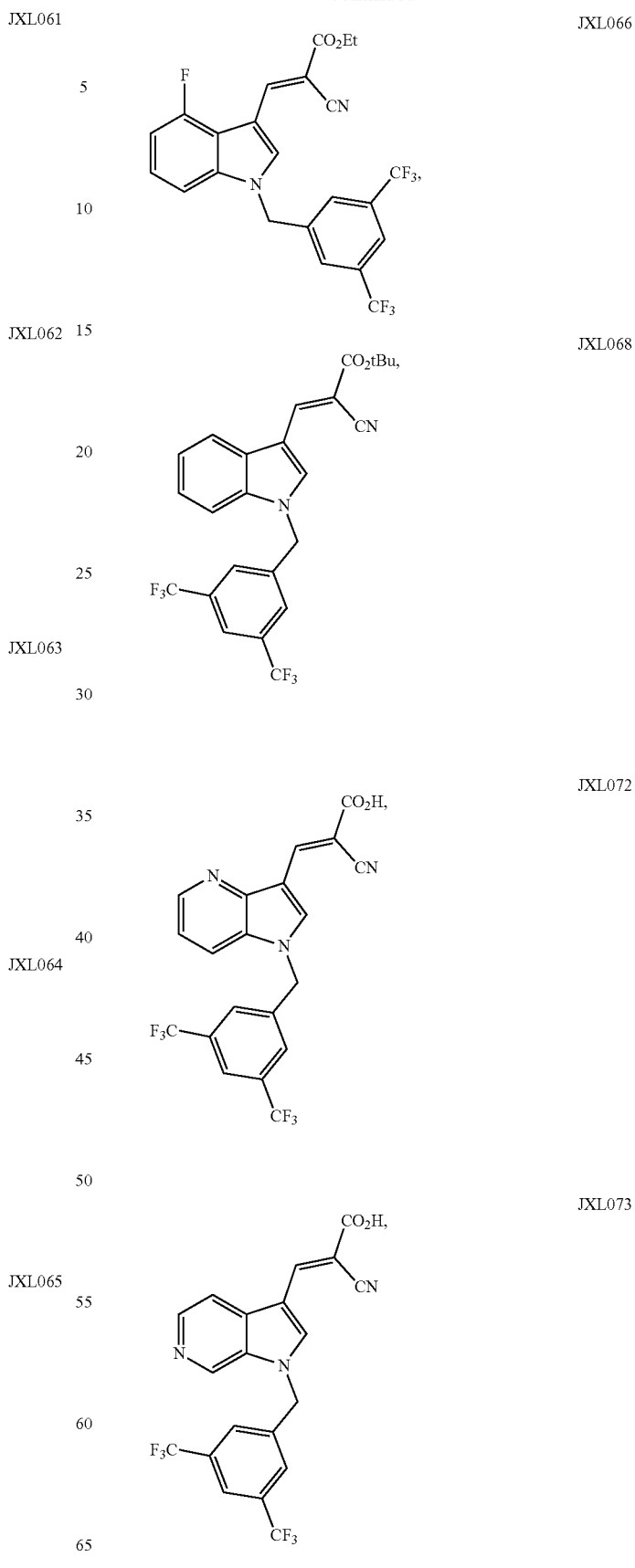

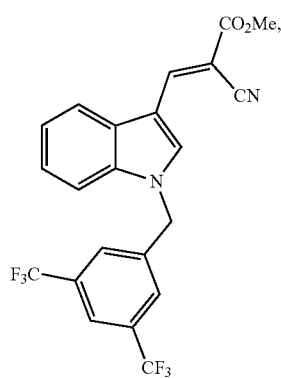 JXL078
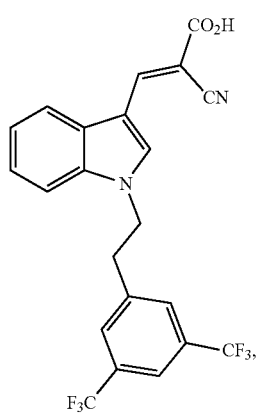 JXL079
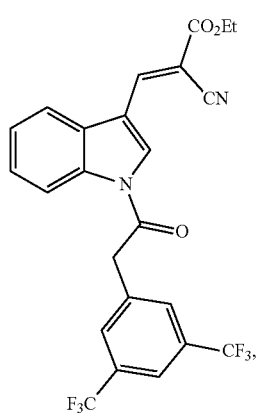 JXL080
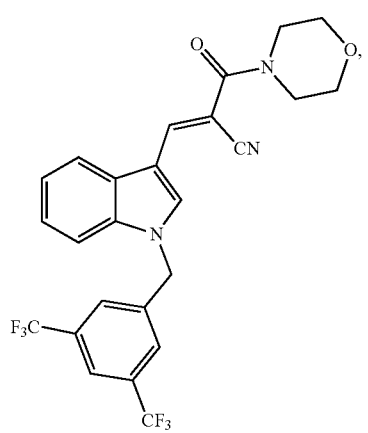 JXL081
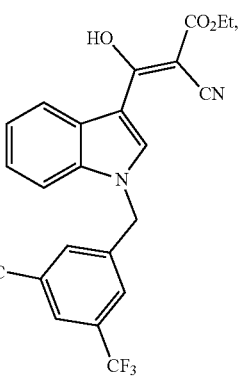 JXL083
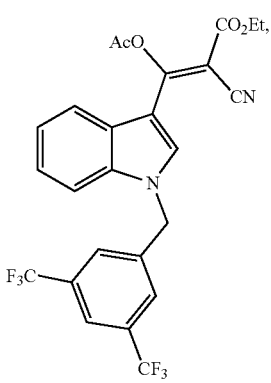 JXL084
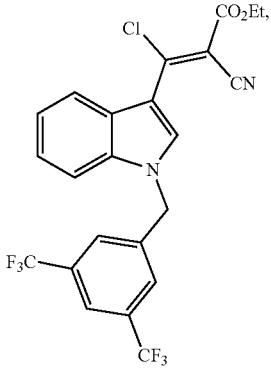 JXL085
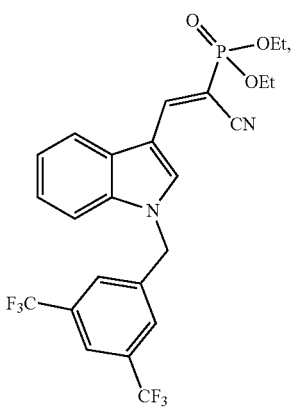 JXL086

-continued
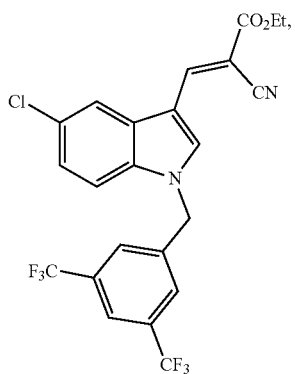
JXL089
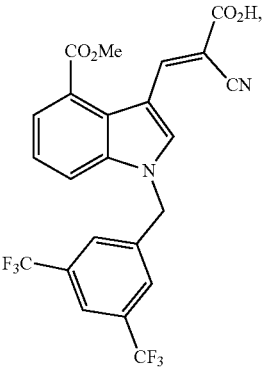
JXL092
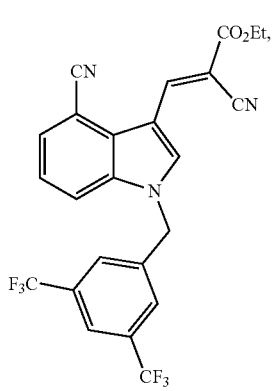
JXL090
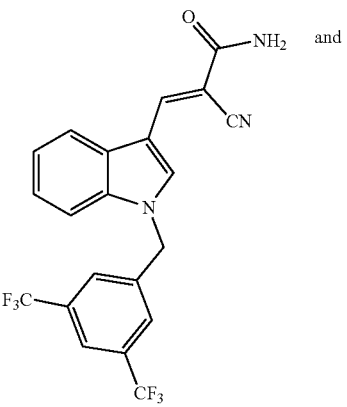
JXL094
and
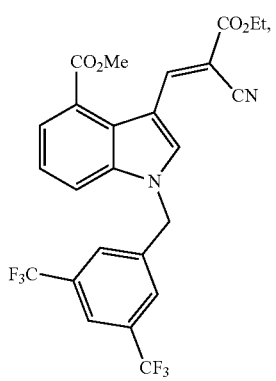
JXL091
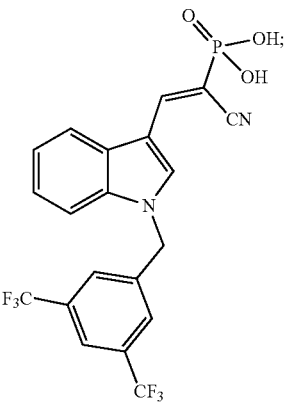
JXL096
or a pharmaceutically acceptable salt thereof.
* * * * *

UNITED STATES PATENT AND TRADEMARK OFFICE
CERTIFICATE OF CORRECTION

PATENT NO. : 12,227,503 B2  
APPLICATION NO. : 18/241583  
DATED : February 18, 2025  
INVENTOR(S) : William E. Lowry et al.

Page 1 of 1

It is certified that error appears in the above-identified patent and that said Letters Patent is hereby corrected as shown below:

In the Claims

At Column 102, Lines 5-14, in Claim 1, please replace:

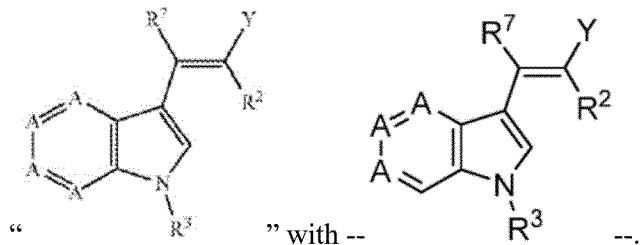

" with --  --.

At Column 111, Lines 34-49, in Claim 13, please delete the following structure:

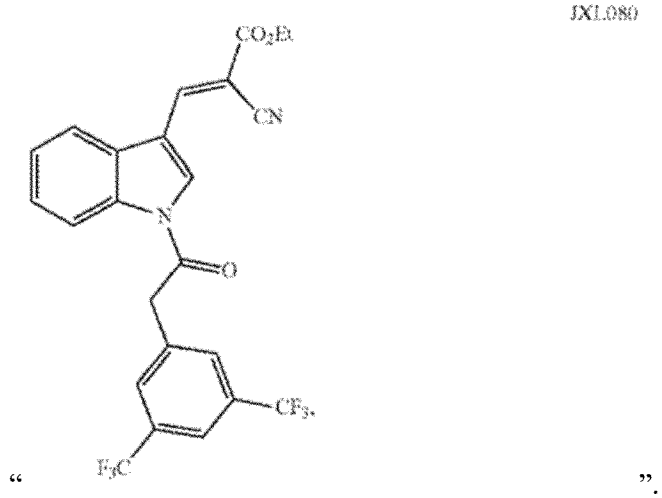

" ".

Signed and Sealed this  
First Day of April, 2025

Coke Morgan Stewart  
*Acting Director of the United States Patent and Trademark Office*